US009642902B2

(12) United States Patent
Wren et al.

(10) Patent No.: US 9,642,902 B2
(45) Date of Patent: May 9, 2017

(54) GLYCOCONJUGATE VACCINES

(71) Applicant: London School of Hygiene and Tropical Medicine, London (GB)

(72) Inventors: Brendan Wren, London (GB); Jon Cuccui, London (GB); Madeleine Moule, London (GB)

(73) Assignee: London School of Hygiene and Tropical Medicine, London (GB)

( * ) Notice: Subject to any disclaimer, the term of this patent is extended or adjusted under 35 U.S.C. 154(b) by 0 days.

(21) Appl. No.: 14/655,210

(22) PCT Filed: Jan. 21, 2014

(86) PCT No.: PCT/GB2014/050159
§ 371 (c)(1),
(2) Date: Jun. 24, 2015

(87) PCT Pub. No.: WO2014/114926
PCT Pub. Date: Jul. 31, 2014

(65) Prior Publication Data
US 2015/0328301 A1 Nov. 19, 2015

(30) Foreign Application Priority Data

Jan. 22, 2013 (GB) .................................. 1301085.5

(51) Int. Cl.
*A61K 39/02* (2006.01)
*A61K 39/00* (2006.01)
*A61K 49/00* (2006.01)
*A61K 47/48* (2006.01)
*C07K 14/21* (2006.01)
*C12M 1/00* (2006.01)
*A61K 45/06* (2006.01)
*C07K 14/195* (2006.01)

(52) U.S. Cl.
CPC .......... *A61K 39/0208* (2013.01); *A61K 45/06* (2013.01); *A61K 47/4833* (2013.01); *C07K 14/195* (2013.01); *C07K 14/21* (2013.01); *C12M 23/00* (2013.01); *A61K 2039/55566* (2013.01); *A61K 2039/55572* (2013.01); *A61K 2039/6031* (2013.01); *A61K 2039/6037* (2013.01); *A61K 2039/6068* (2013.01); *A61K 2039/70* (2013.01)

(58) Field of Classification Search
CPC ......... A61K 39/00; A61K 39/02; A61K 39/08
USPC .............................. 424/9.1, 9.2, 184.1, 234.1
See application file for complete search history.

(56) References Cited

U.S. PATENT DOCUMENTS

| 2003/0013175 A1 | 1/2003 | Koizumi et al. |
| 2010/0062484 A1 | 3/2010 | Aebi et al. |
| 2010/0137565 A1 | 6/2010 | Javaud et al. |
| 2011/0274720 A1 | 11/2011 | Wacker et al. |

FOREIGN PATENT DOCUMENTS

| JP | 2005-046031 A | 2/2005 | |
| JP | 2005-046931 A | 2/2005 | |
| WO | WO 99/54342 A1 | 10/1999 | |
| WO | WO 03/102191 A1 | 12/2003 | |
| WO | WO 2007/035897 A2 | 3/2007 | |
| WO | WO 2008/021076 A2 | 2/2008 | |
| WO | WO2008/133645 | * 11/2008 | ............. A61K 39/02 |
| WO | WO 2008/133645 A2 | 11/2008 | |
| WO | WO 2009/026131 A2 | 2/2009 | |
| WO | WO 2009/104074 A2 | 8/2009 | |
| WO | WO2011/115483 | * 9/2011 | ........... A61K 39/395 |
| WO | WO 2011/115483 A1 | 9/2011 | |
| WO | WO 2011/138361 A1 | 11/2011 | |
| WO | WO 2012/158701 A1 | 11/2012 | |

OTHER PUBLICATIONS

Conlan et al., "Mice Vaccinated with the O-antigen of *Francisella tularensis* LVS Lipopolysaccharide Conjugated to Vovine Serum Albumin Develop Varying Degrees of Protective Immunity Against Systemic or Aerosol Challenge with Virulent type A and Type B Strains of the Pathogen," *Vaccine* 20:3465-3471, 2002.

Cuccui et al., "Exploitation of Bacterial N-Linked Glycosylation to Develop a Novel Recombinant Glycoconjugate Vaccine Against *Francisella tularensis*," *Open Biol.* 3:130002, 2013.

Dagan et al., "Glycoconjugate Vaccines and Immune Interference: A Review," *Vaccine* 28:5513-5523, 2010.

Feldman et al., "Engineering N-linked Protein Glycosylation with Diverse O Antigen Lipopolysaccharide Structures in *Escherichia coli*," *Proc Natl Acad Sci. USA* 102:3016-3021, 2005.

Great Britain Search Report dated Jul. 16, 2013 for Great Britain Application No. GB1301085.5.

Great Britain Search Report dated Jul. 18, 2013 for Great Britain Application No. GB1300956.8.

Ihssen et al., "Production of Glycoprotein Vaccines in *Escherichia coli*," *Microbiol. Cell Factories* 9:61, 2010.

Kim et al., "Genetic Modification of the O-Polysaccharide of *Francisella tularensis* Results in an Avirulent Live Attenuated Vaccine," *J Infect Dis.* 205:1056-1065, 2012.

Kowarik et al., "N-Linked Glycosylation of Folded Proteins by the Bacterial Oligosaccharyltransferase," *Science* 314:1148-1150, 2006.

Nikel and Lorenzo, "Implantation of Unmarked Regulatory and Metabolic Modules in Gram-Negative Bacteria with Specialised Mini-Transposon Delivery Vectors," *J Biotechnol.* 163:143-154, 2013.

Prior et al., "Characterization of the O Antigen Gene Cluster and Structural Analysis of the O Antigen of *Francisella tularensis* subsp. *tularensis*," *J Med Microbiol.* 52:845-851, 2003.

Sabido et al., "A Novel Plasmid Vector Designed for Chromosomal Gene Integration and Expression: Use for Developing a Genetically Stable *Escherichia coli* Melanin Production Strain," *Plasmid* 69:16-23, 2013.

Terra et al., "Recent Developments in Bacterial Protein Glycan Coupling Technology and Glycoconjugate Vaccine Design," *J Med Microbiol.* 61:919-926, 2012.

* cited by examiner

*Primary Examiner* — Rodney P Swartz
(74) *Attorney, Agent, or Firm* — Klarquist Sparkman, LLP

(57) ABSTRACT

The disclosure relates to a glycoconjugate vaccine conferring protection against *Francisella tularensis* infections and a method to manufacture a glycoconjugate antigen.

19 Claims, 18 Drawing Sheets

Figure 10: SEQ ID NO: 1

MKKIWLALAGLVLAFSASDQNATGGDQNATGGDQNATGGDQNATAAEEAFDLWNECAKACVLDLKDGVRS
SRMSVDPAIADTNGQGVLHYSMVLEGGNDALKLAIDNALSITSDGLTIRLEGGVEPNKPVRYSYTRQARG
SWSLNWLVPIGHEKPSNIKVFIHELNAGNQLSHMSPIYTIEMGDELLAKLARDATFFVRAHESNEMQPTL
AISHAGVSVVMAQAQPRREKRWSEWASGKVLCLLDPLDGVYNYLAQQRCNLDDTWEGKIYRVLAGNPAKH
DLDIKDNNNSTPTVISHRLHFPEGGSLAALTAHQACHLPLEAFTRHRQPRGWEQLEQCGYPVQRLVALYL
AARLSWNQVDQVIRNALASPGSGGDLGEAIREQPEQARLALTLAAAESERFVRQGTGNDEAGAASADVVS
LTCPVAKDQNRTKGECAGPADSGDALLERNYPTGAEFLGDGGDVSFSTRGTQNWTVERLLQAHRQLEERG
YVFVGYHGTFLEAAQSIVFGGVRARSQDLDAIWRGFYIAGDPALAYGYAQDQEPDARGRIRNGALLRVYV
PRWSLPGFYRTGLTLAAPEAAGEVERLIGHPLPLRLDAITGPEEEGGRVTILGWPLAERTVVIPSAIPTD
PRNVGGDLDPSSIPDKEQAISALPDYASQPGKPPREDLKDQNATGGDQNATGGDQNATGGDQNATVD

Figure 11: SEQ ID NO: 2

MKKIWLALAGLVLAFSASGTDQNATGGDQNATGGDQNATGGDQNATGTMKKIIELSLLSLSIAGLASCST
LGLGGSDDAKASAKDTAAAQTATTEQAAAVSKPTAKVSLNKLGQDKIKATVYTTYNNNPQGSVRLQWQAP
EGSKCHDTSFPITKYAEKNDKTWATVTVKQGNNFCSGKWTANVVYDKEVIASDSINIDQNATGGDQNATG
GDQNATGGDQNATVD

FIGURE 12: SEQ ID NO: 3
MKKIWLALAGLVLAFSASGTDQNATGGDQNATGGDQNATGGDQNATGTMVSREDFIMTINKLSLTDELLNNFGGS
TEVDSVLKNIDFDVSDDASKVLSLSTDYNARNLMALSLVLANNDNINNYNQKYIQKVITVIDKLIDLQVNSIISN
DEFRALEQEWLKVQEVCQEDYDNVEVSILDVKKEELQYDFERNLYDISSSDFFKKVYVSEFDQYGGEPYGAILGL
YNFENTTNDIIWLTGMGMVAKNSHAPFIASIDKSFFGVKDLSEITHIKSFEALLEHPRYKEWNDFRNLDVAAYIG
LTVGDFMLRQPYNPENNPVQYKLMEGFNEFVDYDKNESYLWGPASIHLVKNMMRSYDKTRWFQYIRGVESGGYVK
NLVACVYDNKGILETKSPLNVLFADYMELSLANIGLIPFVSEKGTSNACFFSVNSAKKVEEFVDGFDSANSRLIA
NLSYTMCISRISHYIKCVIRDKIGSIVDVESIQKILSDWISEFVTTVYQPTPLEMARYPFRNVSIEVETIPGKPG
WYSCKINVIPHIQFEGMNTTMTIDTRLEPELFGTNNNDQNATGGDQNATGGDQNATGGDQNATVD

FIGURE 13: SEQ ID NO: 4
MKKIWLALAGLVLAFSASGTDQNATGGDQNATGGDQNATGGDQNATGTMNIRPLQDRVLVRRAEEEKKSAGGIIL
TGSAQEKPSQGEVVAVGNGKKLDNGTTLPMDVKVGDKVLFGKYSGSEVKVGDETLLMMREEDIMGIIADQNATGG
DQNATGGDQNATGGDQNATVD

FIGURE 14: SEQ ID NO: 5
MKKIWLALAGLVLAFSASGTDQNATGGDQNATGGDQNATGGDQNATGTMGKIIGIDLGTTNSCLAIMDGKTAKVI
ENAEGHRTTPSVVAYTDSGEILVGQAAKRQAVTNPDNTFFAIKRLIGRKYDDKAVQEDIKKKVPYAVIKADNGDA
WVATKEGKKMAPPQVSAEVLRKMKKTAEDYLGEPVTEAVITVPAYFNDSQRQATKDAGKIAGLEVKRIINEPTAA
ALAYGVDSKKGEQTVAVYDLGGGTFDISIIEIADVDGDNQIEVLSTNGDTFLGGEDFDLALMNYLIDEFKKEQGI
DLHNDKLALQRVREAAEKAKVELSSAQQTDVNLPYITADATGPKHLNIKVTRAKFESLVSDLVMRSLEPCKKALE
DAGLSKSDITEVLLVGGQTRMPLVQEKVKEFFGKEPRKDVNPDEAVAVGAAIQGGVLAGDVKDILLLDVTPLSLG
IETMGGVMTKLIERNTTIPTKKSQVFSTAEDNQPAVTIHVLQGEREMASANKSLGRFDLADIPPAPRGMPQIEVT
FDIDANGILNVSAKDKATGKEQNIVIKSSSGLSEEDIEKMVQDAEANAEADKKFHDLVTARNTADNLIHSSRKAI
QELGDKVTAAEKEKIEEACKELEAATKGDDKQAIESKTKALEEAFAPIAQKAYAEQAQAAVAQGGAKAEEPKKEE
DVVDADFEDVEDDKKDQNATGGDQNATGGDQNATGGDQNATVD

FIGURE 15: SEQ ID NO: 6
MKKIWLALAGLVLAFSASGTDQNATGGDQNATGGDQNATGGDQNATGTMAAKQVLFSDEARAKMLDGVNTLANAV
KVTLGPKGRNVVLDKSFGTPTITKDGVSVAKEIELEDKFENMGAQIVKEVASKTADVAGDGTTTATVLAQALLTE
GLKAVAAGMNPMDLKRGIDKATARLVEELKALSKPCSDPKSIEQVGTISANSDATVGKLIADAMAKVGKEGVITV
EEGKGFEDELDVVEGMQFDRGYLSPYFATNQENMTTDLENPYILIVDKKISNIRDLLPILEGVSKSGRALLIIAE
DVESEALATLVVNNMRGVVKVCAVKAPGFGDRRKAMLEDIATLTGATFVSEDLSMKLEETNMEHLGTASRVQVTK
DNTTIIDGAGEKEAIAKRINVIKANIAEANSDYDREKLQERLAKLSGGVAVIKVGAVTEAEMKEKKDRVDDALHA
TRAAVEEGIVAGGGVALIRAQKALDGLTGENDDQNYGIALLRKAIEAPLRQIVSNAGGESSVVVNQVKANQGNYG
YNAANDTYGDMVEMGILDPTKVTRSALQHAASIAGLMITTEAMIGEIKEAAPAMPMGGGMGGM
PGMMDQNATGGDQNATGGDQNATGGDQNATVD

Figure 16A: SEQ ID NO: 7

*Francisella* O-antigen biosynthetic polysaccharide

```
ATGAATTATCATATAAAAGAAGTATTCTGGTCAATTATTTTATCATTCTTAAAATCACAA
AAAGGTATACATACCAATGATGAAGCCAAATTAAGATTGTTTATTGAAGCTGTATTTTAT
GTGTTACGTACAGGCTGTCAATGGAGAATGTTACCATTTTATTATGGTAAATATAGATCA
ATACATAAGCGTTTTAAAGATTGGTGTGATAAAGATATATTTTCTAGATTATTTAAATCA
GTACAAAACCCTGATTTACAAGAAGTCATGCTTGATTCAACAATAGCAAGAGCACATGCT
TGTGCTACGGGATATGATAAAGATGATAACCAAGCAATTGGTAGATCAGTTGGTAGGATA
ACCACTAAAATCCATGCTATGACTGATGCTTTAGGTAATCCAATAGAAATATTGTTGTCA
GAGGATAAAACTCATGATAGTAAAGTAGCTATAGATTTACTAAAAAATGTATATAATACA
AAAGTTATCGCTGATAGAGCATATCATTCTAATGAAATCAGGCAGCATATTCAAGGTATA
TCCTCTGAAGCTGTTATCCCTTGTAAATCAAATACTCTAAACCATATACCTTTTGATAGT
CATGTATATAAAGAAAGACATTTGATAGAGAATTTCTTTTCTAAAATTAAGCATTTTAGA
AGAGTATTCTCTAGATTTGATAAAACCATTTTAGCATATATAGGAATGATTAAATTAGCT
TGTACTTTTATTTGGTTACGATGAATATTTATTTTTGTGCACAGAACCTAATTTGCATTT
TTGTGCACAAAGAAAATTTTTTTGATATAATAGACTTTAATAGGATATTTTCTAAAAATT
AACAAATGTCTTTCTACGATAATAGAACGCTTAATTTCGTGGTAATAATAGTTTTAACTA
TTATTACTGTTAATTGGACTTTCTATATTTTCAAGCAAGATGTTAATTTACATTTTTTAC
TTGCATTAGTTTTGCTGAGATGCTTGTCATCTTTTTACTACTTAGAGATTATATGGCTA
GTTGGCGTAAGTCGACTCAAAAAACTTTTTTACGTAAGGCTTTTATTAATTTGCCAGTAT
TTTTCATAGTGGCATTATTTTTTATGGCAAAGTCACTTTTTCGTTGATATTCTCTGAGT
TTTTATTTTATGTTTTTTTGATCAGTTTAAGTGTCTACTTTTATTGGTATTTGATGAACA
GAGGATCAGTGGATAAAAGTAAAACTGCGGTTATTTATGGTGCAGGTGCTGCAGGAACAA
AGATTGCTCAAGAACTTGCTTCTGCTGGTTATCGCATCAAATGTTTTGTTGATGACAATG
AAACTTTACAAAAAGAAGTATTGATAGTAAAAAGGTTCTATCTAAAGCTGAATTAACAA
AACTATTGCTATCTAGTAGATTTGACCTTTTGGTTATTGCATTGCCAAGAAATGCAAACC
AAGTAGTCAAAAATATATATAAAGAATTTGAAAAGGATTTTAATCAGATTAGAATTATGC
CGCCTCTTGAGGAAATTCTTCAAGATGAGAATTTTATGTCACAGTTGAAGCCTGTTTCAC
TCTATGATCTATTAGCGCGTGATACTAAGAGTTTAGATAAAGAATCTATCTCTAATTTTA
TCAAAAATAAGGTGGTGCTAGTCACAGGAGCTGGAGGTAGTATAGGTTCTGAAATAGTAC
ATCAATGTATCAAGTATCAGGCAAAAGAGTTGATATTGGTTGATCATAGTGAGTTTAACT
TATATAAAATTACTGAGGAGTGTAGTCATTTTAATATCAATAGTGTGCTATGTTCTGTTT
GTGATAGAAAAGCATTGGCTGAGGTTTTTCAAAAGTATACTCCAAATATAGTATTTCATG
CTGCTGCCTACAAGCATGTTCCCTTAGTTGAGGAGAATATCTCTAGAGCAATTAGAAATA
ATATCTTAGGTACTAAGAATGCTATAGATCTGGCTATAGAAGCTGGTGTTGAGTCATTTA
TATTGATTTCCACTGATAAAGCAGTGCGACCAACGAATGTTATGGGGGCTACCAAGAGAG
TTTGTGAGCTGTATTTACAGAATGTTGATCCCAAAAATACCAAGCTTGCTGCAGTGCGTT
TTGGTAATGTGCTTGGTAGTAGTGGCAGTGTGATTCCAAAATTTGAAGAGCAAATAAGAA
AAGGTGGTCCTGTTACAGTTACTCATCCTGAAATTACACGTTATTTTATGTTGATACCAG

AAGCTTGTGAACTGGTCCTACAAGCTGGTGCTATTGCAAAAAATTCAGAGGTCTTTGTCT
TAGATATGGGGCAACCTGTCAAGATTATTGATCTTGCTAAACAATTTATTAGACTTTCTG
GTAGAGGTGATATTGATATTAAAATAGTTGGTTTGCGTCCAGGAGAGAAACTTTACGAAG
AGCTTTTGATAGAGGAAGATGATGTTAGTACCGACTATAAAGATATTTTATTGGTAGAA
GGACTTTTTACGATATTAATACTCTAAACCAAGATATTGAATCGTTGATCAAGGATGATG
TTGATCAGCTTGTGATATTAAAGAAATTGTTCCGGAATTTGAACATAGATTGAATGGGT
AGTGGTTTATGTTTTATGAGGTTTTAAAAGATTGCTTGATATTTTACTTTCTTTTATG
GGGTTGTTGTTATTAAGTCCTATTTTCTTAATTATTATTTTATGATAAAGAAAGATTCA
AAAGGACCTATATTTTTTAAACAAAAGCGCTATGGTAAAGATAAGCAATTTTTTTACATA
TATAAGTTTAGAACTATGTATGTTGATACTCCAAAAGATATGCCAACGCACATGTTACAG
GATCCATCGAAATGTATAACTAAGGTTGGAGGATTTTAAGGAAATCATCTTTAGATGAG
TTGCCACAAATTATAAATATTCTAAAAGGTGAAATGAGCATCGTGGGTCCAAGACCAGCA
TTATGGAATCAAGATGACTTAATAGCACAAAGAGATAAGTATGGGGCAAATGCTGTGCCT
GTGGGACTGACTGGCTGGGCACAGATTAATGGTAGGGATGAATTACCAATACCTGATAAA
```

Figure 16B: SEQ ID NO: 7 (Continued)

```
GCTAAACTTGATGGTGATTATGTAAAAAATAAAAGTACATGGTTTGATTTAAAATGTATT
TTTTTGACAGTATTTTCTGTTTTTGCCAAAAAGGGCGTCGTTGAGGGTGGTACTGGAGCT
TTAGGTAACAAAGAGGATTTAAAGTAGTATGAAAAAAAGAATCTTAGTTACAGGTTTGAG
TAGCTATATTGGTAACTCATTTGCGGCTAAATATAACTCAGATTTTAGTATCGATAAAAT
ATCTTTGCGCGATGTTTCGTGGGCAAATATAGACTTAAGTGGTTATGATGCTGTATTGCA
TGTCGCTGGAATTGCCCATACTTCAAAGGATCCTAAACTAAAAGAAAAATACTATAAAAT
AAATACGCAATTAACTTATGATCTGGCAAAACAAGCTAAAGATCAAGGTGTTCGACAGTT
TGTGTTTTAAGTAGTATTATAGTTTATGGTGATAGTGCGCCAATAGGTCAACAAAAAGT
TATAACTAAATATACCGAACCTAAACCAGATGATTTTATGGAGATAGTAAGCTTCAAAC
TGAAATTAAGCTAAATAGCCTGGCTAGTGATGACTTTAATATTGCTATAATCAGACCACC
AATGGTATATGGAGAAGGCTCAAAAGGCAACTATCCAAAGTTGGTTAAACTTGCAAAGTA
TACTTTTATTTTTCCTAATATTAATAACCAAAGAAGTGTTATATCTATAGATAATTTATC
TAAAGAGATTGCAGAAATAATTTTGCAAACTAAACATGGAGTTTTTCTACTTCAAGATAA
TGAATATTTTGCACTTCACAGTTTATAAAAAACTATAGAAAAGATGTTTTAGGTAAGAG
AACTTATCTGACAAAAATTTTTAATCCAATTATAAGATTGCTTGCTAAAAAAGTAGATTT
TATTAATAAAGTTTTTGGGAATTTGACTTATGAGAAGTAAGTTATTATTCATAGCTAATG
ATTTTGATATTGTAATATATCGTTTCAGAAGAGAAGTAATCGAGTCTTTTGCTGCTAAAG
AGTATGAGATAGTACTAGTAACACCCATATTCTAAGAAAGCAGAGGTTTTTTGTAAAAGTC
TTGGTGTTAAGTATATAAATGTTGATATAGATAGACGAGGCAAAAATCCTTTTAAGGATT
TGCTTCTTTTATTTAACTATTTCAAAATAATAAAAAAAGAAAAACCTGATTACATTTTTA
GCTATACAATTAAACCAAATTTGTATGTTGGGTTAGTGAATTTGTTTTTTAGGAAGAAGT
TTTATCCAAATGTAACAGGCTTAGGAAGTGTTTTTGCTAATCATGGTATTGTTCAGAAGT
TTATAATATCTTTATATAAGTTATCATTTAAAAGCACCACAAAAGTATTCTTTCAGAATG
AGCAAAATAAAAAGTTATTTATAGCTAAGAAAATAATCAGTGGAGAAAAATCAATATTAT
TACCAGGTTCTGGGGTAAACTTAGATGAAAATAAATATGTTGACTATCCTAAAGACCAAG
GAATATTAAAATTCGTTTTTCTTGGCCGAATAATGAAAGAAAAGGGGATTTATGAATTGT
TAGAAGCCTTTGCTATACTTGAGAAAAAATATAAAAATATTAGTCTTGACATTTATGGTT
TTTGTGATGAAAATAAATCTAATTTTATGGGAAAGGTTAATACGATAAAATCAGTAAAAT
TTTATGGTTTTACTGATAATACTAAAGAAAAAATAGCTAGTGCACATGCAGTTGTTTTGC
CATCTTACCATGAAGGAATGTCAAATGTGCTGTTAGAAGCAGCTGCGATAGGTAGACCTG
TAATTGCGTCAGATATTCCTGGGTGTAGAGAAATTTTGATGATGGTCTCTCTGGCTTAT
CATGTAACCCTAATGATGTGAGTTCTTTACGTAACTCATTAGAGCAGTTTATAAATATGT
CGTATACTGATAAAATAGCTATGAGCTATAAAGCTAGAGCTAAGATAGAAAAGATTTTG
ATAGAAGTATTGTTGTCAATGCATACTTACAGCAAAATTAATAATAAGGGTTTAAATTAT
GAGTTTATATGAGGATATAGTCGCTAAAAGAGAAAAGGTTTCATTGGTTGGCTTGGGTTA
TGTTGGTTTACCAATAGCTATTGCATTTGCAAAAAAAATAGATGTGTTAGGATTTGATAT
TTGTGAAACAAAAGTTCAACATTATAAGGATGGTTTTGATCCAACAAAAGAAGTAGGAGA
TGAGGCTGTCAGAAATACGACAATGAAATTTAGTTGTGATGAAACAAGTCTTAAAGAGTG
TAAATTTCATATTGTTGCAGTTCCTACACCAGTTAAAGCAGATAAAACTCCTGATTTGAC
GCCGATTATTAAGGCAAGTGAGACGGTTGGTAGGAATCTTGTCAAAGGCGCTTATGTTGT
GTTTGAATCAACTGTTTATCCTGGTGTTACAGAAGATGTTTGCGTACCAATACTTGAAAA
AGAGTCTGGCTTGAGGTCTGGTGAAGATTTCAAAGTTGGTTACTCTCCTGAGAGGATAAA
TCCTGGTGATAAGGTTCATAGGTTAGAAACAATTATCAAAGTAGTATCTGGTATGGATGA
AGAGTCTTTAGATACTATAGCAAAAGTTTATGAGCTAGTAGTAGACGCAGGAGTTTATAG
AGCTAGTAGTATAAAAGTGGCTGAAGCTGCTAAGGTTATAGAAAACTCTCAAAGAGATGT
TAATATAGCTTTTGTTAATGAGTTATCGATAATATTTAATCAGATGGGTATTGATACTCT
AGAGGTTTTAGCAGCAGCTGCAACTAAATGGAATTTCTTAAACTTTAAGCCTGGTCTTGT
TGGTGGACATTGTATTGGTGTTGACCCATATTACCTAACGTACAAGGCAGCTGAGCTTGG
ATATCATTCTCAGGTAATATTATCTGGTCGTAGGATAAATGATAGTATGGGTAAATTTGT
AGTTGAGAATTTAGTCAAAAAACTGATATCTGCAGATATACCTGTTAAGCGAGCTAGAGT
AGCAATTTTCGGCTTTACTTTTAAAGAAGACTGTCCTGACACTAGGAATACTCGAGTTAT
AGATATGGTAAAAGAGCTCAACGAGTATGGTATAGAGCCATATATTTATAGATCCGGTAGC
TGATAAGAAGAGGCTAAACATGAGTATGGACTTGAGTTTGATGATCTAAGTAAAATGGT
CAATCTAGATGCGATCATTATTGCTGTTAGTCACGAACAGTTTAAAGATATAACAAAGCA
ACAGTTTGATAGGCTATATGCGCATAATTCTAGAAAGATTATATTTGACATCAAAGGTAG
TTTAGATAAATCTGAGTTTGAAAAAGATTATATTTATTGGAGATTGTAGTGGCTTACGAT
AATGTTAAATTTCCTCATGGTTCGTTTTTTTTGGTGACTGGAGGTGCGGGTTTTATTGGC
TCTAATTTATGTGAAGTTTTACTTAGTAAGGGTTATAGAGTTAGGTGTTTAGATGATCTC
```

Figure 16C: SEQ ID NO: 7 (Continued)

```
TCAAATGGTCACTATCACAATGTTGAGCCGTTTTTAACTAATTCTAATTATGAGTTTATA
AAAGGTGATATTAGAGATTTAGATACTTGCATGAAAGCTTGTGAAGGTATTGATTATGTT
CTACATCAAGCTGCTTGGGGAAGCGTACCAAGAAGTATTGAGATGCCATTAGTGTATGAA
GATATAAATGTTAAAGGTGCATTAAATATGCTTGAAGCGGCTAGACAAAATAACGTTAAA
AAATTTGTCTATGCTTCTAGTTCATCAGTATATGGTGATGAGCCAAATTTACCTAAAAAA
GAAGGTAGAGAAGGAAATGTTTTATCACCCTATGCATTTACAAAGAAAGCTAATGAAGAG
TGGGCGAGACTATACACAAAGTTATATGGTCTAGATACTTATGGTCTAAGATATTTTAAT
GTTTTCGGTAGAAGACAAGATCCTAATGGTGCGTATGCAGCAGTTATACCTAAATTTATC
AAACAGTTATTAAATGATGAAGCGCCAACTATAAATGGAGATGGTAAACAGTCGAGAGAT
TTTACATATATAGAGAATGTTATTGAGGCAAATCTTAAAGCATGTTTAGCAGATAGTAAG
TATGCCGGAGAGTCTTTTAATATAGCTTATGGAGGTAGAGAGTATCTTATAGATTTGTAC
TATAATCTTTGTGATGCCTTGGGTAAAAAAATAGAGCCAAATTTTGGTCCAGATAGAGCG
GGTGATATTAAGCATAGTAATGCTGATATTTCGAAGGCTAGGAATATGCTCGGATATAAT
CCGGAATATGATTTTGAATTAGGCATAAAGCATGCTGTTGAGTGGTATTTAATTAATTAA
ATGGTATTTTAATCAAGTGTACATAAAAAAAGTGTCTTTTAAAATTTTATATTTATATTT
ACTAGCTTTTTGTATTATTTTTAGTTTAGAATTTAAATTTGCTATATTGAATATTATAGT
TTATCTTCCGGCTTGTATTTTGGGTTTTTTAGCTCTTAAAAAACTATTTGTCGGAAATAT
TGTTAAGAAACAATTAGCTTTCCTTTTTTCTTTTCTTTTTATCAATGATTTATTTAAT
AATAGTCCAAATAATCTTACTTGATGCAGCATCATTGTTTCCTCAGTTTTTATTTAACAT
TTTGATCGCGATAGGTTTTTGTAACTTTATTTTTGTTTCATATGATAATAATGAAAATTA
TTTTTTTAATATGTCTAAAATAATATTTTTTGTTACTTTCTTACAATCTATTTTTGTATT
TCTTTCAAGGTATTATATATTTTTAAATGATTGGATATTCTTTTTTTTAGTGAAAAAAGG
GAATATTGAGATTTCGAATGTTATTGAATATAAGTTAAGAGTATTCGGACTTAGTAACGC
TGGAGGGGATGGTTTAGGATTTTCAATTACTATAGGATTATGTTTTTCTATATTTATTT
TATCAAATATATTAAAGGTAAATCTATATTTACCAAACTTATGCTGTTTGTACCTTTAAT
TCTTATTGTGTTTCTAATATTTTCATATCTAGAACATCACTCTTAACTTCTTCACTTAT
ATTGTTAATAACAATATTTTATATATATATTAAAAAAGAAAAATTACTGTTTATTATAAT
ATTGGCGCTATTCTTTTTATCAATATGGATATTGTTCAAATTAAATTTGAATTTGAGTTG
GGCTTTTGAAAATATTTACTCGTACATTCAATCTGGCGATTTTTCACATGGAAGTCTAAG
TGTTTTAATCAATAAAATGCTTTTTGTGCCAGATAACCTTTTGACTTGGATATTTGGTTG
TGAGGATGTTAGTAATACTGATATTGGTTATATTAAATATTTATACTATTATGGGATTAT
ATTTAGTATGTTTTTTTATATTCTTATTATTTTCTTGTACTTTGAAATGAGAAAATGTTT
TATATTTTCAGAGTATCGATCATTATTTCTATTGTTGTTAATAGTATGTTTAGTTTTTCA
AGCAAAAATAATTTTTTTGACAGTAGGATTATTTACTAAATTAACCATTATATTATTTAT
TTTTTCTCTTAAAGAAAACAGCTTTACAACTAGGAGTGTGATTGAAAAGGTTTGTACAT
TTAATAATAAACCTTAACCAAGGTGGTGCTGAAACAATGCTTTATAAACTTTGCAAATCT
ATGGATAAGTCAATATATCATATTACGATTATATCACTTATGGGTAGGGGAGTATTTGCA
AATAAGTTAGAAGCTTATGGTGTTAAAGTTTATACATTAAATTTAAATAAATTTAATGTA
CTATTTGTATTGTTTAAATATATTAAGATTATCAGAAGAATAAAGCCTGATGTTATTCAT
GCTTGGATGTATCATGCAAATGTAATTTCTATATTATGCAAGCCTTTTTATAGAAAGACT
AAATATATAAATAGTATAAGAATGGATTGGAGAATTATGATGGTCATAAGAATCTTACA
AAGTTTATGATAAAGTTGAATGCAAAATTTTCTAAGTTCTCAGATTTAACATTAAATAAT
TCAAAGAAATCATTAGAAGATCATCAAAATATAGGTTTTAAAAACCAATGCTTTATAGCA
AATGGTTTTGATAAAGATGTTTTTAAACCGAGCTTTTTAAAGTATGAAAAATTTCGTTTA
AATAATGATTTAGATGATAATGTTAAAATTATAGGTATCATAGCAAGAAATCATGCTGAT
AAAAATATTTCTCGTTTCTTACAAATAGCTAATTTATTGTTAAAAAGTAATCCTAGTTTA
GGTTTTTAATTGCTGGAAGAGAGTGTTCGAAAATAGATATAGGTAGTTATCTAGATAAC
AAAAGTAATGTAAATAAGTTTTTTGTATTTGAATCTGTGGATTCTAGTGAATACTTACCA
GTATTAGATTTATATTTGTCTACATCAAAAGTTGAAGGTTTTCCAAATATACTTGCAGAA
GCCATGCTATGTGAAGTTCCTATTGTTGCTTCTAATGTTGGAGATTGTAAAGATATACTT
AATGGATACGGTGAAGTTTTTGAGCTTAGTCAAGGTAATAAAGAAATAATAGAAAAGATT
ATGAAAGTTTTAGAAACAACGGTAGTCATGAAAAGCGCATGAGAGAATATATAATAAAT
AATTTTAGTATAGAAGCTATTTTGGAAAAACACGAAAAACTTTATCATGAGGGCAGTGTC
TAATGTGTGGAGTAGTAGGCTTTTACTCATTTAATAAAGAAGAAGGTTTTGACTCAATAA
TTAATCAATCATTGCTTTCTATAAAGCATAGAGGGTCGGATGATAGTGGGTATTGGTGCG
ACAATCAAGTTACTCTGGGGCATACTAGATTATCAATACACGATATAACTAATGCGGGAC
ATCAGCCAATGTTATCTAATAGCGGTAATACTGCTATTGTGTTAATGGAGAAATATATA
ATTACTTATCCATAAAAAATCAGCTATTAAGTGAATATTCAAATCTTAAATTTAAAAGTA
ACAGTGATACTGAGGTTTTGGTCAATGCTATTGAACTTTGGGGTATAGATAAAACTTTAG
```

Figure 16D: SEQ ID NO: 7 (Continued)

```
AAAAATGCATAGGAATGTTTGCTTTTGGAGTTTACAGTAGAAAAACTAGTTGCTTAATAC
TAGCTAGAGATAGATTTGGCGAGAAGCCATTATATTTTGGTATCCAAAATGGTATTTTGG
GTTTTGCATCAGAATTGAAGGCACTTAAGCCATTAAAGGAATGTGGCTGGAGGTTTGATA
TAGATAGAGATGCTTTAGCAACATATATGAGGTATGCTTATGTACCAACACCATACTCTA
TTTATAAAAATATATCTAAACTAAATGTAGGTAGTTACATAAAATTTGATGCTAAAGGTA
ATAGTAAGAGTATAAATATTGGGATTCTAAAAAGTACTAGATTCAGAAAAATATAAAG
ATTCGTATGATCAAGCAATCCTAGATTTAGAAATTAAGCTTAAAAGTACACTATCAATAC
AAATGCAGTCAGATGTTCCTCTAGGAGCATTTTTATCCGGAGGAATTGACTCAACAACTG
TAGTTGCTCTTATGCAAAGTATGTCTAAAGATAAGATAAACACTTTTAGTATAGGTTTTA
ATCAAAAAGAATATAATGAAGCTGAGCATGCAAGAGCAGTAGCAAAACATATAGGTACAA
ACCACACAGATATGTATGTTACAGAAAGAGATGCTCTTGATGTAATACCAAAACTTGCTG
GAATATATGACGAGCCCTTTGCTGATTCATCACAAATACCAACGTATCTTGTGAGTAAAA
TAGCTAAGTCGAAAGTAACAGTTGCACTATCAGGTGACGCTGGTGATGAGCTCTTTGGCG
GTTATAATAGATACTTTTTAGCACCAAATATTGCTAAAAAAATCAAATTTGCTAAGTTAC
TTAAATATGCACCAGATGCTTGGATAAAAAAAGCTGAGATATTAAATTTTGGTAAGTTCG
CTTTATTAGCAGATAAACTACTAAAACTAAAAGAGTTCTCGAAAAAGCAAAAACAAATA
AAGAGCTTTATGTACTACTTTGTTCACAAATAAATGATACTAGCTTTGTGTTAGGAGCAA
AAGAGTATGATATATTAAGAGATAAGAATATTTATGATATTCCACAATTATCTTTCCAAG
AGTGGATGATGTTTGTTGATTCTAATACATATATGATAGATGATATATTGGTTAAGGTTG
ATAGAGCAGCTATGGCTAACTCTCTAGAGACAAGAGTGCCATTTTTAGATCATAATATTT
ATGAATTTGCTTATTCCTTACCAATTGACTATAAAATACAACGAGGTAACGGAAAAAGAA
TTTTGAAAGATTTGTTATATAAATATGTGCCAGAAAGTTTGGTCAATAGGTCTAAGATGG
GGTTTGGTATTCCGCTTGCTAAATGGTTAAGAGAAGATTTACGAGAGTGGGCAGATAATT
TACTGGATTATAGTAAAATAGACAAGCAAGGTTACTTAAGTCCTGAGGTGGTGCAAAAAT
ATTGGCAAGAGCATTTGAGTGGTAAAAGAAATTGGCAAGCAATATTATGGAATATTCTAA
TTTTTCAGGAGTGGTTAGATAATGAGTAAAGTAAATGTAACAAAACCATACTTACCAGAT
ATAAATAAATATAAAAGCTATGTAAATAAAATATACAAAAATGGATGGCTTACTAATAAT
GGTCCGTTAGTGCAAGAGCTAGAAAAAAGACTTGCAAAGTATCTAGGTGTTAAAAATATA
GTTTTAGTATCAAATGGTACAATTGCATTAGAAATCGCGTATAGAGCGTTAGGAGTCAAA
GGAAGTGCAATTACTACTCCATTTTCATTGTTGCTACTACATCTTCATTGGTTTCTAAC
AATGTAAAACCAGTGTTTGTTGATATTGATGAGAATACTCTAAGTATAGACGTCTCTAAA
ATTAAGTATGCTATTGAAGAGGATACTTCAGCTATTGTGCCAGTTCATGTGTTTGGAAAT
GGTTGTGAAGTTGAAAAAATAGACATGCTGGCTAAAAAACATAACTTAAAAGTTATTTAT
GATGCAGCACATGCTTTTGATGTTAAGTATAAGGGTGAGAGTATATTAAACTATGGTGAT
ATTTCGACATTAAGTTTTCATGCAACAAAGATTTTTCATTCTATTGAAGGAGGTGCGCTT
ATCATTAATGATGATAGTCTTGTTGAAAAAGTTCGTTATTTCATTAATTTTGGTATAGAA
AGCTCAGAATCAATACCTTACTTAGGTACTAATGCTAAAATGAATGAATTTGAGGCGGCT
ATGGGACTTTGTGTTCTAGATGATATTATAGAAATTAAGAGCAAAAGGAAAGTTATTACA
GAGATATATGAGGCTGGGTTAGATGGATTGGTAAAGTTTCAAGAACAGAATCAGCATTCT
AGTAGGAATTATAGCTATTTTCCAGTAATATTTAGGACTGAGGAGGAACTTCTCAGAGTA
CAGAAAGCACTAATACAAAATGATATAATATCGCGTAGATATTTTATCCATCATTAGAT
AGTCTTAGTTATATAGAGCCAAAGCAGTATATGCCAATCTCAAGAGATATATCTAAAAGA
ATATTATGTTTGCCAATTTATGCAGAGTTAGAAGACGATAAAATTAATAAAATAATTAAT
AATATCAAGAGGGTTTCCTCATGAAAAAAATATTTGTTGTTACAGATAATAGAACTATTC
TAAGTGATTTTAAAAATATCATTGGTAGTAAAAATGATGTAGAGGTTGATTATTTTTGTA
GTTTCAAGAGTCAAACTTCTTTTGCCAAAGAAATATATAACAGTGAGATTAAGCCAATAG
ATATGAAAAAAAATGGCAATGATCTTATTGGTAAGTATGATTAGGITTTTCTTGTCATT
CGAAACAATTATTTCCAGCAAAATTAGTTAATTCAGTATTATGTATAAATATTCATCCTG
GACTTAATCCATATAATAGAGGGTGGTTTCCACAGGTCTTCTCTATTATAAATAAACTAC
CTATAGGAGCAACTATTCATGTGATGGATGAAGAGATAGATCATGGAGATATAATCATTC
AGGAAGAAGTTGAAGTTAATTCTTTCGAAAACTCTTTTGATGTTTATGCTAAAGTTCAAA
AAAAAGAAGTTGAGTTGTTCACTAAAGTCATAGATGATATTTTGAATAATAAGTTCACTC
GAATCAAACCTAACTCCGAAGGCAACTATAATTCAATTCATGATTATAAAAACATGTGTG
AAATTGATTTAGATAAAATAGTAACAATGCGGGAAGCAATTGACTATCTAAGGGCTATGA
CACACCCTCCATATAAAAATAGTTATTTCATTGATGAGCATGGAAATAAAGTATTTGTTG
CTCTTGAACTTGAAAAGATAAGTTAGAAAAATGAGCCTTAAAAAAATACAATATCAAAT
TATATAACACAACTATATACTAGCTTAATTGGTATTGTTATACTTCCTTTGTATTTACAA
CATTTAAGTCATGATGCATTTGGTCTGATTGGTTTTTTTACAGTTTTCAAACGTGGTTA
CGGTTGTTGGATGTTGGTATAACACCAACTTTATCAAGAGAAGTGGCTCATGTTAGAGGT
```

Figure 16E: SEQ ID NO: 7 (Continued)

```
AGTACTGATGACTATCATTACTTACGCAAGTTGGTTAGATCGTTAGAGCTATTTTTCATT
ATTGTTGGTGTTCTGGTATTTATTGTAATTAGTACACATTCAAGGTATATATCCACCTCT
TGGTTACATATAGGCTCGCTAGATGCTGATAGTGTAAGTGTATGTATTGCACTTATGGGT
TTAATGTTTGCATTAAGATGGGTGTCTGATCTATATGGTGGTGGTTTGCGTGGCTTTGAA
AGACAGGTTCTTTATAATAATTTAAGTATCATACAAACGACACTACAGTTTATTGGTGGA
TTATTATTTATCTGCTATGTGTCTACTAATATTATGTATTATTTTGTATATCAGACAATA
ATTGCGATACTATATCTAGTATGTATTGCAATTGCATTTTATAAAATACTACCATCATCA
TTTAGCGTGGGTTTAAGGTTTGATTTTAAAATAATTAGAAAAGTGCTTCCATTTGCACTA
GGCATTGCATATTCTACAACAGTTTGGATTATTGTCACTCAATCTGATAAATTAGTGTTC
TCACATGTATTACCATTATCTGAGTATGGTTATTTATCTTTATTGATAGTGATATCTAGT
GCTGTTACGATATTGTCCTCTCCGATTAGCATAGCTATTCAGCCTAGAATGACAATGCTA
TTAGCCCAACAAAATGTAAAAGGAATGGAAAGCTTATATTTAAAATCATCCTTGATCTCA
ATTACTTTTTATCTGCTGTAGTAACATGTGTTTTGATGTATTCTCATCAGCTGTTGCAG
TCATGGACAGGAAGTATGGAAATTGCTAATTGGGGTAGTAATATCTTAAATATATATGTT
TTATCAGCATCTATTATTTGTATAATATCATTTCAATATTTTTACAGTATGCTTATGGT
AAGTTAAAGCTACATAATACATATAATACAATTAGTTTAGTATTTTTGCTCCTATAGTT
ATATATACTGCTTATAATTATGGAGTGTATACTACAGCACTATTATGGCTTGGATATGCT
ATAGTGGGGCTGATAATCTGGATGCCTATTGTACACCATGTATTTGCTAAAGGTATCAAT
AGGTATTTTTTATAAATTTAGCAGTTATTACTATAGTATGTTTTTTATTATCGTTAATA
TTAAGGGTTGGTATATTTATCCAAGTAAAATTGGGTTGGTAGAATTAATATTGATTGGG
TTTGCATTTTATTTATACAAATTTGTATAGAGTATGTTTTGTTTCGGTACAAGGTTTTG
AGGTGTATAGATGATTAAAGTTTCAGTATGTGTGATGACATACAATCAAGAAAAGTATAT
TGGTCAATGTTTAGAGTCTTTGGTTACTCAAGAGACTGATTTTGACTTTGAGATAATCGT
TGGAGATGATTTTCTACAGATGGTACAAGAGATGTTATTCAAGAGTATCAAAAAAAGTA
TCCGGATATCATAAAGCCAGTTTTTAGAGATAAGAATGTGGGAATTACTGAAAATATTAA
AGAAATCTATTTTGTTGCAAATGGTGAGTATATAGCTCATATGGATGGTGATGATTATGC
ATTGCCTGGTAAACTTCAAATTCAGGCTGATTTTTGGATAATAATCCAAGATGTACGGG
AGTTTTCATAATATAAATATACTCTATCCAAATGGTAATATACAACATAGTAGGTTTGC
TTGTTCAAATAAGAGTATATTCAATTTATCAGACACTTTACGCGGAGTTGCTGTTGGTGC
AAATAGTTCAAAAATGTTCAGAACATCGGTTTTGGATGATTTGATTTTACCGGATATAGA
GCTTCTAGATTATTATTTTCATGTTATAACAGCAGAAAAGGTTATTTAAGTTTTTTAAA
TTCTAATGAATCCTATAGTGTGTACAGAAAAGGTATTGGTATCACATCTAAGTCTAAGGA
AAAAATCTATAATACTTATGCTGGATTATTTGAATATTTTTTGGATAGATATCCTGAAGA
GAAATTAAATATTTGTATCCCTGTTGTGCAAATGATAATTTCGGCTATTAAAGGGAGATG
TTTTATTAGTGCTATTCGTCTATTCAAAATTTTAATTAGATCAAGATGTATTCCATTAGT
AAGTTGGTTTAAATATAGATTTGAAAAATAAATATCATTTAGAGGATTATGTGAAATGAA
GGGAATAATTCTAGCTGGTGGCAGTGGTACAAGGCTATATCCACTTACCTTGGGTGTTAG
CAAACAGCTGCTACCTGTTTATGACAAGCCATTGTTATACTATCCACTATCTGTGCTTAT
GCTTGCAGGTATTAGGGAGATATTAATTATCTCTACAGTGCGTGATATCTCACTTATCCA
AGAGCTTCTTGGTGATGGTTCACAATTTGGTATACAGTTGAGTTATAAAATCCAGCCATC
ACCAGATGGGCTTGCTCAAGCATTATTCTTGGTGAGGAGTTTTTGGCGGGTGACTCAGC
TTGTTTGATATTAGGAGATAATATCTACTATGGTCAAGGTATGACTACAATGCTAGAGTC
TGCAAGAGCACAGTGTGGAGGTCCAGCTGGTGGCGCTTGTGTTTTGGTTATTATGTTAA
TGATCCGCATAGATATGGTATAGTCGAATTTGATAAGCAAAAAATGTAATTTCGGTAGA
GGAAAAGCCACAGAATCCTAAGTCACACTATGCTATCACAGGTTTATATTTTATGATAA
TAATGTTGTTGAGTATGCTAAACAAGTCAAACCATCTGCACGTGGTGAGCTAGAGATTAC
TTCACTTAATGAGTTATATCTAAAAGAAAATAAGCTAAATGTCGAACTCTTAGGGCGTGG
CTTTGCTTGGCTTGATGCTGGTACGCATGATTCATTGCTAGAGGCAGGTCAATATGTCGC
AACTATTGAGAAAGACAAGGGCTTAAAATTGCATGTTTGGAAGAAATTGCATGGCGTAA
AGGCTTTATCTCAACACAACAAGTTCTAGCTCAAGCTGAAAAACTTTCTAAGACAGAGTA
TGGTCAGTATCTGAAGAATTTAATTAAGGATGGTTTATAAATTAATCCGTCATACCCATG
AAGGTGGGTATCTCATAAAAGTTGGATATGTTTTGGAGATTCCAATCTGCGCAGTAATGA
CAGGTTTGGTAATATATAGCGATGTTTTACAATGACTAAAAATGGTTTTATGTATATTCT
TACAAATAAGGATAATACTGTTCTGTACATAGTTGTAACATCTAATTTGATAAAAAGAAT
GTATGAGCATAAACATAGCCTTGCAGATGGTTTTACTAAAAATATAATGTTAATAAGTTA
GTTTATTTTGAAATTTATGAAGATATAAAAGCAGCAATTCTGTGAGAAAAGCAGTTGAAA
AAATGAAACAGATCTTGGAAAGAACGAATTATTAATGAGATGAATCCGAATTGGAATGAT
TTATATGAATTAATATGTGAGTAAAACTTTTGTCTTACTGGTGCAGATAGGTATCTCTAA
ATATCAGATGTGATTGGGAGATTACCGCCTACGCGGTAATGACAAGTTTATGCGGTAATG
```

Figure 16F: SEQ ID NO: 7 (Continued)

```
ATAGTTTAGTGAGAGAATGACTAGTCACTATAGGAATGATGATGTAATGAGGAATGAAAA
AATGAACTACAAACCAAAAAATATCCTAGTAACAGGTGCGGCGGGATTTATTGGTAGTAA
CTATGTGCGTATGATGTTATCACGCTATAGTGATATCAAAATAATCTCGTATGATAAGCT
TACTTATGCGGGTAGTTTAGATAATCTAAAAGACTTGAATAATGAACATAACCATACTTT
TATAAAAGGTGATATTTGTGATGAAGTTTTAGTATATCAAACACTGAAAGAATATAAAAT
TGATACGATAGTACATTTTGCTGCAGAATCGCATGTTGATAATTCAATTGCTAATCCAAA
GGTATTTTAGAAACGAATGTGATAGGTACATTTACACTTTTAGATTGTGCTAAAAGGTA
TTGGTTAGATGAGCTAGGTTTAGAAGAAACTAGTTGTAGGTTTCATCATGTATCTACTGA
TGAGGTATATGGTACCTTGGCAAAAGATGAACCAGCCTTTACTGAGATTAAGGCTTATGA
GCCAAATTCACCGTATTCGGCATCTAAGGCGGGATCTGATCATATTTCTAGAGCATATCA
TCATACCTATAAACTTCCGGTAACAATTTCAAATTGTTCAAACAACTATGGACCATACCA
ACATCGAGAGAAATTAATCCCTGTAGTGATAAATAGTTGTATAAACTACAAGCCTATTCC
TGTTTACGGAGATGGTTCGAATATTCGAGATTGGCTATATGTAGAAGATCACTGCGATGC
TATCCAGACAATTGTTGAGAAAGGAGTGGTTGGAGAGGTTTATAATATTGGTGGTATTAA
TGAAGTTGATAATCTAACCTTGGTAAAAACTATCTGTAAACTAATGGATGAATATAAACC
AGAAAATGCTCCACATTCTAACTTAATCACATTTGTGGAAGATAGAAAAGGACATGATTG
GCGTTATGCTATTGATAACAGCAAGATTCAGAATGAGTTAGGATGGAAGCCATCACAAGA
TTTTGATAAGATGTTTAGACAAACTATTGAGTTTTATCTATAGCTTAAATATTTATCTTA
TGAGTATCTCTAAAAAATCAATTTAATTTATTTTTGTGTTAAAAAGTAGTGTTCGCAAGA
ATATAGTTAATCCGAAAGATATTTGTAGAAAAGATATTTGTAGAAATGTTATAATGTCT
AATAAAAATGCCATCATATAGCCAAGATTTTAGAGACATCGTAATTAATAAACATGAAGA
AGGTATGACGGAGTTCGAGCTGAGTAAGTTTTTAACATAGATAAGCGTACAGTTGTTTC
ATGGATAGAGTTTTATAAAAGAACCGGAGATTATAGTTCAAAGCAAGGAGTTGGTTGTGG
CAGAGTCGCTAGCTTTACCGATAAAACATTGATTGAACAGTATTTGATAGATCATCCAGA
TGCAAGTGCATTAGATATAAAAGAAGCATTAGCCCCTGATATTCCAAGAAGTACATTTTA
TGATTGTCTTAATAGACTTGGTTTTAGTTTTAAAAAAAGACTCCAAAATATAAGCAAAGA
AAAGAACATGAAAGGTTGGAGTATATAGAAAAACTAAAAGAAATAGCCAATAAATTTGAT
GTACAAATATTATATCTACCTCCGTACTCTCCAGATTTAAATCCTATTGAAAAGGTTTGG
GCTAACTATTAA
```

Figure 17: SEQ ID NO: 8 PglB nucleotide sequence

```
ATGTTGAAAAAAGAGTATTTAAAAAACCCTTATTTAGTTTTGTTTGCGATGATTATATTA
GCTTATGTTTTTAGTGTATTTTGCAGGTTTTATTGGGTTTGGTGGGCAAGTGAGTTTAAT
GAGTATTTTTTCAATAATCAGTTAATGATCATTTCAAATGATGGCTATGCTTTTGCTGAG
GGCGCAAGAGATATGATAGCAGGTTTTCATCAGCCTAATGATTTGAGTTATTATGGATCT
TCTTTATCCGCGCTTACTTATTGGCTTTATAAAATCACACCTTTTTCTTTTGAAAGTATC
ATTTTATATATGAGTACTTTTTTATCTTCTTGGTGGTGATTCCTACTATTTTGCTAGCT
AACGAATACAAACGTCCTTTAATGGGCTTTGTAGCTGCTCTTTTAGCAAGTATAGCAAAC
AGTTATTATAATCGCACTATGAGTGGGTATTATGATACGGATATGCTGGTAATTGTTTTG
CCTATGTTTATTTTATTTTTATGGTAAGAATGATTTTAAAAAAAGACTTTTTTTCATTG
ATTGCCTTGCCGTTATTTATAGGAATTTATCTTTGGTGGTATCCTTCAAGTTATACTTTA
AATGTAGCTTTAATTGGACTTTTTTTAATTTATACACTTATTTTTCATAGAAAAGAAAAG
ATTTTTTATATAGCTGTGATTTTGTCTTCTCTTACTCTTTCAAATATAGCATGGTTTTAT
CAAAGTGCCATTATAGTAATACTTTTTGCTTTATTCGCCTTAGAGCAAAAACGCTTAAAT
TTTATGATTATAGGAATTTTAGGTAGTGCAACTTTGATATTTTTGATTTTAAGTGGTGGG
GTTGATCCTATACTTTATCAGCTTAAATTTTATATTTTTAGAAGTGATGAAAGTGCGAAT
TTAACGCAGGGCTTTATGTATTTTAATGTCAATCAAACCATACAAGAAGTTGAAAATGTA
GATCTTAGCGAATTTATGCGAAGAATTAGTGGTAGTGAAATTGTTTTTTTGTTTTCTTTG
TTTGGTTTTGTATGGCTTTTGAGAAAACATAAAAGTATGATTATGGCTTTACCTATATTG
GTGCTTGGGTTTTAGCCTTAAAAGGGGGGCTTAGATTTACCATTTATTCTGTACCTGTA
ATGGCCTTAGGATTTGGTTTTTTATTGAGCGAGTTAAGGCTATAATGGTTAAAAAATAT
AGCCAATTAACTTCAAATGTTTGTATTGTTTTGCAACTATTTTGACTTTAGCTCCAGTA
TTTATCCATATTTACAACTATAAAGCGCCAACAGTTTTTTCTCAAAATGAAGCATCATTA
TTAAATCAATTAAAAAATATAGCCAATAGAGAAGATTATGTGGTAACTTGGTGGGATTAT
GGTTATCCTGTGCGTTATTATAGCGATGTGAAAACTTTAGTAGATGGTGGAAAGCATTTA
GGTAAGGATAATTTTTTCCCTTCTTTTGCTTTAAGCAAAGATGAACAAGCTGCAGCTAAT
ATGGCAAGACTTAGTGTAGAATATACAGAAAAAAGCTTTTATGCTCCGCAAAATGATATT
TTAAAAACAGACATTTTGCAAGCCATGATGAAAGATTATAATCAAAGCAATGTGGATTTG
TTTCTAGCTTCATTATCAAAACCTGATTTAAAATCGATACGCCAAAAACTCGTGATATT
TATCTTTATATGCCCGCTAGAATGTCTTTGATTTTTCTACGGTGGCTAGTTTTCTTTT
ATTAATTTAGATACAGGAGTTTTGGATAAACCTTTTACCTTTAGCACAGCTTATCCACTT
GATGTTAAAAATGGAGAAATTTATCTTAGCAACGGAGTGGTTTTAAGCGATGATTTTAGA
AGTTTTAAAATAGGTGATAATGTGGTTTCTGTAAATAGTATCGTAGAGATTAATTCTATT
AAACAAGGTGAATACAAAATCACTCCAATTGATGATAAGGCTCAGTTTTATATTTTTTAT
TTAAAGGATAGTGCTATTCCTTACGCACAATTTATTTTAATGGATAAAACCATGTTTAAT
AGTGCTTATGTGCAAATGTTTTTTTAGGAAATTATGATAAGAATTTATTTGACTTGGTG
ATTAATTCTAGAGATGCTAAGGTTTTTAAACTTAAAATTTAA
```

Figure 18: SEQ ID NO: 9 Pgl B amino acid sequence

```
MLKKEYLKNPYLVLFAMIILAYVFSVFCRFYWVWWASEFNEYFFNNQLMIISNDGYAFAE
GARDMIAGFHQPNDLSYYGSSLSALTYWLYKITPFSFESIILYMSTFLSSLVVIPTILLA
NEYKRPLMGFVAALLASIANSYYNRTMSGYYDTDMLVIVLPMFILFFMVRMILKKDFFSL
IALPLFIGIYLWWYPSSYTLNVALIGLFLIYTLIFHRKEKIFYIAVILSSLTLSNIAWFY
QSAIIVILFALFALEQKRLNFMIIGILGSATLIFLILSGGVDPILYQLKFYIFRSDESAN
LTQGFMYFNVNQTIQEVENVDLSEFMRRISGSEIVFLFSLFGFVWLLRKHKSMIMALPIL
VLGFLALKGGLRFTIYSVPVMALGFGFLLSEFKAIMVKKYSQLTSNVCIVFATILTLAPV
FIHIYNYKAPTVFSQNEASLLNQLKNIANREDYVVTWWDYGYPVRYYSDVKTLVDGGKHL
GKDNFFPSFALSKDEQAAANMARLSVEYTEKSFYAPQNDILKTDILQAMMKDYNQSNVDL
FLASLSKPDFKIDTPKTRDIYLYMPARMSLIFSTVASFSFINLDTGVLDKPFTFSTAYPL
DVKNGEIYLSNGVVLSDDFRSFKIGDNVVSVNSIVEINSIKQGEYKITPIDDKAQFYIFY
LKDSAIPYAQFILMDKTMFNSAYVQMFFLGNYDKNLFDLVINSRDAKVFKLKI
```

Figure 19: SEQ ID NO: 16 Campylobacter sputorum

ATGTCAAATTTTAATTTCGCTAAATTTCTAAATAAATTACCTAGACTTTCTAAACATACTATTTTAATGATTGTT
TTAGCTGTTTGTTTTGGGATATTTTGCAGATTTTACTGGGTAGTTTGGGCTAGTGCTTATCCGCATTTTATATGG
AATGATCAGCTTATGATAAGCACAAATGACGGATATGCATTTGCTGAGGGCACAAGAGATATGATAGCTGGTTTT
CATCAACCAAACGATCTTTCTTACTATGGCTCATCTCTTTCGACGCTTAGCATGTGGTTATATAACATTTTGCCA
TTTTCATTAGAAACTATACTTTTGTATATGAGTACATTTTTATCTCCACTCTTAGCTGTGCCTTTGATACTTATA
GGTAAAGAACTAAACGCTTCAAAAGCGGGTTTTATAGCTGCACTTCTAGCTATTATTGCAAATAGTTATTATAAT
AGAACAATGAGTGGATATTACGATACGGATATGCTAAATATCACTCTTCCTATGATGGTTTTTTGGAGCATAACA
AGACTTGTTCAAAGAAAAGAGAGAGTAAATTTAATATTTATTCCGGTTTTTATGGCGATATATGGATGGTGGTAT
CCATCTTCTTACTCACTATTACTTGCCATGATTGGAATGTTTTTTTTATATACCATTGTTTTTGAAAGATACGAA
AAACTAAACTATGAAGCTATGGTTTTTATGATTTTAGCAATCACAAGCTTTTCTATACAAATTAAATTTATTATA
GTTATTGTTTTGTATGCTTTAATCTATTTTTACCAAAGATTTTTTGATAAAAAAGTAATATTTGCATTAATTATG
GCTTCGTTAATATGCTTTATATGGCTTGGCGGGCTAAACCCTATACTTTTTAACATTAAATTTTATATATTTAGA
GACATTGCAGATAGCGGTGATGCTGTTTTTAAATTTTTCAATGTAAATCAAACAATAAGAGAAAGTTCTGCGATA
GATTTTAACACAGTTGTAACTAGGATTAGCGGGCATTTAATAGTATTTTTGGTATCTATTATAGGATATATTTTA
TTTATAAAAAACAATAAAATTTTACTACTAACTTTACCGATTCTGTTTTTGGGTCTTATGTCATTTAAAAGTGGT
TTAAGATTTACAATATACTCAGTTCCAGTAATGGCTCTTGGTTTTGGCTATTTTGTTATGTATTGTTTTGCAAAA
ATAGATATAAAAGATCGTTTTTTAGGTTATGTGTTTTTATTTGTTGTAACATTTAGTGCATTATATCCATCTTTA
AAACATATTTATGATTATAAAGTATTTCCTGTTTTTACACATAGCGAAGTTGAAAGTTTGGATAATTTAAAAAAT
ATTGCAAAAAGAGAAGATTATGTGCTTTCTTGGTGGGATTATGGTTATCCGATCAGATATTATTCAGATGTAAAA
ACTCTCATAGATGGAGGAAAACATCTTGGAAGTGATAACTTCGCCGTTAGCTTTGCACTTGGAAGCGATCAAAAT
AGCTCTGCAAATATGGCAAGATTAGAAGTTGAATATACAGAAAAAAATTATGAAGAAAAATTTGGATTAAATTTA
AAAAAGATGATGAAAGATTATAATGCTACAAATGTTAATGAGTTTTTATTATCATTAAAAGATGAAAATTTAACT
CTGCCAAAGCAAACAAGAGATATTTATTACTATTTACCAGATAGAATGATATACATATATCCGATAGTGCTAGAT
TTTTCTAGACTTGATTTGACAACAGGGCAAGAATTTGCCCAGCCGTTTTTTATGGTTAGTGAGAGATTTTCAGCT
ACAAATGATAATCAAATAATGTTAAATAACAATGTCATATTAAGTAATGATGGCACTAAATTATCGATAAATGGC
AACTCTTATAGTGTAAATACATATGTTGAAACAAGTTATGATCAAAACGAAAAATTAAATGTAAATTATTTTAAC
ATAGATCCAAATAGCAATTTTTATGTGATTTTTATGAAAGATTATTTGAGAATTTTGGTTTTAGATAAAACTTTG
TATGATAGTGCGTATATTCAACTTTTTGTATTAGAAAATTATGATAAAAATTTATTTGAACCAGTGATTTTAAAC
GGATCAACTAAAATTTATAAACTCAAAAAATGA

Figure 20: SEQ ID NO: 17 Campylobacter sputorum

MSNFNFAKFLNKLPRLSKHTILMIVLAVCFGIFCRFYWVVWASAYPHFIWNDQLMISTNDGYAFAEGTRDMIAGF
HQPNDLSYYGSSLSTLSMWLYNILPFSLETILLYMSTFLSPLLAVPLILIGKELNASKAGFIAALLAIIANSYYN
RTMSGYYDTDMLNITLPMMVFWSITRLVQRKERVNLIFIPVFMAIYGWWYPSSYSLLLAMIGMFFLYTIVFERYE
KLNYEAMVFMILAITSFSIQIKFIIVIVLYALIYFYQRFFDKKVIFALIMASLICFIWLGGLNPILFNIKFYIFR
DIADSGDAVFKFFNVNQTIRESSAIDFNTVVTRISGHLIVFLVSIIGYILFIKNNKILLLTLPILFLGLMSFKSG
LRFTIYSVPVMALGFGYFVMYCFAKIDIKDRFLGYVFLFVVTFSALYPSLKHIYDYKVFPVFTHSEVESLDNLKN
IAKREDYVLSWWDYGYPIRYYSDVKTLIDGGKHLGSDNFAVSFALGSDQNSSANMARLEVEYTEKNYEEKFGLNL
KKMMKDYNATNVNEFLLSLKDENLTLPKQTRDIYYYLPDRMIYIYPIVLDFSRLDLTTGQEFAQPFFMVSERFSA
TNDNQIMLNNNVILSNDGTKLSINGNSYSVNTYVETSYDQNEKLNVNYFNIDPNSNFYVIFMKDYLRILVLDKTL
YDSAYIQLFVLENYDKNLFEPVILNGSTKIYKLKK

Figure 21: Demonstration of DnaK glycosylation in 2 plasmid and 3 plasmid system

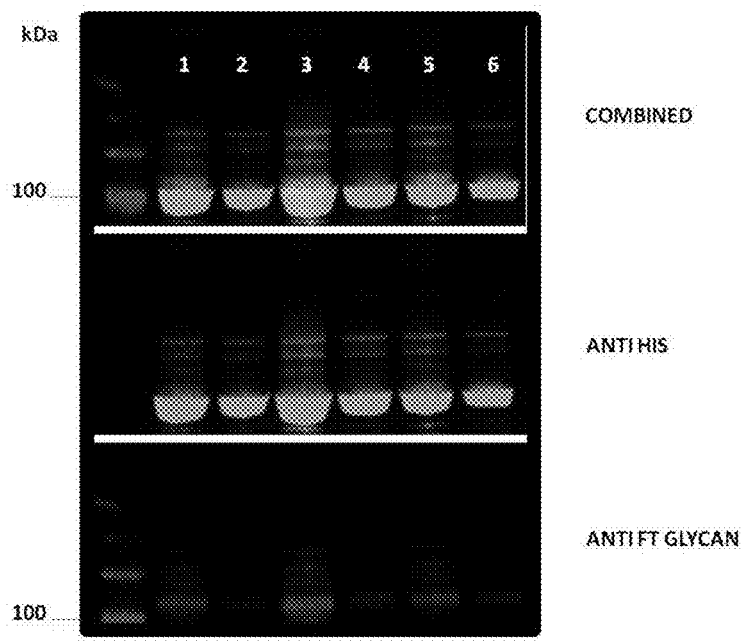

GLYCOCONJUGATE VACCINES

CROSS REFERENCE TO RELATED APPLICATIONS

This is the U.S. National Stage of International Application No. PCT/GB2014/050159, filed Jan. 21, 2014, which was published in English under PCT Article 21(2), which in turn claims the benefit of United Kingdom Application No. 1301085.5, filed Jan. 22, 2013.

FIELD OF THE INVENTION

The disclosure relates to a glycoconjugate vaccine conferring protection against *Francisella tularensis* infections and a method to manufacture a glycoconjugate antigen.

BACKGROUND TO THE INVENTION

Vaccines protect against a wide variety of infectious diseases. Many vaccines are produced by inactivated or attenuated pathogens which are injected into a subject, whereas others, so called 'subunit vaccines', are made from proteins or polysaccharides displayed on the surface of the pathogen. Subunit vaccines are preferred over inactivated or attenuated pathogens as they tend to cause fewer side effects. However, the development and production of a subunit vaccine requires the identification and isolation of protective antigens from the pathogenic organism, and moreover subunit vaccines based on polysaccharide antigens invoke often a T-cell independent immune response which results in low antibody titre, short half-life of the antibodies and low affinity for a specific antigen.

The development of subunit vaccines is an active research area and it has been recognized that the immunogenicity of polysaccharide antigens can be enhanced by conjugation to a protein carrier. Glycoconjugates have the ability to induce both humoral and adaptive immune responses. Currently licensed human glycoconjugate vaccines include those against *Haemophilus influenzae*, *Neisserria meningitidis* and *Streptococcus pneumoniae*, by which bacterial polysaccharides are chemically bound to carrier proteins. The *H. influenzae* type B (Hib) vaccine or Prevnar®, a 13-valent capsule-based glycoconjugate vaccine protective against diseases caused by *S. pneumonia*, employs the carrier protein iCRM197, a non-toxic version of diphtheria toxin isolated from *Corynebacterium diphtheria*.

Although these vaccines are effective, their production requires both the purification of polysaccharide glycan from the native pathogen and the chemical coupling of the sugar to a suitable protein carrier, which can lead to impure products, low yields, variation between batches of conjugates and poses a biohazard as the handling of the pathogenic organism is unavoidable. This process is highly costly, inefficient and time consuming. The use of organic systems represents a more rapid and economical method for the production of glycoconjugates.

So far several pathogenic bacteria have been identified forming glycoproteins and the genes involved identified. The gram negative pathogenic bacterium *Campylobacter jejuni* harbours a gene cluster involved in the synthesis of lipo-oligosaccharides and N-linked glycoproteins.

The protein glycosylation locus, a cluster of 12 genes comprising pglA-pglG, is involved in the glycosylation of over 30 glycoproteins. Part of the gene cluster is PglB, an oligosaccharyltransferase catalysing the transfer of glycans on to a wide range of different non-species related protein acceptors, indicating broad substrate specificity. Moreover PglB when expressed in *E. coli* has been used to produce novel glycoconjugates providing a genetic tool to express heterologous recombinant glycoproteins. Production of glycoconjugate vaccines in a bacterial system are disclosed in patent application WO2009/104074. Glycoconjugates comprising a protein carrier and an antigenic polysaccharide O-antigen form *Shigella*, *E. coli* and *Pseudomonas aeruginosa* using the oligosaccharyltransferase PglB were produced, and bioconjugates against the *Shigella* O1 polysaccharide were shown to elicit an immune response.

Tularemia, also known as lemming or rabbit fever, is common in wild rodents and can be passed on to humans by contact with infected animal tissues, ticks or biting flies, or by inhalation of the infectious organism. Tularemia is found in North America, parts of Europe and Asia and is caused by the gram-negative coccobacillus *Francisella tularensis*. *F. tularensis* is highly infectious, with a mortality rate of up to 30% and based on the above listed characteristics classified as a Class A bioterrorism agent. Tularemia is difficult to diagnose, however, can be treated although with varying success with antibiotics. There are no vaccines available yet.

Recent studies suggest a protective effect using purified lipopolysaccharide (LPS) comprising an O-antigen from *F. tularensis* in a murine infection model; however, the development of glycoprotein vaccines protecting against highly infectious pathogens to high quantities using current methods are associated with high safety concerns.

We disclose a novel bacterial protein glycan coupling technology (PGCT) that allows the production of protective vaccines from the highly virulent wild-type strain of *F. tularensis holarctica*. The recombinant glycoconjugate was easily purified and was capable of providing significant protection against subsequent challenge when compared to LPS based vaccine treatments.

STATEMENT OF INVENTION

According to an aspect of the invention there is provided a vaccine composition comprising: a carrier polypeptide comprising one or more T-cell dependent epitopes and one or more amino acid sequences having the amino acid motif D/E-X-N-X-S/T wherein X is any amino acid except proline and crosslinked to said carrier polypeptide an antigenic polysaccharide wherein the polysaccharide is isolated from *Francisella* and is an O-antigen.

According to an aspect of the invention there is provided an immunogenic composition comprising: a carrier polypeptide comprising one or more T-cell dependent epitopes and one or more amino acid sequences having the amino acid motif D/E-X-N-X-S/T wherein X is any amino acid except proline and crosslinked to said carrier polypeptide is an antigenic polysaccharide wherein the polysaccharide is isolated from *Francisella* and is an O-antigen.

In a preferred embodiment of invention said O-antigen comprises 4)-α-D-GalNAcAN-(1-4)-α-D-GalNAcAN-(1-3)-β-D-QuiNAc-(1-2)-β-D-Qui4NFm-(1-), where GalNAcAN is 2-acetamido-2-deoxy-O-D-galact-uronamide, 4NFm is 4,6-dideoxy-4-formamido-D-glucose and the reducing end group QuiNAc is 2-acetamido-2,6-dideoxy-O-D-glucose.

In a preferred embodiment of the invention said O-antigen is a tetrasaccharide.

In a preferred embodiment of the invention said protein carrier comprises an amino acid sequence as set forth in of SEQ ID NO: 1.

In a preferred embodiment of the invention said protein carrier comprises an amino acid sequence as set forth in of SEQ ID NO: 2.

In a preferred embodiment of the invention said protein carrier comprises an amino acid sequence as set forth in of SEQ ID NO: 3.

In a preferred embodiment of the invention said protein carrier comprises an amino acid sequence as set forth in of SEQ ID NO: 4.

In a preferred embodiment of the invention said protein carrier comprises an amino acid sequence as set forth in of SEQ ID NO: 5.

In a preferred embodiment of the invention said protein carrier comprises an amino acid sequence as set forth in of SEQ ID NO: 6.

In a preferred embodiment of the invention said composition includes an adjuvant.

In a preferred embodiment of the invention said adjuvant is selected from the group consisting of: cytokines selected from the group consisting of e.g. GMCSF, interferon gamma, interferon alpha, interferon beta, interleukin 12, interleukin 23, interleukin 17, interleukin 2, interleukin 1, TGF, TNFα, and TNFβ.

In a further alternative embodiment of the invention said adjuvant is a TLR agonist such as CpG oligonucleotides, flagellin, monophosphoryl lipid A, poly I:C and derivatives thereof.

In a preferred embodiment of the invention said adjuvant is a bacterial cell wall derivative such as muramyl dipeptide (MDP) and/or trehalose dycorynemycolate (TDM).

An adjuvant is a substance or procedure which augments specific immune responses to antigens by modulating the activity of immune cells. Examples of adjuvants include, by example only, agonistic antibodies to co-stimulatory molecules, Freunds adjuvant, muramyl dipeptides, liposomes. An adjuvant is therefore an immunomodulator. A carrier is an immunogenic molecule which, when bound to a second molecule augments immune responses to the latter. The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen. Helper T-cells can also stimulate other immune cells such as cytotoxic T-cells, and a carrier can fulfil an analogous role in generating cell-mediated immunity as well as antibodies.

In a preferred embodiment of the invention said composition includes at least one additional anti-bacterial agent.

In a preferred embodiment of the invention said additional anti-bacterial agent is a different antigenic molecule.

In a preferred embodiment of the invention said composition is a multivalent antigenic composition.

In an alternative preferred embodiment of the invention said additional anti-bacterial agent is an antibiotic.

According to a further aspect of the invention there is provided a vaccine composition according to the invention for use in the prevention or treatment of a *Francisella* infection.

Preferably said infection is caused by *Francisella tularensis*.

According to a further aspect of the invention there is provided a method to treat a *Francisella* infection comprising administering an effective amount of a vaccine or immunogenic composition according to the invention.

Preferably said infection is caused by *Francisella tularensis*.

According to an aspect of the invention there is provided an antigenic polypeptide comprising: a carrier polypeptide comprising one or more T-cell dependent epitopes and one or more amino acid sequences having the amino acid motif D/E-X-N-X-S/T wherein X is any amino acid except proline and crosslinked to said carrier polypeptide is an antigenic polysaccharide wherein the polysaccharide is isolated from *Francisella* and is an O-antigen.

In a preferred embodiment of the invention said O-antigen comprises 4)-α-D-GalNAcAN-(1-4)-α-D-GalNAcAN-(1-3)-β-D-QuiNAc-(1-2)-β-D-Qui4NFm-(1-), where GalNA-cAN is 2-acetamido-2-deoxy-O-D-galact-uronamide, 4NFm is 4,6-dideoxy-4-formamido-D-glucose and the reducing end group QuiNAc is 2-acetamido-2,6-dideoxy-O-D-glucose.

According to a further aspect of the invention there is provided a modified bacterial cell wherein said cell is genetically modified to include:

i) a nucleic acid molecule comprising the nucleotide sequence of the *Francisella* O-antigen biosynthetic polysaccharide locus [SEQ ID NO: 7];

ii) a nucleic acid molecule comprising a nucleotide sequence of an oligosaccharyltransferase [SEQ ID NO: 8] or a functional variant thereof wherein said variant comprises a nucleic acid molecule the complementary strand of which hybridizes under stringent hybridization conditions to the sequence set forth in SEQ ID NO: 8 and wherein said nucleic acid molecule encodes an oligosaccharyltransferase; and/or iii) a nucleic acid molecule comprising a nucleotide sequence of an oligosaccharyltransferase [SEQ ID NO: 16] or a functional variant thereof wherein said variant comprises a nucleic acid molecule the complementary strand of which hybridizes under stringent hybridization conditions to the sequence set forth in SEQ ID NO: 16 and wherein said nucleic acid molecule encodes an oligosaccharyltransferase; and iv) a nucleic acid molecule comprising a nucleotide sequence of carrier polypeptide wherein the a carrier polypeptide comprising one or more T-cell dependent epitopes and one or more amino acid sequences having the amino acid motif D/E-X-N-X-S/T wherein X is any amino acid except proline, wherein said bacterial cell is adapted for expression of each nucleic acid molecule and synthesizes an antigenic polypeptide according to the invention.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand.

The following is an exemplary set of hybridization conditions and is not limiting.

Very High Stringency (Allows Sequences that Share at Least 90% Identity to Hybridize)
  i) Hybridization: 5×SSC at 65° C. for 16 hours
  ii) Wash twice: 2×SSC at room temperature (RT) for 15 minutes each
  iii) Wash twice: 0.5×SSC at 65° C. for 20 minutes each High Stringency (Allows Sequences that Share at Least 80% Identity to Hybridize)
  i) Hybridization: 5×-6×SSC at 65° C.-70° C. for 16-20 hours
  ii) Wash twice: 2×SSC at RT for 5-20 minutes each
  iii) Wash twice: 1×SSC at 55° C.-70° C. for 30 minutes each Low Stringency (Allows Sequences that Share at Least 50% Identity to Hybridize)
  i) Hybridization: 6×SSC at RT to 55° C. for 16-20 hours
  ii) Wash at least twice: 2×-3×SSC at RT to 55° C. for 20-30 minutes each.

A variant oligosaccharyltransferase polypeptide as herein disclosed may differ in amino acid sequence by one or more substitutions, additions, deletions, truncations that may be present in any combination. Among preferred variants are those that vary from a reference polypeptide [SEQ ID NO: 9, SEQ ID NO: 17] by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 40% or 45% identity, more preferably at least 50% identity, still more preferably at least 60%, 65%, 70%, 75%, 80%, 85%, 90%, 95% identity, or at least 99% identity with the full length amino acid sequence illustrated herein.

In a preferred embodiment of the invention at least the oligosaccharyltransferase of ii) or iii) above is integrated into the bacterial genome to provide a stably transfected and expressing oligosaccharyltransferase.

In a further preferred embodiment of the invention one or more nucleic acid molecules encoding carrier polypeptides are also integrated into the bacterial genome.

According to a further aspect of the invention there is provided a bacterial cell culture comprising a genetically modified bacterial cell according to the invention.

According to a further aspect of the invention there is provided a process for the production of one or more glycoconjugates comprising:
  i) providing a bacterial cell culture according to the invention;
  ii) providing cell culture conditions; and
  iii) isolating one or more glycoconjugates from the bacterial cell or cell culture medium.

According to a further aspect of the invention there is provided a cell culture vessel comprising a bacterial cell culture according to the invention.

In a preferred embodiment of the invention said cell culture vessel is a fermentor.

Bacterial cultures used in the process according to the invention are grown or cultured in the manner with which the skilled worker is familiar, depending on the host organism. As a rule, bacteria are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the bacteria as described above by processes known to the skilled worker, for example by extraction, distillation, crystallization, if appropriate precipitation with salt, and/or chromatography. In this process, the pH value is advantageously kept between pH 4 and 12, preferably between pH 6 and 9, especially preferably between pH 7 and 8.

An overview of known cultivation methods can be found in the textbook Bioprocess technology 1. Introduction to Bioprocess technology (Gustav Fischer Verlag, Stuttgart, 1991) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the bacterial strains in question. Descriptions of culture media for various bacteria can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing bacteria usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures.

CFU of *F. tularensis* strain HN63 via the i.p. route. Both LPS, LPS+SAS and test glycoconjugate provided improved protection when compared to the relevant unvaccinated controls (P<0.001) and the SAS alone provided no survival benefit (P>0.05) as analysed by stratified log rank test. The test glycoconjugate provided significantly better protection than the LPS alone or LPS+SAS vaccine (P<0.001 and P=0.025 respectively).

Figure 5:
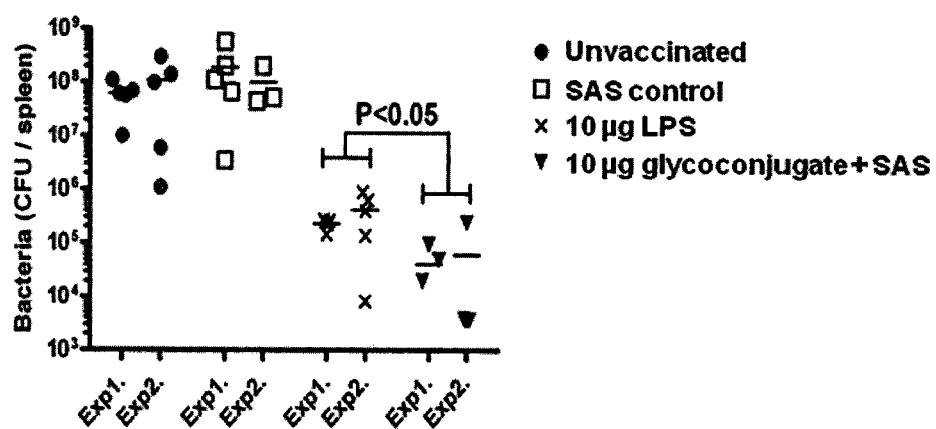

FIG. 5: Mice vaccinated with test glycoconjugate shows a reduced bacterial load in spleens compared to LPS and controls. Unvaccinated, SAS vaccinated, 10 μg LPS, or 10 μg test glycoconjugate+SAS vaccinated mice were challenged with 100 CFU of *F. tularensis* strain HN63 via the i.p. route. Spleens were removed 3 days post infection from each group (n=5) and assessed for bacterial CFUs. Logarithm data were analysed using a general linear model and Bonferroni's post tests. There was no difference in bacterial load between SAS vaccinated and unvaccinated mice (P>0.05) but the 10 μg LPS or 10 μg test glycoconjugate vaccinations had significantly decreased bacterial load when compared to relevant controls (P<0.001). Mice vaccinated with the test glycoconjugate+SAS had significantly reduced bacterial numbers in the spleen compared to LPS (P<0.05).

Figure 6:
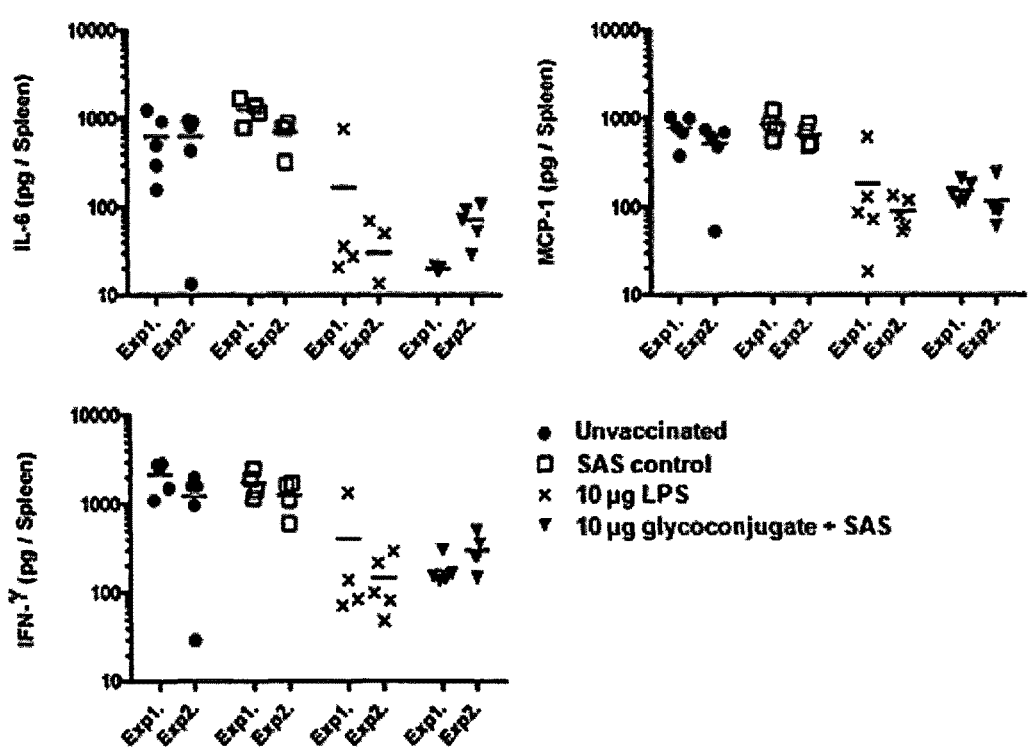
Figure 7:
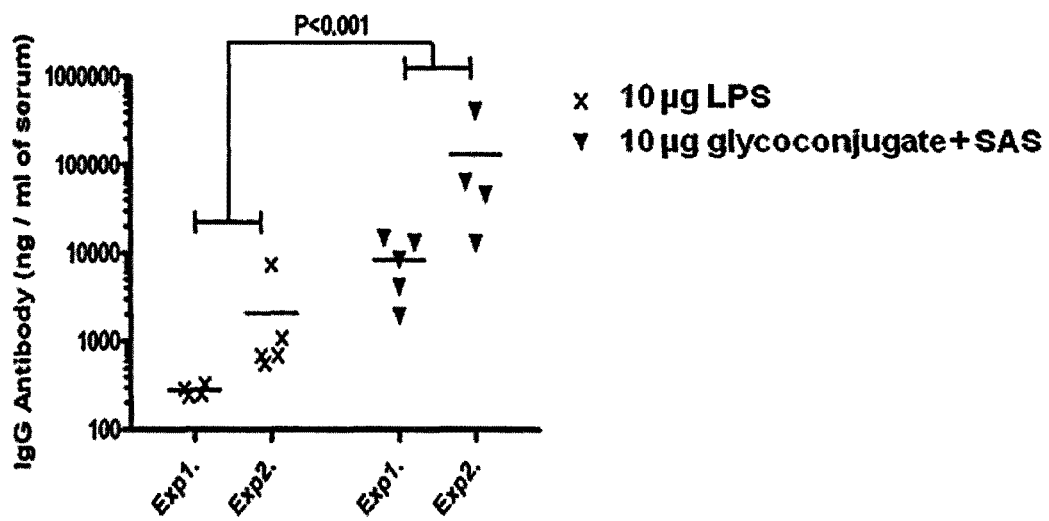
Figure 8:
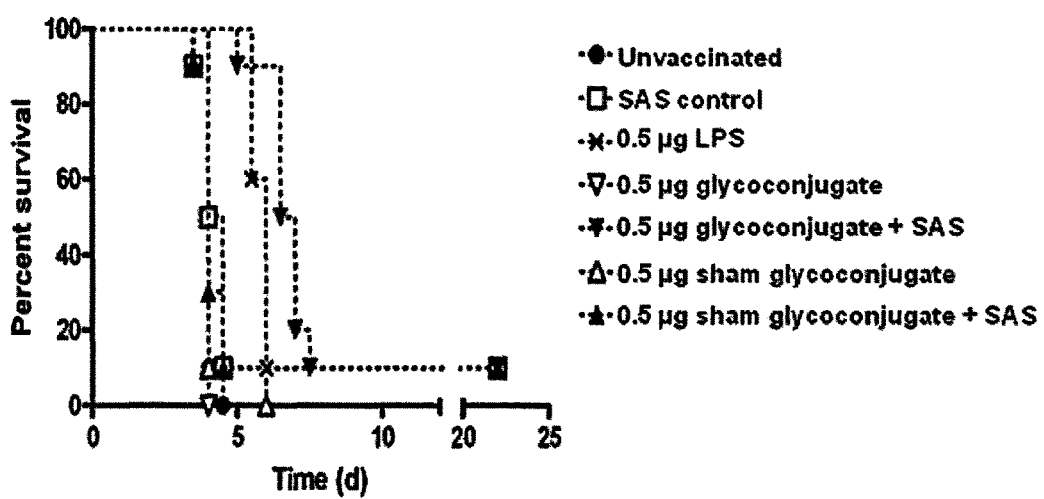
Figure 9:
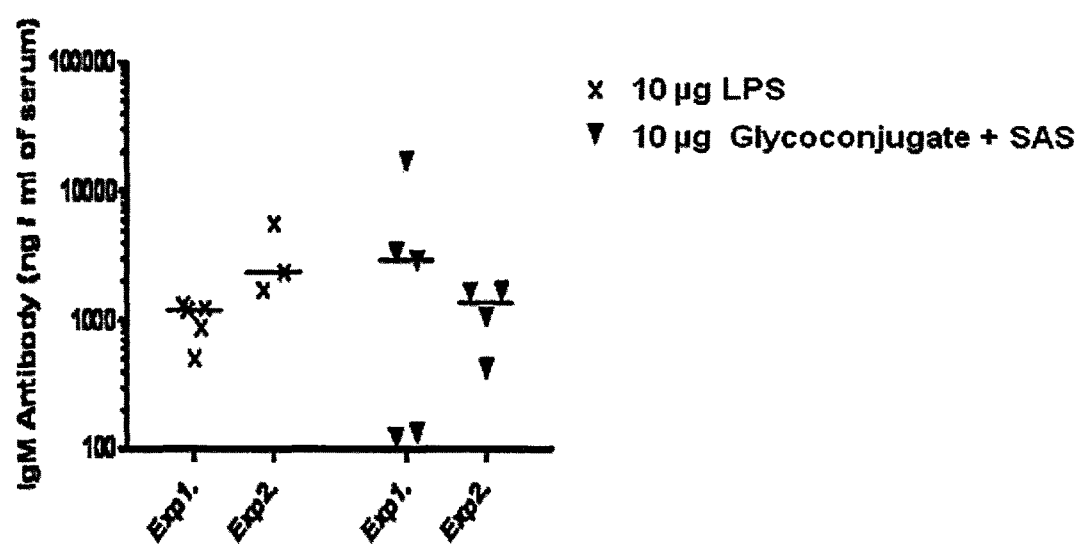

FIG. 6: Reduced inflammatory responses seen in LPS and glycoconjugate vaccinated mice compared to controls. Unvaccinated, SAS vaccinated, 10 μg LPS or 10 μg test glycoconjugate vaccinated mice were challenged with 100 CFU of *F. tularensis* strain HN63 via the i.p. route. Spleens were removed 3 days post infection from each group (n=5) and assessed for cytokine response. Levels of IL-6, MCP-1 and IFN-γ, were measures by CBA; all cytokine data pg/spleen. Individual points represent individual samples with line indicating the mean. Logarithm data was analysed using a general linear model and Bonferroni's post tests. Cytokine production (IL-6, MCP-1 and IFN-γ) was comparable between controls (untreated and SAS) and the two vaccine treated groups (LPS and glycoconjugate). Cytokine concentration was reduced in vaccinated mice compared to relevant controls (P<0.05) and the experiments 1 and 2 did not differ from each other (P>0.05);

FIG. 7: Increased IgG response in glycoconjugate vaccinated mice animals 7 days prior to challenge. Increased LPS specific IgG was observed in the glycoconjugate+SAS vaccinated group when compared to animals vaccinated with LPS only (P<0.001);

FIG. 8: Pilot study of vaccine candidates and relevant controls. Balb/C mice were vaccinated with three doses, 2 weeks apart with candidate vaccine or relevant controls (n=10 per group). Mice were challenged 5 weeks following final vaccination with 100 CFU of *F. tularensis* strain HN63 via the i.p. route. 0.5 μg of product per time point were assessed. Mice vaccinated with 0.5 μg test glycoconjugate with SAS (P<0.05) and the 0.5 μg LPS vaccines (P<0.001) survived longer than controls as determined by log rank test. Glycoconjugate, *F. tularensis* O-antigen ExoA glycoconjugate; sham glycoconjugate, *C. jejuni* 81116 heptasaccharide ExoA glycoconjugate;

FIG. 9: *F. tularensis* LPS specific IgM levels observed in vaccinated mice 1 day prior to challenge. There were no differences between LPS specific IgM levels in the glycoconjugate and SAS vaccinated group when compared to animals vaccinated with LPS only group (P>0.05). We observed no evidence of the LPS-specific IgM titres differing between experiments (P>0.05).

FIG. 10 (SEQ ID 1) Amino acid sequence of of carrier protein ExoA (*Pseudomonas aeruginosa*)

FIG. 11 (SEQ ID NO: 2) Amino acid sequence of carrier protein TUL4 (*Francisella tularensis*)

FIG. 12 (SEQ ID NO: 3) Amino acid sequence of carrier protein FTT1713c (*Francisella tularensis*)

FIG. 13 (SEQ ID NO: 4) Amino acid sequence of carrier protein FTT1695 (*Francisella tularensis*)

FIG. 14 (SEQ ID NO: 5) Amino acid sequence of carrier protein FTT1269c (*Francisella tularensis*)

FIG. 15 (SEQ ID NO: 6) Amino acid sequence of carrier protein FTT1696 (*Francisella tularensis*)

FIGS. 16A-16F (SEQ ID NO: 7) Nucleotide sequence encoding the *Francisella* O-antigen biosynthetic polysaccharide FIG. 17: (SEQ ID NO: 8) nucleotide sequence encoding the oligosaccharyltransferase PglB (*C. jejuni*)

FIG. 18: (SEQ ID NO: 9) Pgl B amino acid sequence (*C. jejuni*)

FIG. 19: (SEQ ID NO: 16) nucleotide sequence encoding the oligosaccharyltransferase PglB (*Campylobacter sputorum*)

FIG. 20 (SEQ ID NO: 17) Amino acid sequence (full length) of PglB (*Campylobacter sputorum*)

FIG. 21 HIS tag purified DNAK protein from cultures of *Escherichia coli* CLM24. Comparison of 2 plasmid system (chromosomally encoded PglB) and standard 3 plasmid system. Lanes 1/3/5, three biological replicates of DNAK purified from the two plasmid system; Lanes 2/4/6, three biological replicates of DNAK purified from the 3 plasmid system. Three plasmid system consists of pGAB2 coding for *Francisella tularensis* O antigen, pEC415DNAK coding for *F. tularensis* DNAK and pGVXN114 coding for PglB.

Figure 22:
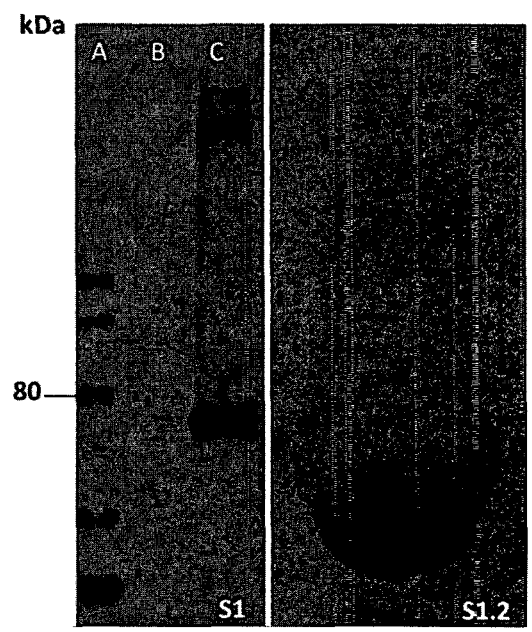

FIG. 22: The *F. tularensis* O-antigen is conjugated to ExoA. Treatment of the glycoconjugate with proteinase K to degrade ExoA results in loss of the O-antigen ladder at the corresponding size. Western blot was performed with monoclonal antibody FB11. A, Markers; B, proteinase K digested ExoA *F. tularensis* O-antigen glycoconjugate; C, glycoconjugate heated to 50° C. o/n without proteinase K. S1.2; Silver stained ExoA *F. tularensis* O-antigen glycoconjugate.

Figure 23:
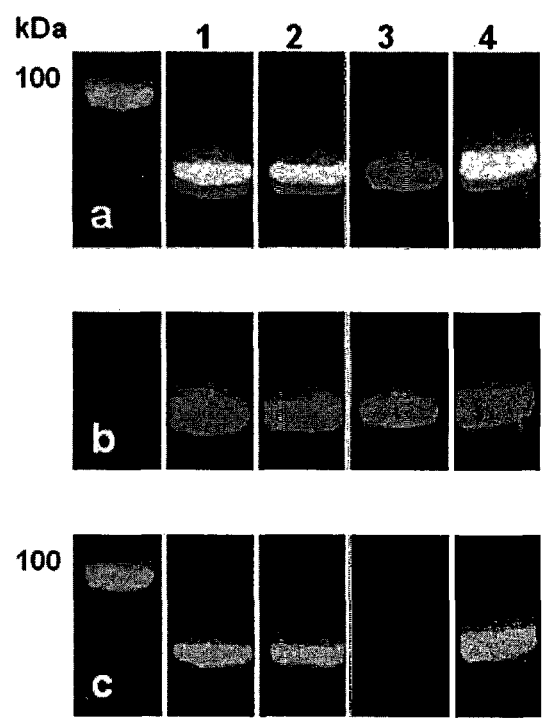

FIG. 23: Comparison of LPS-specific IgM levels from the glycoconjugate and LPS vaccine groups. Panel a, combined anti glycan and anti HIS signal; panel b, anti HIS signal only; panel c, anti-glycan signal only. Lane 1, $_{260}$DNNNS$_{264}$ altered to $_{260}$DNQNS$_{264}$; Lane 2, $_{402}$DQNRT$_{406}$ altered to $_{402}$DQQRT$_{406}$; Lane 3, $_{260}$DNNNS$_{264}$ altered to $_{260}$DNQNS$_{264}$ and $_{402}$DQNRT$_{406}$ altered to $_{402}$DQQRT$_{406}$; Lane 4, exotoxin A encoded from pGVXN150.

TABLE 1

Strains and plasmids used

| Strain/plasmid | Description | Source |
| --- | --- | --- |
| *E. coli* DH5α | F-φ80lacZΔM15 Δ(lacZYA-argF) U169 deoRrecA1 endA1 hsdR17 (rk−, mk+), gal- phoAsupE44λ - thi-1 gyrA96 relA1 | Invitrogen |

TABLE 1-continued

Strains and plasmids used

| Strain/plasmid | Description | Source |
| --- | --- | --- |
| *E. coli* XL-1 | endA1 gyrA96(nalr)thi-1 relA1 lac gln V44 F'[::Tn10 proAB+ laclq Δ (lacZ)M15] hsdR17($r_k^- m_k^+$) | Stratagene |
| *E. coli* CLM24 | rph-l IN(rrnD-rrnE) 1, ΔwaaL | 5 |
| *F. tularensis* subs, *tularensis* strain SchuS4 | Type A strain | DSTL, Porton Down laboratories |
| *F. tularensis* subs, *holarctica* strain HN63 | Type B strain, isolated in Norway from an infected Hare | Green, M., et al., Efficacy of the live attenuated *Francisella tularensis* vaccine (LVS) in a murine model of disease. Vaccine, 2005. 23(20): p. 2680-6 |
| pGEM-T Easy | TA cloning vector, amp$^r$ | Promega |
| pLAFR1 | Low copy expression vector, tet$^r$ | Vanbleu E, Marchal K, Vanderleyden J. Genetic and physical map of the pLAFR1 vector. DNA Seq. 2004 June; 15(3): 225-7. |
| pGAB1 | *F. tularensis* O antigen coding region inserted into MCS of pGEM-T easy | This study |
| pGAB2 | *F. tularensis* subs. *tularensis* strain SchuS4 O antigen coding region inserted into Ecorl site of pLAFR. | This study |
| pGVXN114 | Expression plasmid for CjPglB regulated from the Lac promoter in pEXT21. IPTG inducible, HA tag, Spec$^r$. | GlycoVaxyn |
| pGVXN115 | Expression plasmid for *C. jejuni* non functional PglB due to a mutation at $_{457}$WWDYGY$_{462}$ to $_{457}$WAAYGY$_{462}$, regulated from the Lac promoter in pEXT21. IPTG inducible, HA tag, Spec$^r$. | GlycoVaxyn |
| pGVXN150$_{260}$DNQNS$_{264}$ | Expression plasmid for *Pseudomonas aeruginosa* PA103(DSM111/) Exotoxin A with the signal peptide of the *E.coli* DsbA protein, two inserted bacterial N-glycosylation sites, AA at position 262 altered from N to Q and a hexahis tag at the C-terminus. Induction under control of an arabinose inducible promoter, Amp$^r$ | This study |
| pGVXN150$_{402}$DQQRT$_{406}$ | Expression plasmid for *Pseudomonas aeruginosa* PA103(DSM111/) Exotoxin A with the signal peptide of the *E. coli* DsbA protein, two inserted bacterial N-glycosylation sites, AA at position 404 altered from N to Q and a hexahis tag at the C-terminus. Induction under control of an arabinose inducible promoter, Amp$^r$ | This study |

TABLE 1-continued

Strains and plasmids used

| Strain/plasmid | Description | Source |
|---|---|---|
| pGVXN150$_{260}$DNQNS$_{264}$/$_{402}$DQQRT$_{406}$ | Expression plasmid for *Pseudomonas aeruginosa* PA103(DSM111/) Exotoxin A with the signal peptide of the *E. coli*DsbA protein, two inserted bacterial N-glycosylation sites, AA at position 262 and 404 altered from N to Q and a hexahis tag at the C-terminus. Induction under control of an arabinose inducible promoter, Amp$^r$ | This study |
| pACYCpgl | pACYC184 carrying the CjPglB locus, Cm$^r$ | 5 |
| *E. coli* CedAPglB | *E. coli* strain CLM24 with a chromosomally inserted IPTG inducible copy of PglB | This study |

Materials and Methods
Bacterial Strains and Plasmids

*Escherichia coli* strains were grown in LB at 37° C., 180 r.p.m. Antibiotics were used at the following concentrations; tetracycline 20 µg/ml, ampicillin 100 µg/ml, spectinomycin 80 µg/ml, chloramphenicol 30 µg/ml. The host strain for initial cloning experiments was *E. coli* XL-1, subsequent strains used for glycoconjugate production were *E. coli* DH5α and CLM24 (Table 1). For efficacy studies, mice were challenged with *F. tularensis* subsp. *holarctica* strain HN63. The bacterium was cultured on blood cysteine glucose agar plates (supplemented with 10 ml of 10% (wt/vol) histidine per liter) at 37° C. for 18 hours.

Cloning, Sequencing and Expression of the *F. Tularensis* O Antigen Coding Region DNA was prepared from the *F. tularensis* subsp. *tularensis* strain SchuS4 by phenol extraction as described by Karlsson et al. (2000). The O-antigen coding region was amplified using the primers FTfragment2rev (5'-GGATCAT-TAATAGCTAAATGTAGTGCTG-3'; SEQ ID 10) and Oant1ftfwd (5'-TTTTGAATTCTACAGGCTGTCAATG-GAGAATG-3'; SEQ ID 11) using the following cycling conditions: 94° C., 15 sec, 55° C., 15 sec, 68° C., 20 min; 35 cycles using Accuprime TaqHifi (Invitrogen U.K.). This was cloned into the TA cloning vector pGEM-T Easy to generate the vector pGAB1. The plasmid pGAB1 was digested with EcoRI and the insert was subcloned into the vector pLAFR to generate the construct pGAB2.

Immunofluorescence Imaging of *E. coli* Cells Carrying *F. Tularensis* O Antigen Coding Region Immunofluorescence was carried out as previously described [17] with the modification that the IgG2a mouse monoclonal antibody FB11 was used to detect *F. tularensis* O antigen (1 µl/ml in 5% (v/v) FCS/PBS).

Production and Purification of Glycoconjugate Vaccine

*E. coli* CLM24 carrying the vectors pGAB2, pGVXN114 and pGVXN150 was grown for 16 h in 200 mL LB broth at 37° C., 180 r.p.m. This was used to inoculate 1.8 L of LB broth and further incubated at 110 r.p.m. 37° C. to an OD.600 nm reading of 0.4 to 0.6. L-arabinose was then added to a final concentration of 0.2% and IPTG to a final concentration of 1 mM to induce expression of exoA and CjpglB respectively; following 5 hours of incubation, 0.2% L-arabinose was added again and the culture left to incubate o/n.

Cells were harvested by centrifugation at 6,000 r.p.m. for 30 m, and pelleted cells were incubated at room temperature for 30 m in a lysis solution composed of 10× BugBuster protein extraction reagent (Novagen) diluted to 1× in 50 mM NaH$_2$PO$_4$, 300 mM NaCl, 10 mM imidazole, pH 8.0 supplemented with 0.1% Tween, 1 mg/ml lysozyme and 1 µl/ml Benzonase nuclease (Novagen). Cell debris was removed by centrifugation at 10,000 r.p.m. for 30 m, the supernatant was collected and 1 ml Ni-NTA agarose (QIAgen) was added to the supernatant. The slurry-lysate was incubated for 1 h at 4° C. with shaking then loaded into 10 ml polypropylene columns (Thermo scientific). His tagged ExoA was purified according to manufacturer's instructions (QIA expressionist, QIAGEN) with the addition of 20% glycerol and 5% glucose to the elution buffer. Protein yields were estimated using a bicinchonic acid assay kit according to manufacturer's instructions (Pierce® Biotechnology BCA protein Assay Kit, U.S.A.).

For large-scale protein purification, material was isolated using GE Healthcare His Trap columns and an AKTA purifier with an imidazole gradient of 30-500 mM. The collected fraction containing ExoA glycosylated with *F. tularensis* O-antigen was further purified using a resource Q anionic exchange column (GE Healthcare) with a NaCl gradient from 0 to 500 mM in 20 mM TrisHCl pH 8.0. This generated a typical yield of 2-3 mg/ml of glycoconjugate per 2 L of *E. coli* culture.

The same techniques were used for the generation of the 'sham' *C. jejuni* heptasaccharide ExoA glycoconjugate encoded by pACYCpgl [18].

Using the *E. coli* chromosomally inserted strain CLM 24 CedAPglB:

*Escherichia coli* strain CLM24 with a chromosomally inserted copy of pglB were grown in Luria-Bertani (LB) broth at 37° C., with shaking. Antibiotics were used at the following concentrations: tetracycline 20 µg ml$^{-1}$ and ampicillin 100 µg ml$^{-1}$. Tetracycline was used to maintain the plasmid pGAB2 coding for *Francisella tularensis* O antigen and ampicillin was used to maintain the plasmid coding for the acceptor carrier protein.

*Escherichia coli* cells were grown for 16 h in 200 ml LB broth at 37° C., with shaking. This was used to inoculate 1.8 l of LB broth and further incubated with shaking at 37° C. until an OD$_{600}$ reading of 0.4-0.6 was reached. At this point L-arabinose was added to a final concentration of 0.2 percent and IPTG to a final concentration of 1 mM to induce expression of the acceptor protein and pglB, respectively; after another 5 h of incubation, 0.2% L-arabinose was added again and the culture left to incubate overnight.

Cells were harvested by centrifugation at 5300 g for 30 min, and pelleted cells were incubated at room temperature for 30 min in a lysis solution composed of 10× BugBuster protein extraction reagent (Novagen) diluted to 1× in 50 mM $NaH_2PO_4$, 300 mM NaCl, 10 mM imidazole, pH 8.0 supplemented with 0.1 percent Tween, 1 mg ml$^{-1}$ lysozyme and 1 μl ml$^{-1}$ Benzonase nuclease (Novagen). Cell debris was removed by centrifugation at 7840 g for 30 min, the supernatant was collected and 1 ml Ni-NTA agarose (QIAGEN) was added to the supernatant. The slurry-lysate was incubated for 1 h at 4° C. with shaking then loaded into 10 ml polypropylene columns (Thermo Scientific). His-tagged ExoA was purified by the addition of an elution buffer according to manufacturer's instructions (QIA expressionist, QIAGEN) containing 250 mM imidazole with the addition of 20 percent glycerol and 5 percent glucose.

Alternatively cells were grown in LB agar plates containing tetracycline, ampicillin, IPTG to a final concentration of 50 μM and L-arabinose to a final concentration of 0.2% for 16 h at 37° C. Cells were subsequently harvested by scraping and protein purified as indicated above.

Immunoblot Analysis

To verify transfer and presence of the *F. tularensis* O antigen, samples were analysed by western blotting. *E. coli* cells were grown o/n in 10 ml LB broth and diluted to an O.D.600 nm of 1.0. Cells were centrifuged at 13,000 r.p.m. for 10 min, supernatant was removed and cells were resuspended in 100 μl Laemmli buffer and lysed by boiling for 10 min before analysis by western blotting or silver staining. Mouse anti *F. tularensis* O-antigen monoclonal antibody FB011 (AbCam U.K.) was used at a dilution of 1:1,000, rabbit anti HIS monoclonal antibody was used to detect ExoA at a dilution of 1:10,000 (AbCam U.K.). Secondary antibodies used were goat anti mouse IRDye680 and IRDye800 conjugates used at 1:5000 dilutions. Signal detection was undertaken using the Odyssey® LI-COR detection system (LI_COR Biosciences GmbH).

Cytokine Response Analysis

Spleen supernatants were assessed using mouse inflammatory cytometric bead array kit (CBA—BD biosciences) for IL-10, IL-12p70, IFN-γ, IL-6, TNF-α, and MCP-1. Samples were incubated with the combined capture bead cocktail, and incubated for 1 h at room temperature. Following incubation, PE detection antibodies were added and incubated for a further 1 h. Samples were then washed and resuspended in FACS buffer. Cytokine concentrations were measured via quantification of PE fluorescence of samples in reference to a standard curve.

BALB/c Mouse Challenge Studies

Female Balb/C mice were obtained from Charles River Laboratories (Kent, U.K.) at 6-8 weeks of age. The pilot study was done in groups of 10 mice immunised with either 0.5 μg *F. tularensis* LPS, 0.5 μg *F. tularensis* glycoconjugate, 0.5 μg *F. tularensis* glycoconjugate+SAS, 0.5 μg 'sham' glycoconjugate+SAS, 0.5 μg 'sham' glycoconjugate or SAS only. One group of mice were left untreated as challenge efficacy controls. Immunisations occurred on days 0, 14 and 28 via intra-peritoneal (IP) route. Mice were challenged 35 days post-immunisation with 100 CFU of *F. tularensis* strain HN63 by the IP route, delivered in 0.1 ml.

Subsequent experiments used the same schedule with 15 mice per group and doses of 10 μg of material per immunisation. Four weeks following final vaccination 5 mice from each group were tail bled to obtain sera for antibody analysis and culled at day 3 post-infection with spleens harvested to analyse bacterial load and cytokine response. For the enumeration of bacteria, spleen samples were homogenized in 2 ml of PBS through 40 μm cell sieves (BD Biosciences) and 100 μl aliquots were plated onto BCGA plates. *F. tularensis* LPS-specific IgM and total IgG levels were determined by ELISA as previously described [19]. All work was performed under the regulations of the Home Office Scientific Procedures Act (1986).

Statistical Analysis

Statistical analyses were performed using the program PASW (SPSS release 18.0). Survival data was analysed by pair-wise Log Rank test stratified by experiment. Cytokine and bacterial load data were analysed using univariate general linear models, using Bonferroni's post tests to further clarify significant differences.

Production and Purification of Glycoconjugate Vaccine

*E. coli* CLM24 carrying the vectors pGAB2, pGVXN114 and pGVXN150 was grown for 16 h in 200 mL LB broth at 37° C., 180 r.p.m. This was used to inoculate 1.8 L of LB broth and further incubated at 110 r.p.m. 37° C. until an O.D600 reading of 0.4 to 0.6 was reached. At this point L-arabinose was added to a final concentration of 0.2% and IPTG to a final concentration of 1 mM to induce expression of exoA and CjpglB respectively; after another 5 hours of incubation, 0.2% L-arabinose was added again and the culture left to incubate o/n.

Cells were harvested by centrifugation at 6,000 r.p.m. for 30 m, and pelleted cells were incubated at room temperature for 30 m in a lysis solution composed of 10× BugBuster protein extraction reagent (Novagen) diluted to 1× in 50 mM NaH2PO4, 300 mM NaCl, 10 mM imidazole, pH 8.0 supplemented with 0.1% Tween, 1 mg/ml lysozyme and 1 μl/ml Benzonase nuclease (Novagen). Cell debris was removed by centrifugation at 10,000 r.p.m. for 30 m, the supernatant was collected and 1 ml Ni-NTA agarose (QIAgen) was added to the supernatant. The slurry-lysate was incubated for 1 h at 4° C. with shaking then loaded into 10 ml polypropylene columns (Thermo scientific). His tagged ExoA was purified by the addition of an elution buffer according to manufacturer's instructions (QIA expressionist, QIAGEN) containing 250 mM imidazole with the addition of 20% glycerol and 5% glucose. Protein yields were estimated using a bicinchonic acid assay kit according to manufacturer's instructions (Pierce® Biotechnology BCA protein Assay Kit, U.S.A.).

For large-scale protein purification, material was isolated using GE Healthcare HIS trap columns and an AKTA purifier with an imidazole gradient of 30 mM to 500 mM. The collected fraction containing ExoA glycosylated with *F. tularensis* O-antigen was further purified using a resource Q anionic exchange column (GE Healthcare) with a NaCl gradient from 0 to 500 mM in 20 mM TrisHCl pH 8.0. This generated a typical yield of 2-3 mg/ml of glycoconjugate per 2 L of *E. coli* culture.

The same techniques were used for the generation of the 'sham' *C. jejuni* heptasaccharide ExoA glycoconjugate. The plasmid coding for this heptasaccharide was pACYCpgl carrying the entire Cjpgl cluster from *C. jejuni* 81116 [1].

Protein Expression

*Escherichia coli* strain CLM24 with a chromosomally inserted copy of pglB were grown in Luria-Bertani (LB) broth at 37° C., with shaking. Antibiotics were used at the following concentrations: tetracycline 20 μg ml-1 and ampicillin 100 μg ml-1. Tetracycline was used to maintain the plasmid pGAB2 coding for *Francisella tularensis* O antigen and ampicillin was used to maintain the plasmid coding for the acceptor carrier protein.

*Escherichia coli* cells were grown for 16 h in 200 ml LB broth at 37° C., with shaking. This was used to inoculate 1.8 l of LB broth and further incubated with shaking at 37° C. until an OD600 reading of 0.4-0.6 was reached. At this point L-arabinose was added to a final concentration of 0.2 percent and IPTG to a final concentration of 1 mM to induce expression of the acceptor protein and pglB, respectively; after another 5 h of incubation, 0.2 percent L-arabinose was added again and the culture left to incubate overnight.

Cells were harvested by centrifugation at 5300 g for 30 min, and pelleted cells were incubated at room temperature for 30 min in a lysis solution composed of 10× BugBuster protein extraction reagent (Novagen) diluted to 1× in 50 mM NaH2PO4, 300 mM NaCl, 10 mM imidazole, pH 8.0 supplemented with 0.1 percent Tween, 1 mg ml-1 lysozyme and 1 μl ml-1 Benzonase nuclease (Novagen). Cell debris was removed by centrifugation at 7840 g for 30 min, the supernatant was collected and 1 ml Ni-NTA agarose (QIAGEN) was added to the supernatant. The slurry-lysate was incubated for 1 h at 4° C. with shaking then loaded into 10 ml polypropylene columns (Thermo Scientific). His-tagged ExoA was purified by the addition of an elution buffer according to manufacturer's instructions (QIA expressionist, QIAGEN) containing 250 mM imidazole with the addition of 20 percent glycerol and 5 percent glucose.

Figure 1:
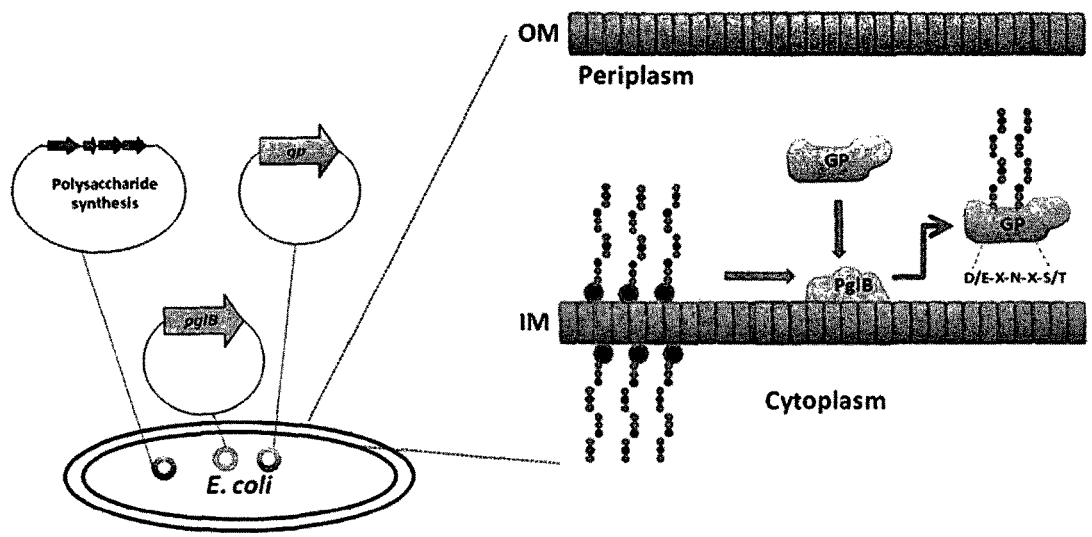
FIG. 1: Principles of Protein Glycan Coupling Technology in *E. coli*. An *E. coli* cell is transformed with three plasmids to generate the cloned glycoconjugate protein (GP). The plasmids encode the oligosaccharyltransferase PglB, the biosynthetic polysaccharide locus and the carrier protein. The polysaccharide is synthesised on an undecaprenol pyrophosphate lipid anchor (●) within the cytoplasm, this is transferred to the periplasmic compartment where PglB recognises the lipid link reducing end sugar and transfers the polysaccharide en bloc onto an acceptor sequon (D/E-X-N-X-S/T) on the carrier protein to produce the glycoconjugate protein (GP). IM, inner membrane; OM, outer membrane.
Figure 2:
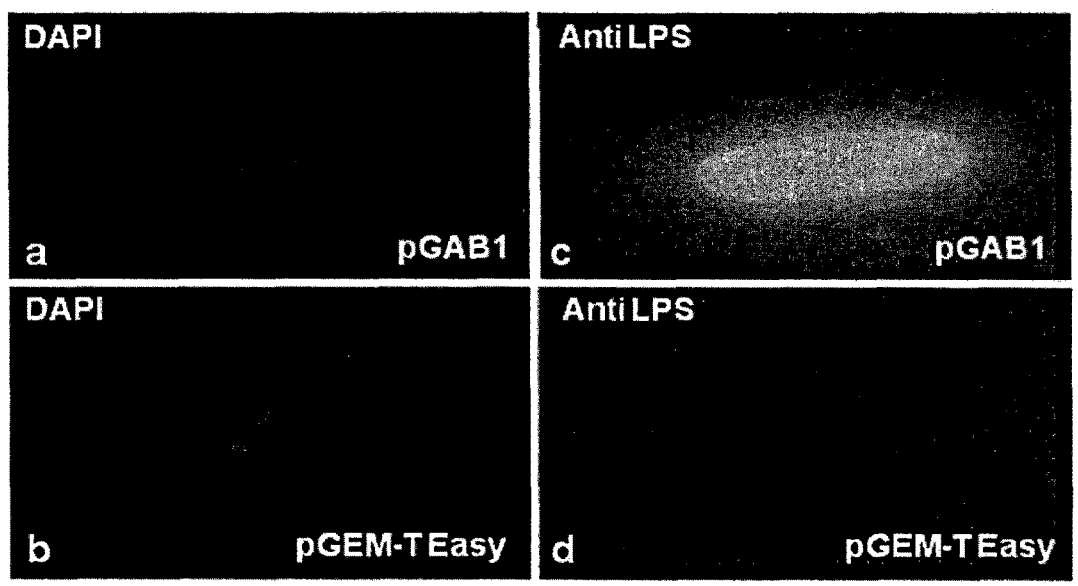
FIG. 2: *F. tularensis* SchuS4 O-antigen is expressed in *E. coli* DH5α cells. *E. coli* cells carrying the *F. tularensis* vector pGAB1 (containing O-antigen coding region) and empty pGEM-T Easy vector respectively, stained with DAPI to visualise nucleic acid (panels a and b) and probed with mAb FB11 and Alexa Fluor® 488 conjugated secondary antibody (panels c and d). Images are shown at 100× magnification.

Example 1: Expression of the *F. Tularensis* SchuS4 O-Antigen in *E. Coli* DH5α Cells The 20 kb *F. tularensis* SchuS4 O-antigen coding region was PCR amplified and cloned into pGEM-T Easy to generate the plasmid pGAB1. All bacterial strains and vectors used in this study are summarized in table 1. To confirm O-antigen expression and transport to the outer cell surface of *E. coli*, pGAB1 was transformed into DH5α cells and probed by immunofluorescence using mAb FB11, specific to the *F. tularensis* O-antigen. FIG. 2C demonstrates the expression of the O-antigen on the surface of *E. coli* DH5α cells, which is absent in the vector alone control (FIG. 2D).

Figure 3:
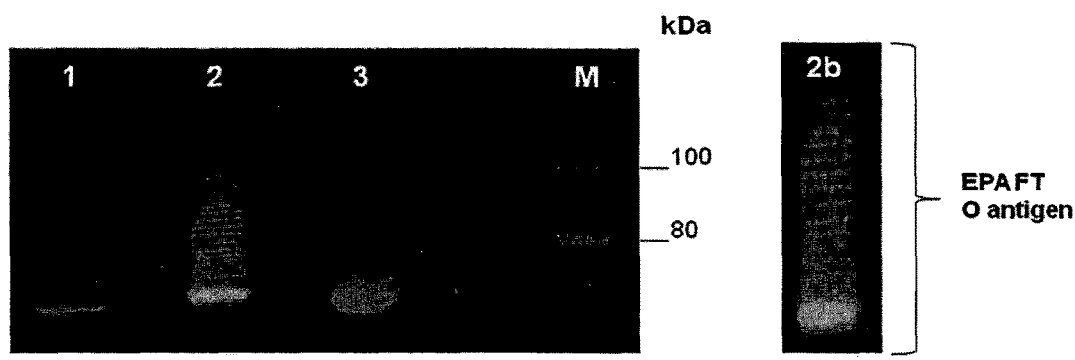
FIG. 3: *F. tularensis* O-antigen is conjugated to ExoA by CjPglB in *E. coli* CLM24 cells. Two colour immunoblots performed on HIS tag purified ExoA using mouse mAbFB11 and rabbit anti 6×HIS tag antibody. Lane 1, *E. coli* CLM24 carrying pGAB2, pGVXN150, pGVXN115 (non-functional CjPglB control); lane 2, pGAB2, pGVXN150, pGVXN114 (functional CjPglB); lane 3, pGVXN150 only; Panel 2b, close up view of HIS-tagged purified ExoA attached to various chain lengths of *F. tularensis* O-antigen. M=marker IRDye® 680/800 protein marker. pGVXN150 contains ExoA, pGAB2 contains *F. tularensis* O-antigen, pGVXN114 and pGVXN115 carry a functional and non-functional CjPglB respectively.

Example 2: CjPglB can Transfer *F. Tularensis* O-Antigen to the Acceptor Protein Exotoxin A In order to generate a strong T-cell response and lasting immunity, a highly immunogenic protein is required as a carrier for the *F. tularensis* O-antigen. The selected carrier protein was an inactivated form of the *P. aeruginosa* Exotoxin A variant L552V, ΔE553 (ExoA) was selected [20]. The plasmid pGAB2 containing the *F. tularensis* O-antigen expressed in the low copy vector pLAFR1 [21] was transformed into *E. coli* CLM24 cells along with the plasmids pGVXN114 and pGVXN150 which contain CjPglB and ExoA respectively. As negative glycosylation controls, CLM24 cells were transformed with either pGVXN150 alone or with the combination of pGAB2, pGVXN150 and pGVXN115, the latter coding for an inactive version of CjPglB [18]. Following overnight induction of CjpglB and exoA expression with 1 mM IPTG and 0.2% L-arabinose (w/v) respectively, cells were lysed and HIS tagged ExoA purified using Nickel columns. Elution fractions from each sample were separated by SDS PAGE and tested by immunoblotting with mAbFB011 specific for *F. tularensis* LPS. A band matching the expected size of ExoA and an O-antigen ladder pattern could only be seen when a functional CjPglB was present (FIG. 3, lanes 2 and 2b). In the absence of a functional CjPglB there was no cross-reaction with mAbFB11 (FIG. 3, lanes 1 and 3). To demonstrate that the O-antigen was bound to the carrier protein, HIS tagged ExoA *F. tularensis* O-antigen conjugate was purified and digested with Proteinase K. The disappearance of the O-antigen ladder after Proteinase K treatment but not in the untreated control confirmed that the O-antigen was anchored to ExoA (data not shown).

Figure 4:
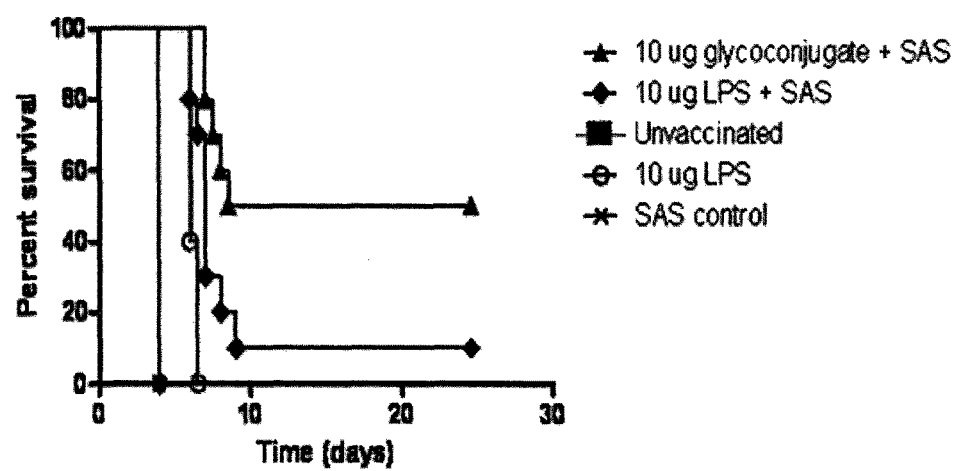
FIG. 4: Vaccination with test glycoconjugate increases host survival compared to LPS and controls. Balb/C mice were vaccinated with three doses of 10 ug glycoconjugate+ SAS, LPS+SAS or 10 μg LPS (n=10 per group). Mice were challenged 5 weeks following final vaccination with 100

Example 3: Vaccination with the Glycoconjugate Provides Significant Protection Against *F. Tularensis* Subsp. *Holarctica* Infection in Mice In a pilot study we compared LPS alone against the glycoconjugate vaccine and monitored antibody levels and murine survival. The Sigma Adjuvant System® was selected for use in this study because it is based on monophosphoryl lipid A (MPL), a low toxicity derivative of LPS that has been demonstrated to be a safe and effective immunostimulant [22]. In order to demonstrate the specificity of the glycoconjugate we used controls including mice with SAS adjuvant alone, unvaccinated mice and mice vaccinated with a 'sham' glycoconjugate control (*C. jejuni* heptasaccharide conjugated to ExoA). Only mice vaccinated with 0.5 μg test glycoconjugate+SAS (P<0.05) or 0.5 μg LPS (P<0.001) demonstrated increased survival compared to the appropriate controls as determined by log rank test (FIG. 22). These candidates were selected for further assessment at higher doses and an additional group consisting of LPS+SAS was also added as a further control. Protection was compared between mice immunised with either 10 μg glycoconjugate+SAS, 10 μg LPS or 10 μg LPS+SAS. All three vaccines were protective when compared to the unvaccinated mice (P<0.001), while the SAS adjuvant alone did not elicit any protection (P>0.05) (FIG. 4). This experiment also indicated that LPS+SAS did not elicit the same level of protection as the glycoconjugate+SAS combination (P<0.05) and thereafter LPS+SAS was deemed unnecessary for testing. The study was repeated in order to provide further bacterial organ load and immunological response data and no statistically significant difference was found between replicates.

Example 4: Mice Vaccinated with Test Glycoconjugate and Challenged with *F. Tularensis* Subsp. *Holarctica* Have Lower Bacterial Loads and Pro-Inflammatory Cytokines 3 Days Post Challenge Three days post challenge 5 mice per group were sacrificed and bacterial loads in the spleens and inflammatory responses were evaluated (FIG. 5). FIG. 5 shows the bacterial loads from vaccine with 10 μg of each candidate. Mice that were immunised with the glycoconjugate+SAS or LPS both had significantly decreased bacterial loads in spleens (P<0.01) when compared to the SAS and unvaccinated controls. Mice vaccinated with glycoconjugate+SAS had significantly less bacteria compared to those vaccinated with LPS alone (P<0.05). Inflammatory cytokine profiles between the different vaccine groups were also analysed (FIG. 6). Reduced levels of inflammatory cytokines were seen in mice vaccinated with glycoconjugate+SAS and LPS alone (P<0.05), corresponding with decreased bacterial loads. There was no significant difference between cytokine profiles for both experiments (P>0.05).

Example 5: Vaccination with the *F. Tularensis* Glycoconjugate Induces a Greater IgG Immune Response The levels of LPS-specific IgG were assessed in mice 7 days prior to challenge for both experiments. Increased LPS-specific IgG was observed in the glycoconjugate+SAS vaccinated group when compared to animals vaccinated with LPS only (P<0.001). Although experiment 2 had higher levels of antibody (P<0.01), we observed no difference in pattern between experiments (P>0.05) (FIG. 7). No significant differences were observed between LPS-specific IgM levels from the glycoconjugate and LPS vaccine groups (FIG. 23).

REFERENCES

1. Shinefield H R, Black S, Ray P, et al. Safety and immunogenicity of heptavalent pneumococcal CRM197 conjugate vaccine in infants and toddlers. The Pediatric infectious disease journal 1999; 18:757-63.
2. Grijalva C G, Nuorti J P, Arbogast P G, Martin S W, Edwards K M, Griffin M R. Decline in pneumonia admissions after routine childhood immunisation with pneumococcal conjugate vaccine in the USA: a time-series analysis. Lancet 2007; 369:1179-86.
3. Theodoratou E, Johnson S, Jhass A, et al. The effect of *Haemophilus influenzae* type b and pneumococcal conjugate vaccines on childhood pneumonia incidence, severe morbidity and mortality. International journal of epidemiology 2010; 39 Suppl 1:i172-85.
4. Sucher A J, Chahine E B, Nelson M, Sucher B J. Prevnar 13, the new 13-valent pneumococcal conjugate vaccine. The Annals of pharmacotherapy 2011; 45:1516-24.
5. Feldman M F, Wacker M, Hernandez M, et al. Engineering N-linked protein glycosylation with diverse O antigen lipopolysaccharide structures in *Escherichia coli*. Proceedings of the National Academy of Sciences of the United States of America 2005; 102:3016-21.
6. Terra V S, Mills D C, Yates L E, Abouelhadid S, Cuccui J, Wren B W. Recent developments in bacterial protein glycan coupling technology and glycoconjugate vaccine design. Journal of medical microbiology 2012; 61:919-26.
7. Langdon R H, Cuccui J, Wren B W. N-linked glycosylation in bacteria: an unexpected application. Future microbiology 2009; 4:401-12.
8. Dennis D T, Inglesby T V, Henderson D A, et al. Tularemia as a biological weapon: medical and public health management. JAMA: the journal of the American Medical Association 2001; 285:2763-73.
9. Reintjes R, Dedushaj I, Gjini A, et al. Tularemia outbreak investigation in Kosovo: case control and environmental studies. Emerging infectious diseases 2002; 8:69-73.
10. McCrumb F R. Aerosol Infection of Man with *Pasteurella Tularensis*. Bacteriological reviews 1961; 25:262-7.
11. Oyston P C, Sjostedt A, Titball R W. Tularaemia: bioterrorism defence renews interest in *Francisella tularensis*. Nature reviews Microbiology 2004; 2:967-78.
12. Fulop M, Manchee R, Titball R. Role of lipopolysaccharide and a major outer membrane protein from *Francisella tularensis* in the induction of immunity against tularemia. Vaccine 1995; 13:1220-5.
13. Weintraub A. Immunology of bacterial polysaccharide antigens. Carbohydrate research 2003; 338:2539-47.
14. Fulop M, Mastroeni P, Green M, Titball R W. Role of antibody to lipopolysaccharide in protection against low- and high-virulence strains of *Francisella tularensis*. Vaccine 2001; 19:4465-72.
15. Conlan J W, Shen H, Webb A, Perry M B. Mice vaccinated with the O-antigen of *Francisella tularensis* LVS lipopolysaccharide conjugated to bovine serum albumin develop varying degrees of protective immunity against systemic or aerosol challenge with virulent type A and type B strains of the pathogen. Vaccine 2002; 20:3465-71.
16. Prior J L, Prior R G, Hitchen P G, et al. Characterization of the O antigen gene cluster and structural analysis of the O antigen of *Francisella tularensis* subsp. *tularensis*. Journal of medical microbiology 2003; 52:845-51.
17. Cuccui J, Milne T S, Harmer N, et al. Characterization of the *Burkholderia pseudomallei* K96243 capsular polysaccharide I coding region. Infection and immunity 2012; 80:1209-21.
18. Wacker M, Linton D, Hitchen P G, et al. N-linked glycosylation in *Campylobacter jejuni* and its functional transfer into *E. coli*. Science 2002; 298:1790-3.
19. Eyles J E, Hartley M G, Laws T R, Oyston P C, Griffin K F, Titball R W. Protection afforded against aerosol challenge by systemic immunisation with inactivated *Francisella tularensis* live vaccine strain (LVS). Microbial pathogenesis 2008; 44:164-8.
20. Ihssen J, Kowarik M, Dilettoso S, Tanner C, Wacker M, Thony-Meyer L. Production of glycoprotein vaccines in *Escherichia coli*. Microbial cell factories 2010; 9:61.
21. Friedman A M, Long S R, Brown S E, Buikema W J, Ausubel F M. Construction of a broad host range cosmid cloning vector and its use in the genetic analysis of *Rhizobium* mutants. Gene 1982; 18:289-96.
22. Pedersen C, Petaja T, Strauss G, et al. Immunization of early adolescent females with human papillomavirus type 16 and 18 L1 virus-like particle vaccine containing AS04 adjuvant. The Journal of adolescent health: official publication of the Society for Adolescent Medicine 2007; 40:564-71.
23. Fisher A C, Haitjema C H, Guarino C, et al. Production of secretory and extracellular N-linked glycoproteins in *Escherichia coli*. Applied and environmental microbiology 2011; 77:871-81.

The invention claimed is:

1. A vaccine or immunogenic composition, comprising:
   a carrier polypeptide comprising an amino acid sequence set forth in SEQ ID NO: 1; and
   an antigenic O-antigen polysaccharide isolated from *Francisella* crosslinked to the carrier polypeptide.

2. The vaccine or immunogenic composition according to claim 1 wherein said O-antigen polysaccharide comprises 4)-α-D-GalNAcAN-(1-4)-α-D-GalNAcAN-(1-3)-β-D-QuiNAc-(1-2)-β-D-Qui4NFm-(1-), wherein GalNAcAN is 2-acetamido-2-deoxy-O-D-galact-uronamide, 4NFm is 4,6-dideoxy-4-formamido-D-glucose and the reducing end group QuiNAc is 2-acetamido-2,6-dideoxy-O-D-glucose.

3. The vaccine or immunogenic composition according to claim 1, wherein said O-antigen polysaccharide is a tetrasaccharide.

4. The vaccine or immunogenic composition according to claim 1, wherein said composition further includes an adjuvant.

5. The vaccine or immunogenic composition according to claim 1, wherein said composition further includes at least one anti-bacterial agent.

6. The vaccine or immunogenic composition according to claim 5 wherein said at least one anti-bacterial agent is not an antigenic O-antigen polysaccharide isolated from *Francisella*.

7. The vaccine or immunogenic composition according to claim 6 wherein said composition is a multivalent antigenic composition.

8. The vaccine or immunogenic composition according to claim 5 wherein said at least one anti-bacterial agent comprises an antibiotic.

9. A method of treating a *Francisella* infection, comprising:
   administering an effective amount of the vaccine or immunogenic composition according to claim 1.

10. The method according to claim 9 wherein said infection is caused by *Francisella tularensis*.

11. A modified bacterial cell wherein said cell is genetically modified to include:
   i) a nucleic acid molecule comprising the nucleotide sequence of the *Francisella* O-antigen biosynthetic polysaccharide locus as shown in SEQ ID NO: 7;
   ii) a nucleic acid molecule comprising a nucleotide sequence of an oligosaccharyltransferase as shown in SEQ ID NO: 8 or a functional variant thereof, wherein said variant comprises a nucleic acid molecule the complementary strand of which hybridizes under stringent hybridization conditions to the sequence set forth in SEQ ID NO: 8, and wherein said nucleic acid molecule encodes an oligosaccharyltransferase; and/or
   iii) a nucleic acid molecule comprising a nucleotide sequence of a carrier polypeptide, wherein the carrier polypeptide comprises one or more T-cell dependent epitopes and one or more amino acid sequences having the amino acid motif D/E-X-N-X-S/T, wherein X is any amino acid except proline, wherein said bacterial cell is adapted for expression of each nucleic acid molecule and synthesizes an antigenic polypeptide.

12. The modified bacterial cell according to claim 11, wherein at least the oligosaccharyltransferase of ii) is integrated into the bacterial genome.

13. The modified bacterial cell of claim 11, wherein one or more nucleic acid molecules encoding the carrier polypeptides are integrated into the bacterial genome.

14. A bacterial cell culture comprising a genetically modified bacterial cell according to claim 11.

15. A process for the production of one or more glycoconjugates comprising:
  i) providing a bacterial cell culture according to claim 14;
  ii) providing cell culture conditions; and
  iii) isolating one or more glycoconjugates from the bacterial cell or cell culture medium.

16. A cell culture vessel comprising a bacterial cell culture according to claim 14.

17. The cell culture vessel according to claim 16 wherein said cell culture vessel is a fermentor.

18. A vaccine or immunogenic composition, comprising:
  a carrier polypeptide comprising an amino acid sequence set forth in SEQ ID NO: 2, 3, 4, 5 or 6; and
  an antigenic O-antigen polysaccharide isolated from *Francisella* crosslinked to the carrier polypeptide.

19. A method of treating a *Francisella* infection, comprising:
  administering an effective amount of the vaccine or immunogenic composition according to claim 18.

* * * * *

SEQUENCE LISTING

```
<160> NUMBER OF SEQ ID NOS: 17

<210> SEQ ID NO 1
<211> LENGTH: 697
<212> TYPE: PRT
<213> ORGANISM: Pseudomonas aeruginosa

<400> SEQUENCE: 1

Met Lys Lys Ile Trp Leu Ala Leu Ala Gly Leu Val Leu Ala Phe Ser
1               5                   10                  15

Ala Ser Asp Gln Asn Ala Thr Gly Gly Asp Gln Asn Ala Thr Gly Gly
            20                  25                  30
```

```
Asp Gln Asn Ala Thr Gly Gly Asp Gln Asn Ala Thr Ala Glu Glu
         35                  40                  45

Ala Phe Asp Leu Trp Asn Glu Cys Ala Lys Ala Cys Val Leu Asp Leu
 50                      55                  60

Lys Asp Gly Val Arg Ser Ser Arg Met Ser Val Asp Pro Ala Ile Ala
 65                  70                  75                  80

Asp Thr Asn Gly Gln Gly Val Leu His Tyr Ser Met Val Leu Glu Gly
                 85                  90                  95

Gly Asn Asp Ala Leu Lys Leu Ala Ile Asp Asn Ala Leu Ser Ile Thr
            100                 105                 110

Ser Asp Gly Leu Thr Ile Arg Leu Glu Gly Gly Val Glu Pro Asn Lys
        115                 120                 125

Pro Val Arg Tyr Ser Tyr Thr Arg Gln Ala Arg Gly Ser Trp Ser Leu
    130                 135                 140

Asn Trp Leu Val Pro Ile Gly His Glu Lys Pro Ser Asn Ile Lys Val
145                 150                 155                 160

Phe Ile His Glu Leu Asn Ala Gly Asn Gln Leu Ser His Met Ser Pro
                165                 170                 175

Ile Tyr Thr Ile Glu Met Gly Asp Glu Leu Leu Ala Lys Leu Ala Arg
            180                 185                 190

Asp Ala Thr Phe Phe Val Arg Ala His Glu Ser Asn Glu Met Gln Pro
        195                 200                 205

Thr Leu Ala Ile Ser His Ala Gly Val Ser Val Met Ala Gln Ala
    210                 215                 220

Gln Pro Arg Arg Glu Lys Arg Trp Ser Glu Trp Ala Ser Gly Lys Val
225                 230                 235                 240

Leu Cys Leu Leu Asp Pro Leu Asp Gly Val Tyr Asn Tyr Leu Ala Gln
                245                 250                 255

Gln Arg Cys Asn Leu Asp Asp Thr Trp Glu Gly Lys Ile Tyr Arg Val
            260                 265                 270

Leu Ala Gly Asn Pro Ala Lys His Asp Leu Asp Ile Lys Asp Asn Asn
        275                 280                 285

Asn Ser Thr Pro Thr Val Ile Ser His Arg Leu His Phe Pro Glu Gly
    290                 295                 300

Gly Ser Leu Ala Ala Leu Thr Ala His Gln Ala Cys His Leu Pro Leu
305                 310                 315                 320

Glu Ala Phe Thr Arg His Arg Gln Pro Arg Gly Trp Glu Gln Leu Glu
                325                 330                 335

Gln Cys Gly Tyr Pro Val Gln Arg Leu Val Ala Leu Tyr Leu Ala Ala
            340                 345                 350

Arg Leu Ser Trp Asn Gln Val Asp Gln Val Ile Arg Asn Ala Leu Ala
        355                 360                 365

Ser Pro Gly Ser Gly Gly Asp Leu Gly Glu Ala Ile Arg Glu Gln Pro
    370                 375                 380

Glu Gln Ala Arg Leu Ala Leu Thr Leu Ala Ala Ala Glu Ser Glu Arg
385                 390                 395                 400

Phe Val Arg Gln Gly Thr Gly Asn Asp Glu Ala Gly Ala Ala Ser Ala
                405                 410                 415

Asp Val Val Ser Leu Thr Cys Pro Val Ala Lys Asp Gln Asn Arg Thr
            420                 425                 430

Lys Gly Glu Cys Ala Gly Pro Ala Asp Ser Gly Asp Ala Leu Leu Glu
        435                 440                 445
```

```
Arg Asn Tyr Pro Thr Gly Ala Glu Phe Leu Gly Asp Gly Gly Asp Val
    450             455                 460

Ser Phe Ser Thr Arg Gly Thr Gln Asn Trp Thr Val Glu Arg Leu Leu
465             470                 475                 480

Gln Ala His Arg Gln Leu Glu Glu Arg Gly Tyr Val Phe Val Gly Tyr
            485                 490                 495

His Gly Thr Phe Leu Glu Ala Ala Gln Ser Ile Val Phe Gly Gly Val
        500                 505                 510

Arg Ala Arg Ser Gln Asp Leu Asp Ala Ile Trp Arg Gly Phe Tyr Ile
    515                 520                 525

Ala Gly Asp Pro Ala Leu Ala Tyr Gly Tyr Ala Gln Asp Gln Glu Pro
    530                 535                 540

Asp Ala Arg Gly Arg Ile Arg Asn Gly Ala Leu Leu Arg Val Tyr Val
545             550                 555                 560

Pro Arg Trp Ser Leu Pro Gly Phe Tyr Arg Thr Gly Leu Thr Leu Ala
            565                 570                 575

Ala Pro Glu Ala Ala Gly Glu Val Glu Arg Leu Ile Gly His Pro Leu
            580                 585                 590

Pro Leu Arg Leu Asp Ala Ile Thr Gly Pro Glu Glu Glu Gly Gly Arg
            595                 600                 605

Val Thr Ile Leu Gly Trp Pro Leu Ala Glu Arg Thr Val Val Ile Pro
            610                 615                 620

Ser Ala Ile Pro Thr Asp Pro Arg Asn Val Gly Asp Leu Asp Pro
625             630                 635                 640

Ser Ser Ile Pro Asp Lys Glu Gln Ala Ile Ser Ala Leu Pro Asp Tyr
            645                 650                 655

Ala Ser Gln Pro Gly Lys Pro Pro Arg Glu Asp Leu Lys Asp Gln Asn
            660                 665                 670

Ala Thr Gly Gly Asp Gln Asn Ala Thr Gly Gly Asp Gln Asn Ala Thr
            675                 680                 685

Gly Gly Asp Gln Asn Ala Thr Val Asp
            690                 695

<210> SEQ ID NO 2
<211> LENGTH: 225
<212> TYPE: PRT
<213> ORGANISM: Francisella tularensis

<400> SEQUENCE: 2

Met Lys Lys Ile Trp Leu Ala Leu Ala Gly Leu Val Leu Ala Phe Ser
1               5                   10                  15

Ala Ser Gly Thr Asp Gln Asn Ala Thr Gly Gly Asp Gln Asn Ala Thr
            20                  25                  30

Gly Gly Asp Gln Asn Ala Thr Gly Gly Asp Gln Asn Ala Thr Gly Thr
            35                  40                  45

Met Lys Lys Ile Ile Glu Leu Ser Leu Leu Ser Leu Ser Ile Ala Gly
        50                  55                  60

Leu Ala Ser Cys Ser Thr Leu Gly Leu Gly Gly Ser Asp Asp Ala Lys
65              70                  75                  80

Ala Ser Ala Lys Asp Thr Ala Ala Gln Thr Ala Thr Thr Glu Gln
            85                  90                  95

Ala Ala Ala Val Ser Lys Pro Thr Ala Lys Val Ser Leu Asn Lys Leu
            100                 105                 110

Gly Gln Asp Lys Ile Lys Ala Thr Val Tyr Thr Thr Tyr Asn Asn Asn
        115                 120                 125
```

```
Pro Gln Gly Ser Val Arg Leu Gln Trp Gln Ala Pro Glu Gly Ser Lys
    130                 135                 140

Cys His Asp Thr Ser Phe Pro Ile Thr Lys Tyr Ala Glu Lys Asn Asp
145                 150                 155                 160

Lys Thr Trp Ala Thr Val Thr Val Lys Gln Gly Asn Asn Phe Cys Ser
                165                 170                 175

Gly Lys Trp Thr Ala Asn Val Val Tyr Asp Lys Glu Val Ile Ala Ser
                180                 185                 190

Asp Ser Ile Asn Ile Asp Gln Asn Ala Thr Gly Gly Asp Gln Asn Ala
                195                 200                 205

Thr Gly Gly Asp Gln Asn Ala Thr Gly Gly Asp Gln Asn Ala Thr Val
    210                 215                 220

Asp
225

<210> SEQ ID NO 3
<211> LENGTH: 590
<212> TYPE: PRT
<213> ORGANISM: Francisella tularensis

<400> SEQUENCE: 3

Met Lys Lys Ile Trp Leu Ala Leu Ala Gly Leu Val Leu Ala Phe Ser
1               5                   10                  15

Ala Ser Gly Thr Asp Gln Asn Ala Thr Gly Gly Asp Gln Asn Ala Thr
                20                  25                  30

Gly Gly Asp Gln Asn Ala Thr Gly Gly Asp Gln Asn Ala Thr Gly Thr
                35                  40                  45

Met Val Ser Arg Glu Asp Phe Ile Met Thr Ile Asn Lys Leu Ser Leu
50                  55                  60

Thr Asp Glu Leu Leu Asn Asn Phe Gly Gly Ser Thr Glu Val Asp Ser
65                  70                  75                  80

Val Leu Lys Asn Ile Asp Phe Asp Val Ser Asp Ala Ser Lys Val
                85                  90                  95

Leu Ser Leu Ser Thr Asp Tyr Asn Ala Arg Asn Leu Met Ala Leu Ser
                100                 105                 110

Leu Val Leu Ala Asn Asn Asp Asn Ile Asn Asn Tyr Asn Gln Lys Tyr
            115                 120                 125

Ile Gln Lys Val Ile Thr Val Ile Asp Lys Leu Ile Asp Leu Gln Val
    130                 135                 140

Asn Ser Ile Ile Ser Asn Asp Glu Phe Arg Ala Leu Glu Gln Glu Trp
145                 150                 155                 160

Leu Lys Val Gln Glu Val Cys Gln Glu Asp Tyr Asp Asn Val Glu Val
                165                 170                 175

Ser Ile Leu Asp Val Lys Lys Glu Leu Gln Tyr Asp Phe Glu Arg
                180                 185                 190

Asn Leu Tyr Asp Ile Ser Ser Ser Asp Phe Lys Lys Val Tyr Val
                195                 200                 205

Ser Glu Phe Asp Gln Tyr Gly Gly Glu Pro Tyr Gly Ala Ile Leu Gly
    210                 215                 220

Leu Tyr Asn Phe Glu Asn Thr Asn Asp Ile Ile Trp Leu Thr Gly
225                 230                 235                 240

Met Gly Met Val Ala Lys Asn Ser His Ala Pro Phe Ile Ala Ser Ile
                245                 250                 255

Asp Lys Ser Phe Phe Gly Val Lys Asp Leu Ser Glu Ile Thr His Ile
                260                 265                 270
```

```
Lys Ser Phe Glu Ala Leu Leu Glu His Pro Arg Tyr Lys Glu Trp Asn
            275                 280                 285

Asp Phe Arg Asn Leu Asp Val Ala Ala Tyr Ile Gly Leu Thr Val Gly
            290                 295                 300

Asp Phe Met Leu Arg Gln Pro Tyr Asn Pro Glu Asn Asn Pro Val Gln
305                 310                 315                 320

Tyr Lys Leu Met Glu Gly Phe Asn Glu Phe Val Asp Tyr Asp Lys Asn
            325                 330                 335

Glu Ser Tyr Leu Trp Gly Pro Ala Ser Ile His Leu Val Lys Asn Met
            340                 345                 350

Met Arg Ser Tyr Asp Lys Thr Arg Trp Phe Gln Tyr Ile Arg Gly Val
            355                 360                 365

Glu Ser Gly Gly Tyr Val Lys Asn Leu Val Ala Cys Val Tyr Asp Asn
            370                 375                 380

Lys Gly Ile Leu Glu Thr Lys Ser Pro Leu Asn Val Leu Phe Ala Asp
385                 390                 395                 400

Tyr Met Glu Leu Ser Leu Ala Asn Ile Gly Leu Ile Pro Phe Val Ser
            405                 410                 415

Glu Lys Gly Thr Ser Asn Ala Cys Phe Phe Ser Val Asn Ser Ala Lys
            420                 425                 430

Lys Val Glu Glu Phe Val Asp Gly Phe Asp Ser Ala Asn Ser Arg Leu
            435                 440                 445

Ile Ala Asn Leu Ser Tyr Thr Met Cys Ile Ser Arg Ile Ser His Tyr
            450                 455                 460

Ile Lys Cys Val Ile Arg Asp Lys Ile Gly Ser Ile Val Asp Val Glu
465                 470                 475                 480

Ser Ile Gln Lys Ile Leu Ser Asp Trp Ile Ser Glu Phe Val Thr Thr
            485                 490                 495

Val Tyr Gln Pro Thr Pro Leu Glu Met Ala Arg Tyr Pro Phe Arg Asn
            500                 505                 510

Val Ser Ile Glu Val Glu Thr Ile Pro Gly Lys Pro Gly Trp Tyr Ser
            515                 520                 525

Cys Lys Ile Asn Val Ile Pro His Ile Gln Phe Glu Gly Met Asn Thr
            530                 535                 540

Thr Met Thr Ile Asp Thr Arg Leu Glu Pro Glu Leu Phe Gly Thr Asn
545                 550                 555                 560

Asn Asn Asp Gln Asn Ala Thr Gly Gly Asp Gln Asn Ala Thr Gly Gly
            565                 570                 575

Asp Gln Asn Ala Thr Gly Gly Asp Gln Asn Ala Thr Val Asp
            580                 585                 590

<210> SEQ ID NO 4
<211> LENGTH: 171
<212> TYPE: PRT
<213> ORGANISM: Francisella tularensis

<400> SEQUENCE: 4

Met Lys Lys Ile Trp Leu Ala Leu Ala Gly Leu Val Leu Ala Phe Ser
1               5                   10                  15

Ala Ser Gly Thr Asp Gln Asn Ala Thr Gly Gly Asp Gln Asn Ala Thr
            20                  25                  30

Gly Gly Asp Gln Asn Ala Thr Gly Gly Asp Gln Asn Ala Thr Gly Thr
            35                  40                  45

Met Asn Ile Arg Pro Leu Gln Asp Arg Val Leu Val Arg Arg Ala Glu
            50                  55                  60
```

```
Glu Glu Lys Lys Ser Ala Gly Gly Ile Ile Leu Thr Gly Ser Ala Gln
65                  70                  75                  80

Glu Lys Pro Ser Gln Gly Glu Val Val Ala Val Gly Asn Gly Lys Lys
            85                  90                  95

Leu Asp Asn Gly Thr Thr Leu Pro Met Asp Val Lys Val Gly Asp Lys
            100                 105                 110

Val Leu Phe Gly Lys Tyr Ser Gly Ser Glu Val Lys Val Gly Asp Glu
        115                 120                 125

Thr Leu Leu Met Met Arg Glu Asp Ile Met Gly Ile Ile Ala Asp
    130                 135                 140

Gln Asn Ala Thr Gly Gly Asp Gln Asn Ala Thr Gly Gly Asp Gln Asn
145                 150                 155                 160

Ala Thr Gly Gly Asp Gln Asn Ala Thr Val Asp
            165                 170

<210> SEQ ID NO 5
<211> LENGTH: 718
<212> TYPE: PRT
<213> ORGANISM: Francisella tularensis

<400> SEQUENCE: 5

Met Lys Lys Ile Trp Leu Ala Leu Ala Gly Leu Val Leu Ala Phe Ser
1               5                   10                  15

Ala Ser Gly Thr Asp Gln Asn Ala Thr Gly Gly Asp Gln Asn Ala Thr
            20                  25                  30

Gly Gly Asp Gln Asn Ala Thr Gly Gly Asp Gln Asn Ala Thr Gly Thr
        35                  40                  45

Met Gly Lys Ile Ile Gly Ile Asp Leu Gly Thr Thr Asn Ser Cys Leu
50                  55                  60

Ala Ile Met Asp Gly Lys Thr Ala Lys Val Ile Glu Asn Ala Glu Gly
65                  70                  75                  80

His Arg Thr Thr Pro Ser Val Val Ala Tyr Thr Asp Ser Gly Glu Ile
            85                  90                  95

Leu Val Gly Gln Ala Ala Lys Arg Gln Ala Val Thr Asn Pro Asp Asn
        100                 105                 110

Thr Phe Phe Ala Ile Lys Arg Leu Ile Gly Arg Lys Tyr Asp Asp Lys
    115                 120                 125

Ala Val Gln Glu Asp Ile Lys Lys Val Pro Tyr Ala Val Ile Lys
130                 135                 140

Ala Asp Asn Gly Asp Ala Trp Val Ala Thr Lys Glu Gly Lys Lys Met
145                 150                 155                 160

Ala Pro Pro Gln Val Ser Ala Glu Val Leu Arg Lys Met Lys Lys Thr
            165                 170                 175

Ala Glu Asp Tyr Leu Gly Glu Pro Thr Glu Ala Val Ile Thr Val
        180                 185                 190

Pro Ala Tyr Phe Asn Asp Ser Gln Arg Gln Ala Thr Lys Asp Ala Gly
    195                 200                 205

Lys Ile Ala Gly Leu Glu Val Lys Arg Ile Ile Asn Glu Pro Thr Ala
210                 215                 220

Ala Ala Leu Ala Tyr Gly Val Asp Ser Lys Lys Gly Glu Gln Thr Val
225                 230                 235                 240

Ala Val Tyr Asp Leu Gly Gly Gly Thr Phe Asp Ile Ser Ile Ile Glu
            245                 250                 255

Ile Ala Asp Val Asp Gly Asp Asn Gln Ile Glu Val Leu Ser Thr Asn
        260                 265                 270
```

-continued

```
Gly Asp Thr Phe Leu Gly Gly Glu Asp Phe Asp Leu Ala Leu Met Asn
            275                 280                 285

Tyr Leu Ile Asp Glu Phe Lys Lys Glu Gln Gly Ile Asp Leu His Asn
        290                 295                 300

Asp Lys Leu Ala Leu Gln Arg Val Arg Glu Ala Ala Glu Lys Ala Lys
305                 310                 315                 320

Val Glu Leu Ser Ser Ala Gln Gln Thr Asp Val Asn Leu Pro Tyr Ile
                325                 330                 335

Thr Ala Asp Ala Thr Gly Pro Lys His Leu Asn Ile Lys Val Thr Arg
            340                 345                 350

Ala Lys Phe Glu Ser Leu Val Ser Asp Leu Val Met Arg Ser Leu Glu
        355                 360                 365

Pro Cys Lys Lys Ala Leu Glu Asp Ala Gly Leu Ser Lys Ser Asp Ile
    370                 375                 380

Thr Glu Val Leu Leu Val Gly Gly Gln Thr Arg Met Pro Leu Val Gln
385                 390                 395                 400

Glu Lys Val Lys Glu Phe Phe Gly Lys Glu Pro Arg Lys Asp Val Asn
                405                 410                 415

Pro Asp Glu Ala Val Ala Val Gly Ala Ala Ile Gln Gly Gly Val Leu
            420                 425                 430

Ala Gly Asp Val Lys Asp Ile Leu Leu Leu Asp Val Thr Pro Leu Ser
        435                 440                 445

Leu Gly Ile Glu Thr Met Gly Gly Val Met Thr Lys Leu Ile Glu Arg
    450                 455                 460

Asn Thr Thr Ile Pro Thr Lys Lys Ser Gln Val Phe Ser Thr Ala Glu
465                 470                 475                 480

Asp Asn Gln Pro Ala Val Thr Ile His Val Leu Gln Gly Glu Arg Glu
                485                 490                 495

Met Ala Ser Ala Asn Lys Ser Leu Gly Arg Phe Asp Leu Ala Asp Ile
            500                 505                 510

Pro Pro Ala Pro Arg Gly Met Pro Gln Ile Glu Val Thr Phe Asp Ile
        515                 520                 525

Asp Ala Asn Gly Ile Leu Asn Val Ser Ala Lys Asp Lys Ala Thr Gly
    530                 535                 540

Lys Glu Gln Asn Ile Val Ile Lys Ser Ser Ser Gly Leu Ser Glu Glu
545                 550                 555                 560

Asp Ile Glu Lys Met Val Gln Asp Ala Glu Ala Asn Ala Glu Ala Asp
                565                 570                 575

Lys Lys Phe His Asp Leu Val Thr Ala Arg Asn Thr Ala Asp Asn Leu
            580                 585                 590

Ile His Ser Ser Arg Lys Ala Ile Gln Glu Leu Gly Asp Lys Val Thr
        595                 600                 605

Ala Ala Glu Lys Glu Lys Ile Glu Glu Ala Cys Lys Glu Leu Glu Ala
    610                 615                 620

Ala Thr Lys Gly Asp Asp Lys Gln Ala Ile Glu Ser Lys Thr Lys Ala
625                 630                 635                 640

Leu Glu Glu Ala Phe Ala Pro Ile Ala Gln Lys Ala Tyr Ala Glu Gln
                645                 650                 655

Ala Gln Ala Ala Val Ala Gln Gly Gly Ala Lys Ala Glu Glu Pro Lys
            660                 665                 670

Lys Glu Glu Asp Val Val Asp Ala Asp Phe Glu Asp Val Glu Asp Asp
        675                 680                 685
```

Lys Lys Asp Gln Asn Ala Thr Gly Gly Asp Gln Asn Ala Thr Gly Gly
    690                 695                 700

Asp Gln Asn Ala Thr Gly Gly Asp Gln Asn Ala Thr Val Asp
705                 710                 715

<210> SEQ ID NO 6
<211> LENGTH: 620
<212> TYPE: PRT
<213> ORGANISM: Francisella tularensis

<400> SEQUENCE: 6

Met Lys Lys Ile Trp Leu Ala Leu Ala Gly Leu Val Leu Ala Phe Ser
1               5                   10                  15

Ala Ser Gly Thr Asp Gln Asn Ala Thr Gly Gly Asp Gln Asn Ala Thr
            20                  25                  30

Gly Gly Asp Gln Asn Ala Thr Gly Gly Asp Gln Asn Ala Thr Gly Thr
        35                  40                  45

Met Ala Ala Lys Gln Val Leu Phe Ser Asp Glu Ala Arg Ala Lys Met
50                  55                  60

Leu Asp Gly Val Asn Thr Leu Ala Asn Ala Val Lys Val Thr Leu Gly
65                  70                  75                  80

Pro Lys Gly Arg Asn Val Val Leu Asp Lys Ser Phe Gly Thr Pro Thr
                85                  90                  95

Ile Thr Lys Asp Gly Val Ser Val Ala Lys Glu Ile Glu Leu Glu Asp
            100                 105                 110

Lys Phe Glu Asn Met Gly Ala Gln Ile Val Lys Glu Val Ala Ser Lys
        115                 120                 125

Thr Ala Asp Val Ala Gly Asp Gly Thr Thr Thr Ala Thr Val Leu Ala
130                 135                 140

Gln Ala Leu Leu Thr Glu Gly Leu Lys Ala Val Ala Ala Gly Met Asn
145                 150                 155                 160

Pro Met Asp Leu Lys Arg Gly Ile Asp Lys Ala Thr Ala Arg Leu Val
                165                 170                 175

Glu Glu Leu Lys Ala Leu Ser Lys Pro Cys Ser Asp Pro Lys Ser Ile
            180                 185                 190

Glu Gln Val Gly Thr Ile Ser Ala Asn Ser Asp Ala Thr Val Gly Lys
        195                 200                 205

Leu Ile Ala Asp Ala Met Ala Lys Val Gly Lys Glu Gly Val Ile Thr
210                 215                 220

Val Glu Glu Gly Lys Gly Phe Glu Asp Glu Leu Asp Val Val Glu Gly
225                 230                 235                 240

Met Gln Phe Asp Arg Gly Tyr Leu Ser Pro Tyr Phe Ala Thr Asn Gln
                245                 250                 255

Glu Asn Met Thr Thr Asp Leu Glu Asn Pro Tyr Ile Leu Ile Val Asp
            260                 265                 270

Lys Lys Ile Ser Asn Ile Arg Asp Leu Leu Pro Ile Leu Glu Gly Val
        275                 280                 285

Ser Lys Ser Gly Arg Ala Leu Leu Ile Ile Ala Glu Asp Val Glu Ser
290                 295                 300

Glu Ala Leu Ala Thr Leu Val Val Asn Asn Met Arg Gly Val Val Lys
305                 310                 315                 320

Val Cys Ala Val Lys Ala Pro Gly Phe Gly Asp Arg Arg Lys Ala Met
                325                 330                 335

Leu Glu Asp Ile Ala Thr Leu Thr Gly Ala Thr Phe Val Ser Glu Asp
            340                 345                 350

Leu Ser Met Lys Leu Glu Glu Thr Asn Met Glu His Leu Gly Thr Ala
            355                 360                 365

Ser Arg Val Gln Val Thr Lys Asp Asn Thr Thr Ile Ile Asp Gly Ala
        370                 375                 380

Gly Glu Lys Glu Ala Ile Ala Lys Arg Ile Asn Val Ile Lys Ala Asn
385                 390                 395                 400

Ile Ala Glu Ala Asn Ser Asp Tyr Asp Arg Glu Lys Leu Gln Glu Arg
                405                 410                 415

Leu Ala Lys Leu Ser Gly Gly Val Ala Val Ile Lys Val Gly Ala Val
            420                 425                 430

Thr Glu Ala Glu Met Lys Glu Lys Lys Asp Arg Val Asp Asp Ala Leu
        435                 440                 445

His Ala Thr Arg Ala Ala Val Glu Glu Gly Ile Val Ala Gly Gly Gly
    450                 455                 460

Val Ala Leu Ile Arg Ala Gln Lys Ala Leu Asp Gly Leu Thr Gly Glu
465                 470                 475                 480

Asn Asp Asp Gln Asn Tyr Gly Ile Ala Leu Leu Arg Lys Ala Ile Glu
                485                 490                 495

Ala Pro Leu Arg Gln Ile Val Ser Asn Ala Gly Gly Glu Ser Ser Val
            500                 505                 510

Val Val Asn Gln Val Lys Ala Asn Gln Gly Asn Tyr Gly Tyr Asn Ala
        515                 520                 525

Ala Asn Asp Thr Tyr Gly Asp Met Val Glu Met Gly Ile Leu Asp Pro
    530                 535                 540

Thr Lys Val Thr Arg Ser Ala Leu Gln His Ala Ala Ser Ile Ala Gly
545                 550                 555                 560

Leu Met Ile Thr Thr Glu Ala Met Ile Gly Glu Ile Lys Glu Ala Ala
                565                 570                 575

Pro Ala Met Pro Met Gly Gly Met Gly Met Gly Met Pro Gly Met Met
            580                 585                 590

Asp Gln Asn Ala Thr Gly Gly Asp Gln Asn Ala Thr Gly Gly Asp Gln
        595                 600                 605

Asn Ala Thr Gly Gly Asp Gln Asn Ala Thr Val Asp
    610                 615                 620

<210> SEQ ID NO 7
<211> LENGTH: 18852
<212> TYPE: DNA
<213> ORGANISM: Francisella tularensis

<400> SEQUENCE: 7
atgaattatc atataaaaga agtattctgg tcaattattt tatcattctt aaaatcacaa      60
aaaggtatac ataccaatga tgaagccaaa ttaagattgt ttattgaagc tgtatttat    120 gtgttacgta caggctgtca atggagaatg ttaccatttt attatggtaa atatagatca    180
atacataagc gttttaaaga ttggtgtgat aaagatatat tttctagatt atttaaatca    240
gtacaaaacc ctgatttaca agaagtcatg cttgattcaa caatagcaag agcacatgct    300
tgtgctacgg gatatgataa agatgataac caagcaattg gtagatcagt tggtaggata    360
accactaaaa tccatgctat gactgatgct ttaggtaatc caatagaaat attgttgtca    420
gaggataaaa ctcatgatag taaagtagct atagatttac taaaaaatgt atataataca    480
aaagttatcg ctgatagagc atatcattct aatgaaatca ggcagcatat tcaaggtata    540
tcctctgaag ctgttatccc ttgtaaatca aatactctaa accatatacc ttttgatagt    600

```
catgtatata aagaaagaca tttgatagag aatttctttt ctaaaattaa gcattttaga    660
agagtattct ctagatttga taaaaccatt ttagcatata taggaatgat taaattagct    720
tgtactttta tttggttacg atgaatattt attttgtgc acagaaccta atttgcattt     780
ttgtgcacaa agaaaatttt tttgatataa tagactttaa taggatattt tctaaaaatt    840
aacaaatgtc tttctacgat aatagaacgc ttaatttcgt ggtaataata gttttaacta    900
ttattactgt taattggact ttctatattt tcaagcaaga tgttaattta cattttttac    960
ttgcattagt tttgctgaga tgcttgtcat cttttttact acttagagat tatatggcta   1020
gttggcgtaa gtcgactcaa aaacttttt tacgtaaggc ttttattaat ttgccagtat    1080
ttttcatagt ggcattattt ttttatggca aagtcacttt ttcgttgata ttctctgagt   1140
ttttatttta tgttttttg atcagtttaa gtgtctactt ttattggtat ttgatgaaca    1200
gaggatcagt ggataaaagt aaaactgcgg ttatttatgg tgcaggtgct gcaggaacaa   1260
agattgctca agaacttgct tctgctggtt atcgcatcaa atgttttgtt gatgacaatg   1320
aaactttaca aaaagaagt attgatagta aaaaggttct atctaaagct gaattaacaa    1380
aactattgct atctagtaga tttgaccttt tggttattgc attgccaaga aatgcaaacc   1440
aagtagtcaa aaatatatat aaagaatttg aaaaggattt taatcagatt agaattatgc   1500
cgcctcttga ggaaattctt caagatgaga attttatgtc acagttgaag cctgttttcac  1560 tctatgatct attagcgcgt gatactaaga gtttagataa agaatctatc tctaatttta   1620
tcaaaaataa ggtggtgcta gtcacaggag ctggaggtag tataggttct gaaatagtac   1680
atcaatgtat caagtatcag gcaaaagagt tgatattggt tgatcatagt gagtttaact   1740
tatataaaat tactgaggag tgtagtcatt ttaatatcaa tagtgtgcta tgttctgttt   1800
gtgatagaaa agcattggct gaggttttc aaaagtatac tccaaatata gtatttcatg    1860
ctgctgccta caagcatgtt cccttagttg aggagaatat ctctagagca attagaaata   1920
atatcttagg tactaagaat gctatagatc tggctataga agctggtgtt gagtcattta   1980
tattgatttc cactgataaa gcagtgcgac caacgaatgt tatgggggct accaagagag   2040
tttgtgagct gtatttacag aatgttgatc ccaaaaatac caagcttgct gcagtgcgtt   2100
ttggtaatgt gcttggtagt agtggcagtg tgattccaaa atttgaagag caaataagaa   2160
aaggtggtcc tgttacagtt actcatcctg aaattcacg ttattttatg ttgataccag    2220
aagcttgtga actggtccta caagctggtg ctattgcaaa aaattcagag gtcttttgtct  2280 tagatatggg gcaacctgtc aagattattg atcttgctaa acaatttatt agactttctg   2340
gtagaggtga tattgatatt aaaatagttg gtttgcgtcc aggagagaaa ctttacgaag   2400
agcttttgat agaggaagat gatgttagta ccgactataa agatattttt attggtagaa   2460 ggactttta cgatattaat actctaaacc aagatattga atcgttgatc aaggatgatg    2520
ttgatcagct tgtgatatta agaaaaattg ttccggaatt tgaacataga ttgaatgggt   2580
agtggtttta tgttttatga ggttttaaa agattgcttg atatttact ttcttttatg     2640 gggttgttgt tattaagtcc tattttctta attattattt ttatgataaa gaaagattca   2700
aaaggaccta tatttttaa acaaaagcgc tatggtaaag ataagcaatt tttttacata    2760 tataagtta gaactatgta tgttgatact ccaaaagata tgccaacgca catgttacag    2820
gatccatcga aatgtataac taaggttgga ggatttttaa ggaaatcatc tttagatgag   2880
ttgccacaaa ttataaatat tctaaaaggt gaaatgagca tcgtgggtcc aagaccagca   2940
ttatggaatc aagatgactt aatagcacaa agagataagt atggggcaaa tgctgtgcct   3000
```

```
gtgggactga ctggctgggc acagattaat ggtagggatg aattaccaat acctgataaa    3060
gctaaacttg atggtgatta tgtaaaaaat aaaagtacat ggtttgattt aaaatgtatt    3120
tttttgacag tattttctgt ttttgccaaa aagggcgtcg ttgagggtgg tactggagct    3180
ttaggtaaca aagaggattt aaagtagtat gaaaaaaaga atcttagtta caggtttgag    3240
tagctatatt ggtaactcat ttgcggctaa atataactca gattttagta tcgataaaat    3300
atctttgcgc gatgtttcgt gggcaaatat agacttaagt ggttatgatg ctgtattgca    3360
tgtcgctgga attgcccata cttcaaagga tcctaaacta aaagaaaaat actataaaat    3420
aaatacgcaa ttaacttatg atctggcaaa acaagctaaa gatcaaggtg ttcgacagtt    3480
tgtgttttta agtagtatta tagtttatgg tgatagtgcg ccaataggtc aacaaaaagt    3540
tataactaaa tataccgaac ctaaaccaga tgattttttat ggagatagta agcttcaaac    3600
tgaaattaag ctaaatagcc tggctagtga tgactttaat attgctataa tcagaccacc    3660
aatggtatat ggagaaggct caaaaggcaa ctatccaaag ttggttaaac ttgcaaagta    3720
tacttttatt tttcctaata ttaataacca aagaagtgtt atatctatag ataatttatc    3780
taaagagatt gcagaaataa ttttgcaaac taaacatgga gtttttctac ttcaagataa    3840
tgaatatttt tgcacttcac agtttataaa aaactataga aaagatgttt taggtaagag    3900
aacttatctg acaaaaattt ttaatccaat tataagattg cttgctaaaa aagtagattt    3960
tattaataaa gttttttggga atttgactta tgagaagtaa gttattattc atagctaatg    4020
attttgatat tgtaatatat cgtttcagaa gagaagtaat cgagtctttt gctgctaaag    4080
agtatgagat agtactagta acaccatatt ctaagaaagc agaggttttt tgtaaaagtc    4140
ttggtgttaa gtatataaat gttgatatag atagacgagg caaaaatcct tttaaggatt    4200
tgcttctttt atttaactat ttcaaaataa taaaaaaaga aaaacctgat tacattttta    4260
gctatacaat taaaccaaat ttgtatgttg ggttagtgaa tttgtttttt aggaagaagt    4320
tttatccaaa tgtaacaggc ttaggaagtg tttttgctaa tcatggtatt gttcagaagt    4380
ttataatatc tttatataag ttatcattta aaagcaccac aaaagtattc tttcagaatg    4440
agcaaaataa aaagttattt atagctaaga aaataatcag tggagaaaaa tcaatattat    4500
taccaggttc tggggtaaac ttagatgaaa ataaatatgt tgactatcct aaagaccaag    4560
gaatattaaa attcgttttt cttggccgaa taatgaaaga aaaggggatt tatgaattgt    4620
tagaagcctt tgctatactt gagaaaaaat ataaaaatat tagtcttgac atttatggtt    4680
tttgtgatga aaataaatct aattttatgg gaaaggttaa tacgataaaa tcagtaaaat    4740
tttatggttt tactgataat actaaagaaa aaatagctag tgcacatgca gttgttttgc    4800
catcttacca tgaaggaatg tcaaatgtgc tgttagaagc agctgcgata ggtagacctg    4860
taattgcgtc agatattcct gggtgtagag aaattttga tgatggtctc tctggcttat    4920
catgtaaccc taatgatgtg agttctttac gtaactcatt agagcagttt ataaatatgt    4980
cgtatactga taaatagct atgagctata agctagagc taagatagaa aaagattttg    5040
atagaagtat tgttgtcaat gcatacttac agcaaaatta ataataaggg tttaaattat    5100
gagtttatat gaggatatag tcgctaaaag agaaaaggtt tcattggttg cttgggtta    5160 tgttggttta ccaatagcta ttgcatttgc aaaaaaaata gatgtgttag gatttgatat    5220
ttgtgaaaca aaagttcaac attataagga tggttttgat ccaacaaaag aagtaggaga    5280
tgaggctgtc agaaatacga caatgaaatt tagttgtgat gaaacaagtc ttaaagagtg    5340 taaattcat attgttgcag ttcctacacc agttaaagca gataaaactc ctgatttgac    5400
```

```
gccgattatt aaggcaagtg agacggttgg taggaatctt gtcaaaggcg cttatgttgt    5460
gtttgaatca actgtttatc ctggtgttac agaagatgtt tgcgtaccaa tacttgaaaa    5520
agagtctggc ttgaggtctg gtgaagattt caaagttggt tactctcctg agaggataaa    5580
tcctggtgat aaggttcata ggttagaaac aattatcaaa gtagtatctg gtatggatga    5640
agagtcttta gatactatag caaaagttta tgagctagta gtagacgcag gagtttatag    5700
agctagtagt ataaaagtgg ctgaagctgc taaggttata gaaaactctc aaagagatgt    5760
taatatagct tttgttaatg agttatcgat aatatttaat cagatgggta ttgatactct    5820
agaggtttta gcagcagctg caactaaatg gaatttctta aactttaagc ctggtcttgt    5880
tggtggacat tgtattggtg ttgacccata ttacctaacg tacaaggcag ctgagcttgg    5940
atatcattct caggtaatat tatctggtcg taggataaat gatagtatgg gtaaatttgt    6000
agttgagaat ttagtcaaaa aactgatatc tgcagatata cctgttaagc gagctagagt    6060
agcaattttc ggctttactt ttaaagaaga ctgtcctgac actaggaata ctcgagttat    6120
agatatggta aaagagctca acgagtatgg tatagagcca tatattatag atccggtagc    6180
tgataaagaa gaggctaaac atgagtatgg acttgagttt gatgatctaa gtaaaatggt    6240
caatctagat gcgatcatta ttgctgttag tcacgaacag tttaaagata taacaaagca    6300
acagtttgat aggctatatg cgcataattc tagaaagatt atatttgaca tcaaaggtag    6360
tttagataaa tctgagtttg aaaaagatta tatttattgg agattgtagt ggcttacgat    6420
aatgttaaat ttcctcatgg ttcgtttttt ttggtgactg gaggtgcggg ttttattggc    6480
tctaatttat gtgaagtttt acttagtaag ggttatagag ttaggtgttt agatgatctc    6540
tcaaatggtc actatcacaa tgttgagccg ttttaacta attctaatta tgagtttata    6600
aaaggtgata ttagagattt agatacttgc atgaaagctt gtgaaggtat tgattatgtt    6660
ctacatcaag ctgcttgggg aagcgtacca agaagtattg agatgccatt agtgtatgaa    6720
gatataaatg ttaaaggtgc attaaatatg cttgaagcgg ctagacaaaa taacgttaaa    6780
aaatttgtct atgcttctag ttcatcagta tatggtgatg agccaaattt acctaaaaaa    6840
gaaggtagaa aaggaaatgt tttatcaccc tatgcatttta caaagaaagc taatgaagag    6900
tgggcgagac tatacacaaa gttatatggt ctagatactt atggtctaag atattttaat    6960
gttttcggta aaagacaaga tcctaatggt gcgtatgcag cagttatacc taaatttatc    7020
aaacagttat taaatgatga agcgccaact ataaatggag atggtaaaca gtcgagagat    7080
tttacatata tagagaatgt tattgaggca aatcttaaag catgtttagc agatagtaag    7140
tatgccggag agtcttttaa tatagcttat ggaggtagag agtatcttat agatttgtac    7200
tataatcttt gtgatgcctt gggtaaaaaa atagagccaa attttggtcc agatagagcg    7260
ggtgatatta gcatagtaa tgctgatatt tcgaaggcta ggaatatgct cggatataat    7320
ccggaatatg attttgaatt aggcataaag catgctgttg agtggtattt aattaattaa    7380
atggtatttt aatcaagtgt acataaaaaa agtgtctttt aaaatttat atttatattt    7440 actagctttt tgtattattt ttagtttaga atttaaattt gctatattga atattatagt    7500
ttatcttccg gcttgtattt tgggtttttt agctcttaaa aaactatttg tcggaaatat    7560
tgttaagaaa caattagctt tccttttttt cttttctttt ttatcaatga tttatttaat    7620
aatagtccaa ataatcttac ttgatgcagc atcattgttt cctcagtttt tatttaacat    7680
tttgatcgcg ataggttttt gtaactttat ttttgtttca tatgataata atgaaaatta    7740 ttttttaat atgtctaaaa taatattttt tgttactttc ttacaatcta tttttgtatt    7800
```

```
tctttcaagg tattatatat ttttaaatga ttggatattc ttttttttag tgaaaaaagg   7860
gaatattgag atttcgaatg ttattgaata taagttaaga gtattcggac ttagtaacgc   7920
tggaggggat ggtttaggat tttcaattac tataggatta tgttttttcta tattttattt   7980
tatcaaatat attaaaggta aatctatatt taccaaactt atgctgtttg tacctttaat   8040
tcttattgtg ttttctaata ttttcatatc tagaacatca ctcttaactt cttcacttat   8100
attgttaata acaatatttt atatatatat taaaaaagaa aaattactgt ttattataat   8160
attggcgcta ttcttttttat caatatggat attgttcaaa ttaaatttga atttgagttg   8220
ggcttttgaa aatatttact cgtacattca atctggcgat ttttcacatg gaagtctaag   8280
tgttttaatc aataaaatgc tttttgtgcc agataacctt ttgacttgga tatttggttg   8340
tgaggatgtt agtaatactg atattggtta tattaaatat ttatactatt atgggattat   8400
atttagtatg ttttttttata ttcttattat tttcttgtac tttgaaatga gaaaatgttt   8460
tatattttca gagtatcgat cattatttct attgttgtta atagtatgtt tagttttttca   8520
agcaaaaata atttttttga cagtaggatt atttactaaa ttaaccatta tattatttat   8580
ttttctctt aaagaaaaca gctttacaac taggagtgtg atttgaaaag gtttgtacat   8640
ttaataataa accttaaccaa aggtggtgct gaaacaatgc tttataaact ttgcaaatct   8700
atggataagt caatatatca tattacgatt atatcactta tgggtagggg agtatttgca   8760
aataagttag aagcttatgg tgttaaagtt tatacattaa atttaaataa atttaatgta   8820
ctatttgtat tgtttaaata tattaagatt atcagaagaa taaagcctga tgttattcat   8880
gcttggatgt atcatgcaaa tgtaaatttct atattatgca agccttttta tagaaagact   8940
aaatatataa atagtataag aatgggattg gagaattatg atggtcataa gaatcttaca   9000
aagtttatga taaagttgaa tgcaaaattt tctaagttct cagatttaac attaaataat   9060
tcaaagaaat cattagaaga tcatcaaaat ataggtttta aaaccaatg ctttatagca   9120
aatggttttg ataagatgt ttttaaaccg agctttttaa agtatgaaaa atttcgttta   9180
aataatgatt tagatgataa tgttaaaatt ataggtatca tagcaagaaa tcatgctgat   9240
aaaaatattt ctcgtttctt acaaatagct aattttattgt taaaaagtaa tcctagttta   9300
cggttttaa ttgctggaag agagtgttcg aaaatagata taggtagtta tctagataac   9360
aaaagtaatg taaataagtt ttttgtattt gaatctgtgg attctagtga atacttacca   9420
gtattagatt tatatttgtc tacatcaaaa gttgaaggtt ttccaaatat acttgcagaa   9480
gccatgctat gtgaagttcc tattgttgct tctaatgttg gagattgtaa agatatactt   9540
aatggatacg gtgaagtttt tgagcttagt caaggtaata agaaataat agaaaagatt   9600
atgaaagttt tagaaacaac ggtagtcatg aaaaagcgca tgagagaata tataataaat   9660
aattttagta tagaagctat tttggaaaaa cacgaaaaac tttatcatga gggcagtgtc   9720
taatgtgtgg agtagtaggc ttttactcat ttaataaaga agaaggtttt gactcaataa   9780
ttaatcaatc attgctttct ataaagcata gagggtcgga tgatagtggg tattggtgcg   9840
acaatcaagt tactctgggg catactagat tatcaataca cgatataact aatgcgggac   9900
atcagccaat gttatctaat agcggtaata ctgctattgt gtttaatgga gaaatatata   9960
attacttatc cataaaaaat cagctattaa gtgaatattc aaatcttaaa tttaaaagta  10020
acagtgatac tgaggttttg gtcaatgcta ttgaactttg gggtatagat aaaacttttag  10080
aaaaatgcat aggaatgttt gcttttggag tttacagtag aaaaactagt tgcttaatac  10140
tagctagaga tagatttggc gagaagccat tatatttttgg tatccaaaat ggtatttttgg  10200
```

```
gttttgcatc agaattgaag gcacttaagc cattaaagga atgtggctgg aggtttgata   10260
tagatagaga tgctttagca acatatatga ggtatgctta tgtaccaaca ccatactcta   10320
tttataaaaa tatatctaaa ctaaatgtag gtagttacat aaaatttgat gctaaaggta   10380
atagtaaaga gtataaatat tgggattcta aaaaagtact agattcagaa aaatataaag   10440
attcgtatga tcaagcaatc ctagatttag aaattaagct taaaagtaca ctatcaatac   10500
aaatgcagtc agatgttcct ctaggagcat ttttatccgg aggaattgac tcaacaactg   10560
tagttgctct tatgcaaagt atgtctaaag ataagataaa cacttttagt ataggtttta   10620
atcaaaaaga atataatgaa gctgagcatg caagagcagt agcaaaacat ataggtacaa   10680
accacacaga tatgtatgtt acagaaagag atgctcttga tgtaatacca aaacttgctg   10740
gaatatatga cgagcccttt gctgattcat cacaaatacc aacgtatctt gtgagtaaaa   10800
tagctaagtc gaaagtaaca gttgcactat caggtgacgc tggtgatgag ctctttggcg   10860
gttataatag atactttta gcaccaaata ttgctaaaaa aatcaaattt gctaagttac   10920
ttaaatatgc accagatgct tggataaaaa aagctgagat attaaatttt ggtaagttcg   10980
ctttattagc agataaacta ctaaaactaa aagagttct cgaaaaagca aaaacaaata   11040
aagagcttta tgtactactt tgttcacaaa taaatgatac tagctttgtg ttaggagcaa   11100
aagagtatga tatattaaga gataagaata tttatgatat tccacaatta tctttccaag   11160
agtggatgat gtttgttgat tctaatacat atatgataga tgatatattg gttaaggttg   11220
atagagcagc tatggctaac tctctagaga caagagtgcc attttagat cataatattt   11280 atgaatttgc ttattcctta ccaattgact ataaaataca acgaggtaac ggaaaaagaa   11340
ttttgaaaga tttgttatat aaatatgtgc cagaaagttt ggtcaatagg tctaagatgg   11400
ggtttggtat tccgcttgct aaatggttaa gagaagattt acgagagtgg gcagataatt   11460
tactggatta tagtaaaata gacaagcaag gttacttaag tcctgaggtg gtgcaaaaat   11520
attggcaaga gcatttgagt ggtaaaagaa attggcaagc aatattatgg aatattctaa   11580 ttttcagga gtggttagat aatgagtaaa gtaaatgtaa caaaaccata cttaccagat   11640
ataaataaat ataaagcta tgtaaataaa atatacaaaa atggatggct tactaataat   11700
ggtccgttag tgcaagagct agaaaaaaga cttgcaaagt atctaggtgt taaaaatata   11760
gttttagtat caaatggtac aattgcatta gaaatcgcgt atagagcgtt aggagtcaaa   11820
ggaagtgcaa ttactactcc attttcattt gttgctacta catcttcatt ggtttctaac   11880
aatgtaaaac cagtgtttgt tgatattgat gagaatactc taagtataga cgtctctaaa   11940
attaagtatg ctattgaaga ggatacttca gctattgtgc cagttcatgt gtttggaaat   12000
ggttgtgaag ttgaaaaaat agacatgctg gctaaaaaac ataacttaaa agttattttat   12060 gatgcagcac atgcttttga tgttaagtat aagggtgaga gtatattaaa ctatggtgat   12120
atttcgacat taagttttca tgcaacaaag attttcatt ctattgaagg aggtgcgctt   12180
atcattaatg atgatagtct tgttgaaaaa gttcgttatt tcattaattt tggtatagaa   12240
agctcagaat caataccctta cttaggtact aatgctaaaa tgaatgaatt tgaggcggct   12300
atgggacttt gtgttctaga tgatattata gaaattaaga gcaaaaggaa agttattaca   12360
gagatatatg aggctgggtt agatggattg gtaaagtttc aagaacagaa tcagcattct   12420
agtaggaatt atagctattt tccagtaata tttaggactg aggaggaact tctcagagta   12480
cagaaagcac taatacaaaa tgatataata tcgcgtagat atttttatcc atcattgat   12540 agtcttagtt atatagagcc aaagcagtat atgccaatct caagagatat atctaaaaga   12600
```

```
atattatgtt tgccaattta tgcagagtta gaagacgata aaattaataa aataattaat   12660
aatatcaaag aggtttcctc atgaaaaaaa tatttgttgt tacagataat agaactattc   12720
taagtgattt taaaaatatc attggtagta aaaatgatgt agaggttgat tattttttgta   12780 gtttcaagag tcaaacttct tttgccaaag aaatatataa cagtgagatt aagccaatag   12840
atatgaaaaa aaatggcaat gatcttattg gtaagtatga tttaggtttt tcttgtcatt   12900
cgaaacaatt atttccagca aaattagtta attcagtatt atgtataaat attcatcctg   12960
gacttaatcc atataataga gggtggtttc cacaggtctt ctctattata aataaactac   13020
ctataggagc aactattcat gtgatggatg aagagataga tcatggagat ataatcattc   13080
aggaagaagt tgaagttaat tctttcgaaa actcttttga tgtttatgct aaagttcaaa   13140
aaaaagaagt tgagttgttc actaaagtca tagatgatat tttgaataat aagttccactc  13200 gaatcaaacc taactccgaa ggcaactata attcaattca tgattataaa aacatgtgtg   13260
aaattgattt agataaaata gtaacaatgc gggaagcaat tgactatcta agggctatga   13320
cacaccctcc atataaaaat agttatttca ttgatgagca tggaaataaa gtatttgttg   13380
ctcttgaact tgaaaagata agttagaaaa atgagcctta aaaaaaatac aatatcaaat   13440
tatataacac aactatatac tagcttaatt ggtattgtta tacttccttt gtatttacaa   13500
catttaagtc atgatgcatt tggtctgatt ggtttttttta cagttttttca aacgtggtta   13560 cggttgttgg atgttggtat aacaccaact ttatcaagag aagtggctca tgttagaggt   13620
agtactgatg actatcatta cttacgcaag ttggttagat cgttagagct atttttcatt   13680
attgttggtg ttctggtatt tattgtaatt agtacacatt caaggtatat atccacctct   13740
tggttacata taggctcgct agatgctgat agtgtaagtg tatgtattgc acttatgggt   13800
ttaatgtttg cattaagatg ggtgtctgat ctatatggtg gtggtttgcg tggctttgaa   13860
agacaggttc tttataataa tttaagtatc atacaaacga cactacagtt tattggtgga   13920
ttattattta tctgctatgt gtctactaat attatgtatt attttgtata tcagacaata   13980
attgcgatac tatatctagt atgtattgca attgcatttt ataaaaatact accatcatca   14040 tttagcgtgg gtttaaggtt tgattttaaa ataattagaa aagtgcttcc atttgcacta   14100
ggcattgcat attctacaac agtttggatt attgtcactc aatctgataa attagtgttc   14160
tcacatgtat taccattatc tgagtatggt tatttatctt tattgatagt gatatctagt   14220
gctgttacga tattgtcctc tccgattagc atagctattc agcctagaat gacaatgcta   14280
ttagcccaac aaaatgtaaa aggaatggaa agcttatatt taaaatcatc cttgatctca   14340
attacttttt tatctgctgt agtaacatgt gttttgatgt attctcatca gctgttgcag   14400
tcatggacag gaagtatgga aattgctaat tggggtagta atatcttaaa tatatatgtt   14460
ttatcagcat ctattatttg tataatatca tttcaatatt ttttacagta tgcttatggt   14520
aagttaaagc tacataatac atataataca attagtttag tatttttttgc tcctatagtt   14580 atatatactg cttataatta tggagtgtat actacagcac tattatggct tggatatgct   14640
atagtggggc tgataatctg gatgcctatt gtacaccatg tatttgctaa aggtatcaat   14700
aggtattttt ttataaattt agcagttatt actatagtat gttttttatt atcgttaata   14760
tttaagggtt ggtatattta tccaagtaaa attgggttgg tagaattaat attgattggg   14820
tttgcatttt tatttataca aatttgtata gagtatgttt tgtttcggta caaggttttg   14880
aggtgtatag atgattaaag tttcagtatg tgtgatgaca tacaatcaag aaaagtatat   14940
tggtcaatgt ttagagtctt tggttactca agagactgat tttgactttg agataatcgt   15000
```

-continued

```
tggagatgat tttctacag atggtacaag agatgttatt caagagtatc aaaaaaagta    15060
tccggatatc ataaagccag tttttagaga taagaatgtg ggaattactg aaaatattaa    15120
agaaatctat tttgttgcaa atggtgagta tatagctcat atggatggtg atgattatgc    15180
attgcctggt aaacttcaaa ttcaggctga tttttttggat aataatccaa gatgtacggg    15240
agttttcat aatataaata tactctatcc aaatggtaat atacaacata gtaggtttgc    15300
ttgttcaaat aagagtatat tcaatttatc agacactta cgcggagttg ctgttggtgc    15360
aaatagttca aaaatgttca gaacatcggt tttggatgat ttgattttac cggatataga    15420
gcttctagat tattatttc atgttataac agcagaaaaa ggttatttaa gtttttttaaa    15480
ttctaatgaa tcctatagtg tgtacagaaa aggtattggt atcacatcta agtctaagga    15540
aaaatctat aatacttatg ctggattatt tgaatatttt ttggatagat atcctgaaga    15600
gaaattaaat atttgtatcc ctgttgtgca atgataatt tcggctatta agggagatg    15660
ttttattagt gctattcgtc tattcaaaat tttaattaga tcaagatgta ttccattagt    15720
aagttggttt aaatatagat ttgaaaata aatatcattt agaggattat gtgaaatgaa    15780
gggaataatt ctagctggtg gcagtggtac aaggctatat ccacttaccct tgggtgttag    15840
caaacagctg ctacctgttt atgacaagcc attgttatac tatccactat ctgtgcttat    15900
gcttgcaggt attagggaga tattaattat ctctacagtg cgtgatatct cacttatcca    15960
agagcttctt ggtgatggtt cacaatttgg tatacagttg agttataaaa tccagccatc    16020
accagatggg cttgctcaag catttattct tggtgaggag ttttggcgg gtgactcagc    16080
ttgtttgata ttaggagata atatctacta tggtcaaggt atgactacaa tgctagagtc    16140
tgcaagagca cagtgtggag gtccagctgg tggcgcttgt gtttttggtt attatgttaa    16200
tgatccgcat agatatggta tagtcgaatt tgataagcaa aaaaatgtaa tttcggtaga    16260
ggaaaagcca cagaatccta agtcacacta tgctatcaca ggtttatatt tttatgataa    16320
taatgttgtt gagtatgcta aacaagtcaa accatctgca cgtggtgagc tagagattac    16380
ttcacttaat gagttatatc taaaagaaaa taagctaaat gtcgaactct tagggcgtgg    16440
ctttgcttgg cttgatgctg gtacgcatga ttcattgcta gaggcaggtc aatatgtcgc    16500
aactattgag aaaagacaag ggcttaaaat tgcatgtttg gaagaaattg catggcgtaa    16560
aggctttatc tcaacacaac aagttctagc tcaagctgaa aaactttcta agacagagta    16620
tggtcagtat ctgaagaatt taattaagga tggtttataa attaatccgt catacccatg    16680
aaggtgggta tctcataaaa gttggatatg ttttggagat tccaatctgc gcagtaatga    16740
caggtttggt aatatatagc gatgttttac aatgactaaa aatggttta tgtatattct    16800
tacaaataag gataatactg ttctgtacat agttgtaaca tctaatttga taaaaagaat    16860
gtatgagcat aaacatagcc ttgcagatgg ttttactaaa aatataatgt taataagtta    16920
gtttattttg aaatttatga agatataaaa gcagcaattc tgtgagaaaa gcagttgaaa    16980
aaatgaaaca gatcttggaa agaacgaatt attaatgaga tgaatccgaa ttggaatgat    17040
ttatatgaat taatatgtga gtaaaacttt tgtcttactg gtgcagatag gtatctctaa    17100
atatcagatg tgattgggag attaccgcct acgcggtaat gacaagttta tgcggtaatg    17160
atagtttagt gagagaatga ctagtcacta taggaatgat gatgtaatga ggaatgaaaa    17220
aatgaactac aaaccaaaaa atatcctagt aacaggtgcg gcgggattta ttggtagtaa    17280
ctatgtgcgt atgatgttat cacgctatag tgatatcaaa ataatctcgt atgataagct    17340
tacttatgcg ggtagtttag ataatctaaa agacttgaat aatgaacata accatacttt    17400
```

```
tataaaaggt gatatttgtg atgaagtttt agtatatcaa acactgaaag aatataaaat    17460
tgatacgata gtacattttg ctgcagaatc gcatgttgat aattcaattg ctaatccaaa    17520
ggtattttta gaaacgaatg tgataggtac atttacactt ttagattgtg ctaaaaggta    17580
ttggttagat gagctaggtt tagaagaaac tagttgtagg tttcatcatg tatctactga    17640
tgaggtatat ggtaccttgg caaagatga accagccttt actgagatta aggcttatga     17700
gccaaattca ccgtattcgg catctaaggc gggatctgat catatttcta gagcatatca    17760
tcatacctat aaacttccgg taacaatttc aaattgttca acaactatg gaccatacca     17820
acatcgagag aaattaatcc ctgtagtgat aaatagttgt ataaactaca agcctattcc    17880
tgtttacgga gatggttcga atattcgaga ttggctatat gtagaagatc actgcgatgc    17940
tatccagaca attgttgaga aaggagtggt tggagaggtt tataatattg gtggtattaa    18000
tgaagttgat aatctaacct tggtaaaaac tatctgtaaa ctaatggatg aatataaacc    18060
agaaaatgct ccacattcta acttaatcac atttgtggaa gatagaaaag gacatgattg    18120
gcgttatgct attgataaca gcaagattca gaatgagtta ggatggaagc catcacaaga    18180
ttttgataag atgtttagac aaactattga gttttatcta tagcttaaat atttatctta    18240
tgagtatctc taaaaaatca atttaattta tttttgtgtt aaaaagtagt gttcgcaaga    18300
atatagttaa tccgaaagat atttgtagaa aaagatattt gtagaaatgt tataatgtct    18360
aataaaaatg ccatcatata gccaagattt tagagacatc gtaattaata aacatgaaga    18420
aggtatgacg gagttcgagc tgagtaagtt ttttaacata gataagcgta cagttgtttc    18480
atggatagag ttttataaaa gaaccggaga ttatagttca aagcaaggag ttggttgtgg    18540
cagagtcgct agctttaccg ataaaacatt gattgaacag tatttgatag atcatccaga    18600
tgcaagtgca ttagatataa aagaagcatt agcccctgat attccaagaa gtacatttta    18660
tgattgtctt aatagacttg gttttagttt taaaaaaaga ctccaaaata taagcaaaga    18720
aaagaacatg aaaggttgga gtatatagaa aaactaaaag aaatagccaa taaatttgat    18780
gtacaaatat tatatctacc tccgtactct ccagatttaa atcctattga aaaggtttgg    18840
gctaactatt aa                                                       18852
```

<210> SEQ ID NO 8
<211> LENGTH: 2142
<212> TYPE: DNA
<213> ORGANISM: Campylobacter jejuni

<400> SEQUENCE: 8

```
atgttgaaaa aagagtattt aaaaaaccct tatttagttt tgtttgcgat gattatatta     60
gcttatgttt ttagtgtatt ttgcaggttt tattgggttt ggtgggcaag tgagtttaat    120
gagtattttt tcaataatca gttaatgatc atttcaaatg atggctatgc ttttgctgag    180
ggcgcaagag atatgatagc aggttttcat cagcctaatg atttgagtta ttatggatct    240
tctttatccg cgcttactta ttggctttat aaaatcacac cttttctttt tgaaagtatc    300
attttatata tgagtacttt tttatcttct ttggtggtga ttcctactat tttgctagct    360
aacgaataca aacgtccttt aatgggcttt gtagctgctc ttttagcaag tatagcaaac    420
agttattata atcgcactat gagtgggtat tatgatacgg atatgctggt aattgttttg    480
cctatgttta ttttattttt tatggtaaga atgatttaa aaaagagactt ttttcattg     540
attgccttgc cgttatttat aggaatttat ctttggtggt atccttcaag ttatactta     600
aatgtagctt taattggact tttttttaatt tatacactta ttttttcatag aaaagaaag    660
```

-continued

| | | | | |
|---|---|---|---|---|
| atttttata | tagctgtgat | tttgtcttct | cttactcttt | caaatatagc atggttttat | 720 |
| caaagtgcca | ttatagtaat | acttttgct | ttattcgcct | tagagcaaaa acgcttaaat | 780 |
| tttatgatta | taggaatttt | aggtagtgca | actttgatat | ttttgatttt aagtggtggg | 840 |
| gttgatccta | tactttatca | gcttaaattt | tatatttta | gaagtgatga agtgcgaat | 900 |
| ttaacgcagg | gctttatgta | ttttaatgtc | aatcaaacca | tacaagaagt tgaaaatgta | 960 |
| gatcttagcg | aatttatgcg | aagaattagt | ggtagtgaaa | ttgttttttt gttttctttg | 1020 |
| tttggttttg | tatggctttt | gagaaaacat | aaaagtatga | ttatggcttt acctatattg | 1080 |
| gtgcttgggt | ttttagcctt | aaaagggggg | cttagattta | ccatttattc tgtacctgta | 1140 |
| atggccttag | gatttggttt | tttattgagc | gagtttaagg | ctataatggt taaaaaatat | 1200 |
| agccaattaa | cttcaaatgt | ttgtattgtt | tttgcaacta | ttttgacttt agctccagta | 1260 |
| tttatccata | tttacaacta | taaagcgcca | acagtttttt | ctcaaaatga agcatcatta | 1320 |
| ttaaatcaat | taaaaaatat | agccaataga | gaagattatg | tggtaacttg gtgggattat | 1380 |
| ggttatcctg | tgcgttatta | tagcgatgtg | aaaactttag | tagatggtgg aaagcattta | 1440 |
| ggtaaggata | attttttccc | ttcttttgct | ttaagcaaag | atgaacaagc tgcagctaat | 1500 |
| atggcaagac | ttagtgtaga | atatacagaa | aaaagctttt | atgctccgca aaatgatatt | 1560 |
| ttaaaaacag | acattttgca | agccatgatg | aaagattata | atcaaagcaa tgtggatttg | 1620 |
| tttctagctt | cattatcaaa | acctgatttt | aaaatcgata | cgccaaaaac tcgtgatatt | 1680 |
| tatctttata | tgcccgctag | aatgtctttg | attttttcta | cggtggctag tttttctttt | 1740 |
| attaatttag | atacaggagt | tttggataaa | ccttttacct | ttagcacagc ttatccactt | 1800 |
| gatgttaaaa | atggagaaat | ttatcttagc | aacggagtgg | ttttaagcga tgattttaga | 1860 |
| agttttaaaa | taggtgataa | tgtggtttct | gtaaatagta | tcgtagagat taattctatt | 1920 |
| aaacaaggtg | aatacaaaat | cactccaatt | gatgataagg | ctcagtttta tatttttat | 1980 |
| ttaaaggata | gtgctattcc | ttacgcacaa | tttatttaa | tggataaaac catgtttaat | 2040 |
| agtgcttatg | tgcaaatgtt | tttttagga | aattatgata | agaatttatt tgacttggtg | 2100 |
| attaattcta | gagatgctaa | ggttttaaa | cttaaaattt | aa | 2142 |

<210> SEQ ID NO 9
<211> LENGTH: 713
<212> TYPE: PRT
<213> ORGANISM: Campylobacter jejuni

<400> SEQUENCE: 9

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

```
Val Ile Pro Thr Ile Leu Leu Ala Asn Glu Tyr Lys Arg Pro Leu Met
            115                 120                 125
Gly Phe Val Ala Ala Leu Leu Ala Ser Ile Ala Asn Ser Tyr Tyr Asn
130                 135                 140
Arg Thr Met Ser Gly Tyr Tyr Asp Thr Asp Met Leu Val Ile Val Leu
145                 150                 155                 160
Pro Met Phe Ile Leu Phe Phe Met Val Arg Met Ile Leu Lys Lys Asp
                165                 170                 175
Phe Phe Ser Leu Ile Ala Leu Pro Leu Phe Ile Gly Ile Tyr Leu Trp
            180                 185                 190
Trp Tyr Pro Ser Ser Tyr Thr Leu Asn Val Ala Leu Ile Gly Leu Phe
            195                 200                 205
Leu Ile Tyr Thr Leu Ile Phe His Arg Lys Glu Lys Ile Phe Tyr Ile
210                 215                 220
Ala Val Ile Leu Ser Ser Leu Thr Leu Ser Asn Ile Ala Trp Phe Tyr
225                 230                 235                 240
Gln Ser Ala Ile Ile Val Ile Leu Phe Ala Leu Phe Ala Leu Glu Gln
                245                 250                 255
Lys Arg Leu Asn Phe Met Ile Ile Gly Ile Leu Gly Ser Ala Thr Leu
            260                 265                 270
Ile Phe Leu Ile Leu Ser Gly Gly Val Asp Pro Ile Leu Tyr Gln Leu
            275                 280                 285
Lys Phe Tyr Ile Phe Arg Ser Asp Glu Ser Ala Asn Leu Thr Gln Gly
            290                 295                 300
Phe Met Tyr Phe Asn Val Asn Gln Thr Ile Gln Glu Val Glu Asn Val
305                 310                 315                 320
Asp Leu Ser Glu Phe Met Arg Arg Ile Ser Gly Ser Glu Ile Val Phe
                325                 330                 335
Leu Phe Ser Leu Phe Gly Phe Val Trp Leu Leu Arg Lys His Lys Ser
            340                 345                 350
Met Ile Met Ala Leu Pro Ile Leu Val Leu Gly Phe Leu Ala Leu Lys
            355                 360                 365
Gly Gly Leu Arg Phe Thr Ile Tyr Ser Val Pro Val Met Ala Leu Gly
370                 375                 380
Phe Gly Phe Leu Leu Ser Glu Phe Lys Ala Ile Met Val Lys Lys Tyr
385                 390                 395                 400
Ser Gln Leu Thr Ser Asn Val Cys Ile Val Phe Ala Thr Ile Leu Thr
                405                 410                 415
Leu Ala Pro Val Phe Ile His Ile Tyr Asn Tyr Lys Ala Pro Thr Val
            420                 425                 430
Phe Ser Gln Asn Glu Ala Ser Leu Leu Asn Gln Leu Lys Asn Ile Ala
            435                 440                 445
Asn Arg Glu Asp Tyr Val Val Thr Trp Trp Asp Tyr Gly Tyr Pro Val
            450                 455                 460
Arg Tyr Tyr Ser Asp Val Lys Thr Leu Val Asp Gly Gly Lys His Leu
465                 470                 475                 480
Gly Lys Asp Asn Phe Phe Pro Ser Phe Ala Leu Ser Lys Asp Glu Gln
                485                 490                 495
Ala Ala Ala Asn Met Ala Arg Leu Ser Val Glu Tyr Thr Glu Lys Ser
            500                 505                 510
Phe Tyr Ala Pro Gln Asn Asp Ile Leu Lys Thr Asp Ile Leu Gln Ala
            515                 520                 525
```

-continued

```
Met Met Lys Asp Tyr Asn Gln Ser Asn Val Asp Leu Phe Leu Ala Ser
        530                 535                 540
Leu Ser Lys Pro Asp Phe Lys Ile Asp Thr Pro Lys Thr Arg Asp Ile
545                 550                 555                 560
Tyr Leu Tyr Met Pro Ala Arg Met Ser Leu Ile Phe Ser Thr Val Ala
                565                 570                 575
Ser Phe Ser Phe Ile Asn Leu Asp Thr Gly Val Leu Asp Lys Pro Phe
            580                 585                 590
Thr Phe Ser Thr Ala Tyr Pro Leu Asp Val Lys Asn Gly Glu Ile Tyr
        595                 600                 605
Leu Ser Asn Gly Val Val Leu Ser Asp Asp Phe Arg Ser Phe Lys Ile
    610                 615                 620
Gly Asp Asn Val Val Ser Val Asn Ser Ile Val Glu Ile Asn Ser Ile
625                 630                 635                 640
Lys Gln Gly Glu Tyr Lys Ile Thr Pro Ile Asp Asp Lys Ala Gln Phe
                645                 650                 655
Tyr Ile Phe Tyr Leu Lys Asp Ser Ala Ile Pro Tyr Ala Gln Phe Ile
            660                 665                 670
Leu Met Asp Lys Thr Met Phe Asn Ser Ala Tyr Val Gln Met Phe Phe
        675                 680                 685
Leu Gly Asn Tyr Asp Lys Asn Leu Phe Asp Leu Val Ile Asn Ser Arg
    690                 695                 700
Asp Ala Lys Val Phe Lys Leu Lys Ile
705                 710
```

```
<210> SEQ ID NO 10
<211> LENGTH: 28
<212> TYPE: DNA
<213> ORGANISM: Artificial Sequence
<220> FEATURE:
<223> OTHER INFORMATION: Primer FTfragment2rev

<400> SEQUENCE: 10
ggatcattaa tagctaaatg tagtgctg                                      28

<210> SEQ ID NO 11
<211> LENGTH: 32
<212> TYPE: DNA
<213> ORGANISM: Artificial Sequence
<220> FEATURE:
<223> OTHER INFORMATION: Primer Oant1ftfwd

<400> SEQUENCE: 11
ttttgaattc tacaggctgt caatggagaa tg                                 32

<210> SEQ ID NO 12
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 12

Asp Xaa Asn Xaa Ser
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 13

Asp Xaa Asn Xaa Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 14

Glu Xaa Asn Xaa Ser
1               5

<210> SEQ ID NO 15
<211> LENGTH: 5
<212> TYPE: PRT
<213> ORGANISM: Artificial Sequence
<220> FEATURE:
<223> OTHER INFORMATION: Glycosylation site
<220> FEATURE:
<221> NAME/KEY: MISC_FEATURE
<222> LOCATION: (1)..(5)
<223> OTHER INFORMATION: Glycosylation site wherein X is any amino acid
      except proline

<400> SEQUENCE: 15

Glu Xaa Asn Xaa Thr
1               5

<210> SEQ ID NO 16
<211> LENGTH: 2133
<212> TYPE: DNA
<213> ORGANISM: Campylobacter sputorum

<400> SEQUENCE: 16
atgtcaaatt ttaatttcgc taaatttcta aataaattac ctagactttc taaacatact      60
attttaatga ttgttttagc tgtttgtttt gggatatttt gcagatttta ctgggtagtt     120
tgggctagtg cttatccgca ttttatatgg aatgatcagc ttatgataag cacaaatgac     180
ggatatgcat tgctgagggg cacaagagat atgatagctg ttttcatca accaaacgat      240 ctttcttact atggctcatc tctttcgacg cttagcatgt ggttatataa cattttgcca     300
ttttcattag aaactatact tttgtatatg agtacatttt tatctccact cttagctgtg     360
cctttgatac ttataggtaa agaactaaac gcttcaaaag cgggttttat agctgcactt     420
ctagctatta ttgcaaatag ttattataat agaacaatga gtggatatta cgatacggat     480
atgctaaata tcactcttcc tatgatggtt ttttggagca taacaagact tgttcaaaga     540
```

-continued

```
aaagagagag taaatttaat atttattccg gtttttatgg cgatatatgg atggtggtat      600
ccatcttctt actcactatt acttgccatg attggaatgt tttttttata taccattgtt      660
tttgaaagat acgaaaaact aaactatgaa gctatggttt ttatgatttt agcaatcaca      720
agcttttcta tacaaattaa atttattata gttattgttt tgtatgcttt aatctatttt      780
taccaaagat ttttgataa aaagtaata tttgcattaa ttatggcttc gttaatatgc        840
tttatatggc ttggcgggct aaaccctata cttttaaca ttaaattta tatatttaga        900 gacattgcag atagcggtga tgctgttttt aaattttca atgtaaatca acaataaga        960 gaaagttctg cgatagattt taacacagtt gtaactagga ttagcgggca tttaatagta     1020 ttttggtat ctattatagg atatatttta tttataaaa acaataaaat tttactacta       1080
actttaccga ttctgttttt gggtcttatg tcatttaaaa gtggtttaag atttacaata    1140
tactcagttc cagtaatggc tcttggtttt ggctattttg ttatgtattg ttttgcaaaa    1200
atagatataa aagatcgttt tttaggttat gtgttttat ttgttgtaac atttagtgca     1260
ttatatccat ctttaaaaca tatttatgat tataaagtat ttcctgtttt tacacatagc    1320
gaagttgaaa gtttggataa tttaaaaaat attgcaaaaa gagaagatta tgtgctttct   1380
tggtgggatt atggttatcc gatcagatat tattcagatg taaaaactct catagatgga    1440
ggaaaacatc ttggaagtga aacttcgcc gttagctttg cacttggaag cgatcaaaat    1500
agctctgcaa atatggcaag attagaagtt gaatatacag aaaaaaatta tgaagaaaaa    1560
tttggattaa atttaaaaaa gatgatgaaa gattataatg ctacaaatgt taatgagttt    1620
ttattatcat taaagatga aaatttaact ctgccaaagc aaacaagaga tatttattac    1680
tatttaccag atagaatgat atacatatat ccgatagtgc tagatttttc tagacttgat    1740
ttgacaacag ggcaagaatt tgcccagccg ttttttatgg ttagtgagag attttcagct    1800
acaaatgata atcaaataat gttaaataac aatgtcatat taagtaatga tggcactaaa    1860
ttatcgataa atggcaactc ttatagtgta aatacatatg ttgaaacaag ttatgatcaa    1920
aacgaaaaat taaatgtaaa ttatttaac atagatccaa atagcaattt ttatgtgatt     1980
tttatgaaag attatttgag aattttggtt ttagataaaa ctttgtatga tagtgcgtat    2040
attcaacttt tgtattaga aaattatgat aaaaatttat ttgaaccagt gatttttaaac    2100 ggatcaacta aaatttataa actcaaaaaa tga                                   2133
```

<210> SEQ ID NO 17
<211> LENGTH: 710
<212> TYPE: PRT
<213> ORGANISM: Campylobacter sputorum

<400> SEQUENCE: 17

```
Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
        35                  40                  45

Ile Trp Asn Asp Gln Leu Met Ile Ser Thr Asn Asp Gly Tyr Ala Phe
    50                  55                  60

Ala Glu Gly Thr Arg Asp Met Ile Ala Gly Phe His Gln Pro Asn Asp
65                  70                  75                  80

Leu Ser Tyr Tyr Gly Ser Ser Leu Ser Thr Leu Ser Met Trp Leu Tyr
                85                  90                  95
```

-continued

```
Asn Ile Leu Pro Phe Ser Leu Glu Thr Ile Leu Leu Tyr Met Ser Thr
                100                 105                 110

Phe Leu Ser Pro Leu Leu Ala Val Pro Leu Ile Leu Ile Gly Lys Glu
            115                 120                 125

Leu Asn Ala Ser Lys Ala Gly Phe Ile Ala Ala Leu Leu Ala Ile Ile
        130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Phe Leu Tyr Thr Ile Val Phe Glu Arg Tyr
210                 215                 220

Glu Lys Leu Asn Tyr Glu Ala Met Val Phe Met Ile Leu Ala Ile Thr
225                 230                 235                 240

Ser Phe Ser Ile Gln Ile Lys Phe Ile Ile Val Ile Leu Tyr Ala
                245                 250                 255

Leu Ile Tyr Phe Tyr Gln Arg Phe Phe Asp Lys Lys Val Ile Phe Ala
            260                 265                 270

Leu Ile Met Ala Ser Leu Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
290                 295                 300

Ser Gly Asp Ala Val Phe Lys Phe Phe Asn Val Asn Gln Thr Ile Arg
305                 310                 315                 320

Glu Ser Ser Ala Ile Asp Phe Asn Thr Val Val Thr Arg Ile Ser Gly
                325                 330                 335

His Leu Ile Val Phe Leu Val Ser Ile Ile Gly Tyr Ile Leu Phe Ile
            340                 345                 350

Lys Asn Asn Lys Ile Leu Leu Leu Thr Leu Pro Ile Leu Phe Leu Gly
        355                 360                 365

Leu Met Ser Phe Lys Ser Gly Leu Arg Phe Thr Ile Tyr Ser Val Pro
370                 375                 380

Val Met Ala Leu Gly Phe Gly Tyr Phe Val Met Tyr Cys Phe Ala Lys
385                 390                 395                 400

Ile Asp Ile Lys Asp Arg Phe Leu Gly Tyr Val Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asn Leu
        435                 440                 445

Lys Asn Ile Ala Lys Arg Glu Asp Tyr Val Leu Ser Trp Trp Asp Tyr
450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495

Ser Asp Gln Asn Ser Ser Ala Asn Met Ala Arg Leu Glu Val Glu Tyr
            500                 505                 510
```

```
Thr Glu Lys Asn Tyr Glu Glu Lys Phe Gly Leu Asn Leu Lys Lys Met
        515                 520                 525

Met Lys Asp Tyr Asn Ala Thr Asn Val Asn Glu Phe Leu Leu Ser Leu
        530                 535                 540

Lys Asp Glu Asn Leu Thr Leu Pro Lys Gln Thr Arg Asp Ile Tyr Tyr
545                 550                 555                 560

Tyr Leu Pro Asp Arg Met Ile Tyr Ile Tyr Pro Ile Val Leu Asp Phe
                565                 570                 575

Ser Arg Leu Asp Leu Thr Thr Gly Gln Glu Phe Ala Gln Pro Phe Phe
                580                 585                 590

Met Val Ser Glu Arg Phe Ser Ala Thr Asn Asp Asn Gln Ile Met Leu
        595                 600                 605

Asn Asn Asn Val Ile Leu Ser Asn Asp Gly Thr Lys Leu Ser Ile Asn
        610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655

Phe Tyr Val Ile Phe Met Lys Asp Tyr Leu Arg Ile Leu Val Leu Asp
                660                 665                 670

Lys Thr Leu Tyr Asp Ser Ala Tyr Ile Gln Leu Phe Val Leu Glu Asn
        675                 680                 685

Tyr Asp Lys Asn Leu Phe Glu Pro Val Ile Leu Asn Gly Ser Thr Lys
        690                 695                 700

Ile Tyr Lys Leu Lys Lys
705                 710
```